US012558364B2

(12) United States Patent
Aldrich et al.

(10) Patent No.: US 12,558,364 B2
(45) Date of Patent: Feb. 24, 2026

(54) NEXT GENERATION REMDESIVIR ANTIVIRALS

(71) Applicant: Regents of the University of Minnesota, Minneapolis, MN (US)

(72) Inventors: Courtney C. Aldrich, Minneapolis, MN (US); Subhankar Panda, St. Paul, MN (US); Tej Poudel, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/579,271

(22) Filed: Jan. 19, 2022

(65) Prior Publication Data

US 2022/0241300 A1 Aug. 4, 2022

Related U.S. Application Data

(60) Provisional application No. 63/139,543, filed on Jan. 20, 2021.

(51) Int. Cl.
*A61K 31/675* (2006.01)
*A61K 31/706* (2006.01)
*A61P 31/14* (2006.01)

(52) U.S. Cl.
CPC .......... *A61K 31/675* (2013.01); *A61K 31/706* (2013.01); *A61P 31/14* (2018.01)

(58) Field of Classification Search
CPC ...... A61K 31/675; A61K 31/706; A61P 31/14
See application file for complete search history.

(56) References Cited

U.S. PATENT DOCUMENTS

| | | | | |
|---|---|---|---|---|
| 4,916,224 | A | 4/1990 | Vince et al. | |
| 8,012,942 | B2 | 9/2011 | Butler et al. | |
| 8,415,308 | B2 | 4/2013 | Cho et al. | |
| 8,455,451 | B2 | 6/2013 | Cho et al. | |
| 9,090,642 | B2 | 7/2015 | Cho et al. | |
| 2012/0009147 | A1 | 1/2012 | Cho et al. | |
| 2012/0020921 | A1 | 1/2012 | Cho et al. | |
| 2016/0122374 | A1 | 5/2016 | Chun et al. | |
| 2017/0071964 | A1* | 3/2017 | Clarke | A61P 31/12 |
| 2017/0226140 | A1 | 8/2017 | Clarke et al. | |
| 2017/0275322 | A1* | 9/2017 | Pinho | C07H 19/10 |
| 2018/0327437 | A1 | 11/2018 | Butler et al. | |
| 2019/0055251 | A1 | 2/2019 | Mackman et al. | |
| 2019/0255085 | A1 | 8/2019 | Clarke et al. | |
| 2019/0275063 | A1 | 9/2019 | Chun et al. | |

FOREIGN PATENT DOCUMENTS

| | | |
|---|---|---|
| CN | 110330540 | 10/2019 |
| WO | 2009132135 | 10/2009 |
| WO | 2011035250 | 3/2011 |
| WO | 2011150288 | 12/2011 |
| WO | 2012012465 | 1/2012 |
| WO | 2012012776 | 1/2012 |
| WO | 2013040492 | 3/2013 |
| WO | 2016100441 | 6/2016 |
| WO | 2016184361 | 11/2016 |
| WO | 2017184668 | 10/2017 |
| WO | 2018204198 | 11/2018 |
| WO | 2019053696 | 3/2019 |
| WO | 2019129059 | 7/2019 |
| WO | 2019133712 | 7/2019 |
| WO | WO-2021155119 A2 * | 8/2021 |

OTHER PUBLICATIONS

Agostini, Maria, "Coronavirus Susceptibility to the Antiviral Remdesivir (GS-5734) Is Mediated by the Viral Polymerase and the Proofreading Exoribonuclease", MBio, Mar. Apr. 2018 vol. 9 Issue 2, (Mar. 16, 2018), 15 pgs.
Agudo, Ruben, "Engineering human PrimPol into an efficient RNA-dependent-DNA primase polymerase", Nucleic Acids Research, 2017, vol. 45, No. 15, 9046-9058., (Jul. 26, 2017), 13 pgs.
Almeida, Jamie L., "Standards for Cell Line Authentication and Beyond", PLoS Biol 14(6); Jun. 14, 2016., (Jun. 14, 2016), 9 pgs.
Appleby, Todd, "Structural basis for RNA replication by the hepatitis C virus polymerase", Science, Feb. 13, 2015, vol. 347, Issue 6223, (Feb. 13, 2015), 5 pgs.
Billotte, S., "Synthesis of C-Substituted Cyclic Amines Using Azacycloalkyl Organozinc Reagents", Synlett, Apr. 1998., (Apr. 1998), 2 pgs.
Bockman, Matthew, "Targeting Mycobacterium tuberculosis Biotin Protein Ligase (MtBPL) with Nucleoside-Based Bisubstrate Adenylation Inhibitors", J. Med. Chem. 2015, 58, 7349-7369., (Aug. 24, 2015), 21 pgs.
Brown, Ariane, "Broad spectrum antiviral remdesivir inhibits human endemic and zoonotic deltacoronaviruses with a highly divergent RNA dependent RNA polymerase", Antiviral Research 169 (2019), (Jun. 19, 2019), 10 pgs.
Cermak, Richard, "4Amino-2a, 3wDihydroxy-1bCyclopentanemethanol Hydrochloride. Carbocyclic Ribofuranosylamine for the Synthesis of Carbocyclic Nucleosides", Tetrahedron Letters, Vo1.22, No. 25, pp. 2331-2332, 1981, (Mar. 10, 1981), 2 pgs.
Cho, Aesop, "Synthesis and antiviral activity of a series of 10-substituted4-aza-7,9-dideazaadenosine C-nucleosides", Bioorg. Med. Chem. Lett. 22 (2012) 2705-2707, (Mar. 8, 2012), 4 pgs.
Chou, Tsui-Fen, "Phosphoramidate Pronucleotides: A Comparison of the Phosphoramidase Substrate Specificity of Human and *Escherichia coli* Histidine Triad Nucleotide Binding Proteins", Molecular Pharmaceutics vol. 4, No. 2, 208-217, (Oct. 26, 2006), 10 pgs.
Chou, Tsui-Fen, "P NMR and Genetic Analysis Establish hinT as the Only *Escherichia coli* Purine Nucleoside Phosphoramidase and as Essential for Growth under High Salt Conditions", The Journal of Biological Chemistry vol. 280, No. 15, Issue of Apr. 15, p. 15356-15361, 2005, (Feb. 9, 2005), 6 pgs.

(Continued)

*Primary Examiner* — Kara R. Mcmillian
(74) *Attorney, Agent, or Firm* — Schwegman Lundberg & Woessner, P.A.

(57) ABSTRACT

The disclosure relates to compounds of the formula (I) and (II), pharmaceutical compositions comprising one or more such compounds, and methods for treating pulmonary infections with one or more such compounds (e.g., treating SARS-COV, MERS-COV or SARS-COV-2).

8 Claims, No Drawings

(56) References Cited

OTHER PUBLICATIONS

Cockrell, Adam, "A mouse model for MERS coronavirus-induced acute respiratory distress syndrome", Nature Microbiology 2, 16226 (2016)., (Nov. 28, 2016), 11 pgs.
Dawadi, Surendra, "Synthesis and pharmacological evaluation of nucleoside prodrugs designed to target siderophore biosynthesis in *Mycobacterium tuberculosis*", Bioorganic and Medicinal Chemistry 24 (2016) 1314-1321., (Feb. 3, 2016), 8 pgs.
Dawadi, Surendra, "Investigation and Conformational Analysis of Fluorinated Nucleoside Antibiotics Targeting Siderophore Biosynthesis", J. Org. Chem. 2015, 80, 4835-4850., (Apr. 27, 2015), 16 pgs.
De, Swarup, "Synthesis of a 3 Fluoro-3 deoxytetrose Adenine Phosphonate", J. Org. Chem. 2017, 82, 9464-9478., (2017), 15 pgs.
Feng, Joy, "Role of Mitochondrial RNA Polymerase in the Toxicity of Nucleotide Inhibitors of Hepatitis C Virus", Antimicrobial Agents and Chemotherapy, Feb. 2016, vol. 60 No. 2, (Feb. 2016), 12 pgs.
Feng, Qi, "Adenosine 5 triphosphate, a substrate for T7 RNA polymerase and rabbit muscle creatine kinase", J. Am. Chem. Soc., vol. 110, No. 24, 1988, Additions and Corrections, (Jun. 1, 1988), 1 pg.
Gao, Yan, "Structure of the RNA-dependent RNA polymerase from COVID-19 virus", Science, 2020., (Apr. 10, 2020), 8 pgs.
Goekjian, Peter, "Synthesis of Fluorinated Macrocyclic Bis(indolyl)maleimides as Potential 19F NMR Probes for Protein Kinase C", J. Org. Chem. 1999, 64, 4238-4246, (May 18, 1999), 9 pgs.
Gordon, Calvin, "The antiviral compound remdesivir potently inhibits RNAdependent RNA polymerase from Middle East respiratory syndrome coronavirus", J. Biol. Chem. (2020) 295(15) 4773-4779, (Feb. 24, 2020), 7 pgs.
Gordon, Calvin, "Remdesivir is a direct-acting antiviral that inhibits RNAdependent RNA polymerase from severe acute respiratory syndrome coronavirus 2 with high potency", J. Biol. Chem. (2020) 295(20) 6785-6797, (Apr. 13, 2020), 13 pgs.
Guillen-Suarez, Antonio, "Continuous Enzyme-Coupled Assay of Phosphateor Pyrophosphate-Releasing Enzymes", BioTechniques 53:99-103 (Aug. 2012), (Aug. 2012), 6 pgs.
Hauk, Dieter, "Minimization of Side Reactions in Bromine Magnesium Exchanges with i-PrMgCI LiCl and s-BuMgCl LiCl Mixtures", Organic Process Research and Development 2006, 10, 733-738, (2006), 6 pgs.
Hollenstein, Marcel, "Nucleoside Triphosphates—From Synthesis to Biochemical Characterization", Journal of Visualized Experiments, Apr. 2014, 86, e51385, http: www.jove.com video 51385 , (Apr. 3, 2014), 10 pgs.
Jessen, Henning, "Phosphate esters and anhydrides recent strategies targeting nature's favoured modifications", Org. Biomol.Chem, 2014, 12, 3526., (2014), 5 pgs.
Jung, Michael, "Allylpalladium Formation from Allylic Amines via AyV-Ditosylimides and JV-Tosylamides: Efficient Synthesis of the Antiviral Agent Carbovir", J. Org. Chem., vol. 59, No. 17, 1994, (May 18, 1994), 2 pgs.
Knowles, Deborah, "Oxidation of Primary Amines to Ketones", Synlett 2008, No. 18, pp. 2769-2772., (Oct. 15, 2008), 4 pgs.
Krasovskiy, Arkady, "A LiCl-Mediated Br Mg Exchange Reaction for the Preparation of Functionalized Aryl- and Heteroarylmagnesium Compounds from Organic Bromides", Angew. Chem. Int. Ed. 2004, 43, 3333-3336., (2004), 4 pgs.
Lodeiro, Maria, "Identification of Multiple Rate-limiting Steps during the Human Mitochondrial Transcription Cycle in Vitro", The Journal of Biological Chemistry vol. 285, No. 21, pp. 16387-16402, 2010., (Mar. 29, 2010), 16 pgs.
Ludwig, J., "Synthesis of Nucleoside 5(1,3-Dithiotriphosphates) and 5(1,1-Dithiotriphosphates", J. Org. Chem. 56 (1991) 5, 1777-1783, (Jul. 30, 1991), 2 pgs.
Ludwig, Janos, "Rapid and Efficient Synthesis of Nucleoside S' Thiotriphosphates, S Triphosphates and Cyclophosphorothioates Using 2-Chloro benzodioxaphosphorin 4 one", J. Org. Chem., vol. 54, No. 3, 1989, (1989), 5 pgs.
Metobo, S.E., "Practical synthesis of 1'-substituted Tubercidin C-nucleoside analogs", Tetrahedron Lett. 2012, 53, Issue 5, 484-486, (Nov. 18, 2011), 3 pgs.
Minskaia, Ekaterina, "Discovery of an RNA virus 3-5 exoribonuclease that is critically involved in coronavirus RNA synthesis", PNAS, Mar. 28, 2006, vol. 103, No. 13, (Mar. 28, 2006), 6 pgs.
Nelson, Kathryn, "Synthesis and Pharmacokinetic Evaluation of Siderophore Biosynthesis Inhibitors for *Mycobacterium tuberculosis*", J. Med. Chem. 2015, 58, 5459-5475, (Jun. 25, 2015), 17 pgs.
Okon, Aniekan, "Anchimerically Activated ProTides as Inhibitors of Cap-Dependent Translation and Inducers of Chemosensitization in Mantle Cell Lymphoma", J. Med. Chem. 2017, 60, 8131-8144., (Aug. 31, 2020), 14 pgs.
Saez-Alvarez, Yanira, "Development of a fluorescencebased method for the rapid determination of Zika virus polymerase activity and the screening of antiviral drugs", Scientific Reports, (2019) 9:5397., (Apr. 1, 2019), 11 pgs.
Shah, Rachit, "Caught before Released: Structural Mapping of the Reaction Trajectory for the Sofosbuvir Activating Enzyme, Human Histidine Triad Nucleotide Binding Protein 1", Biochemistry 2017, 56, 3559-3570, (Jun. 22, 2017), 12 pgs.
Sheahan, Timothy, "Broad-spectrum antiviral GS-5734 inhibits both epidemic and zoonotic coronaviruses", Sci Transl Med. Jun. 28, 2017; 9(396), (Jun. 28, 2017), 20 pgs.
Sheahan, Timothy, "Comparative therapeutic efficacy of remdesivir and combination lopinavir, ritonavir, and interferon beta against MERS-CoV", Nature Communications (2020) 11:222, (2020), 14 pgs.
Shi, CE, "Bisubstrate Inhibitors of Biotin Protein Ligase in *Mycobacterium tuberculosis* Resistant to Cyclonucleoside Formation", ACS Med. Chem. Lett. 2013, 4, 1213-1217, (Oct. 15, 2013), 5 pgs.
Siegel, Dustin, "Discovery and Synthesis of a Phosphoramidate Prodrug of a Pyrrolo triazin-4-aminoAdenine C Nucleoside (GS-5734) for the Treatment of Ebola and Emerging Viruses", J. Med. Chem. 2017, 60, 1648-1661., (Jan. 26, 2017), 14 pgs.
Singh, Rohit, "2-Azabicyclo hept-5-en-3-one: Chemical Profile of a Versatile Synthetic Building Block and its Impact on the Development of Therapeutics", Chem. Rev. 2012, 112, 4642-4686., (Jun. 8, 2012), 45 pgs.
Tchesnokov, Egor, "Mechanism of Inhibition of Ebola Virus RNA-Dependent RNA Polymerase by Remdesivir", Viruses 2019, 11, 326, (Apr. 4, 2019), 16 pgs.
Teitelbaum, Aaron, "Synthesis, pH-dependent, and plasma stability of meropenem prodrugs for potential use against drug-resistant tuberculosis", Bioorganic and Medicinal Chemistry 21 (2013) 5605-5617., (May 24, 2013), 13 pgs.
Veber, Daniel, "Molecular Properties That Influence the Oral Bioavailability of Drug Candidates", J. Med. Chem. 2002, 45, 2615-2623., (May 11, 2002), 9 pgs.
Wang, "Remdesivir and chloroquine effectively inhibit the recently emerged novel coronavirus (2019-nCoV) in vitro", Cell Research (2020) 30:269-271, (Feb. 4, 2020), 3 pgs.
Warren, Travis, "Therapeutic efficacy of the small molecule GS-5734 against Ebola virus in rhesus monkeys", Nature, vol. 531, Mar. 17, 2016, (Mar. 17, 2016), 19 pgs.

* cited by examiner

NEXT GENERATION REMDESIVIR ANTIVIRALS

CROSS-REFERENCE TO RELATED APPLICATIONS

This application claims the benefit of U.S. Provisional Appl. Ser. No. 63/139,543, filed Jan. 20, 2021, which is incorporated by reference as if fully set forth herein.

STATEMENT OF GOVERNMENT SUPPORT

This invention was made with government support under AI136445 awarded by the National Institutes of Health. The government has certain rights in the invention.

BACKGROUND

Three coronaviruses have crossed the species barrier to cause deadly pneumonia in humans since the beginning of the 21st century: severe acute respiratory syndrome coronavirus (SARS-COV), Middle-East respiratory syndrome coronavirus, and SARS-COV-2. SARS-COV emerged in the Guangdong province of China in 2002 and spread to five continents through air travel routes, infecting 8,098 people and causing 774 deaths. In 2012, MERS-COV emerged in the Arabian Peninsula, where it remains a major public health concern, and was exported to 27 countries, infecting a total of 2,494 individuals and claiming 858 lives. A previously unknown coronavirus, named SARS-COV-2, was discovered in December 2019 in Wuhan, Hubei province of China and was sequenced and isolated by January 2020. SARSCOV-2 is associated with an ongoing outbreak that has affected over 80.5 million people and killed more than 1.8 million people worldwide as of Dec. 30, 2020.

The World Health Organization declared the SARS-COV-2 epidemic a public health emergency of international concern. MERS-COV was suggested to originate from bats, but the reservoir host fueling spillover to humans is unequivocally dromedary camels. Both SARS-COV and SARS-COV-2 are closely related and originated in bats, who most likely serve as reservoir host for these two viruses. Whereas palm civets and racoon dogs have been recognized as intermediate hosts for zoonotic transmission of SARS-COV between bats and humans, the SARS-COV-2 intermediate host remains unknown. The recurrent spillovers of coronaviruses in humans along with detection of numerous coronaviruses in bats, including many SARS-related coronaviruses (SARSr-CoVs), suggest that future zoonotic transmission events may continue. In addition to the highly pathogenic zoonotic pathogens SARS-COV, MERS-COV, and SARS-CoV-2, all belonging to the β-coronavirus genus, four low-pathogenicity coronaviruses are endemic in humans: HCoV-OC43, HCoVHKU1, HCoV-NL63, and HCoV-229E.

SUMMARY

Although social distancing and mask-wearing practices have been effective in reducing the transmission of viruses generally, and coronaviruses more specifically, there is resistance to these practices in society today. Further, despite the promise that several vaccine regimens offer, their distribution and administration will not be widespread for at least six months. Some people's resistance to vaccination and the virus's ongoing mutation indicate that threats posed by coronaviruses are likely to persist. There is a need, therefore, for small molecule therapeutics for treating diseases associated with coronaviruses, including COVID-19.

DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

The disclosure generally relates to compounds of the formula (I):

(I)

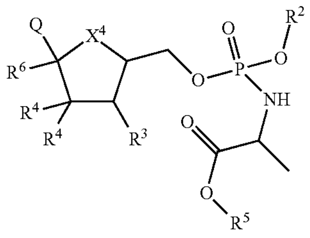

or a pharmaceutically acceptable salt, polymorph, prodrug, solvate or clathrate thereof wherein:

Q is:

$Q^1$

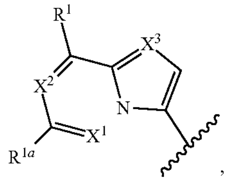

, $Q^2$

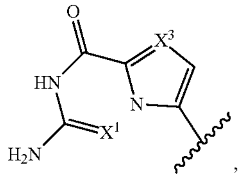

, $Q^3$

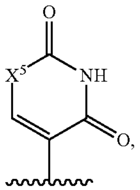

or $Q^4$

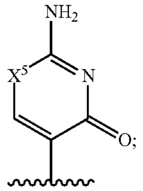

$R^1$ is H, halo, alkyl, amino or $OR^7$, wherein H, alkyl, OH or $NH_2$;

$R^{1a}$ is H, amino, alkyl, cycloalkyl, alkenyl, alkynyl, aryl, heteroaryl, halo or $OR^7$, wherein H, alkyl, OH or $NH_2$;

$R^2$ is aryl or heteroaryl;

$R^3$ and $R^4$ are each, independently, alkyl, halo, haloalkyl or $OR^7$, wherein H, alkyl, OH or $NH_2$;

$R^5$ is alkyl;

$R^6$ can be H, halo, alkyl, alkenyl, hydroxyalkyl, alkoxy, alkoxyalkyl, haloalkyl, cycloalkyl, heterocyclo, cyano, cyanoalkyl, amino, aminoalkyl, amido, amidoalkyl, $CO_2H$, $CO_2Et$, thioalkyl, $C(S)R^7$, $C(NOR^7)(R^7)$, $C(NR^7)(R^7)$ or $N_3$;

$X^1$ is N or CH;

$X^2$ is N or CH;

$X^3$ is N or CH;

$X^4$ is O, NH, S or alkyl;

$X^5$ is NH, O or S;

with the proviso that the compound of the formula (I) is not a compound of the formula:

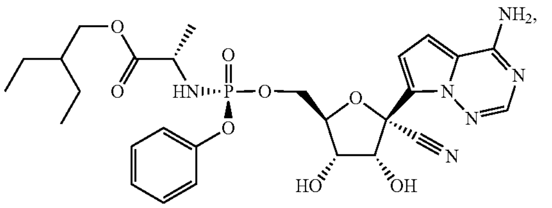

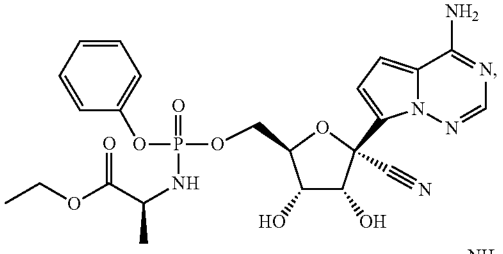

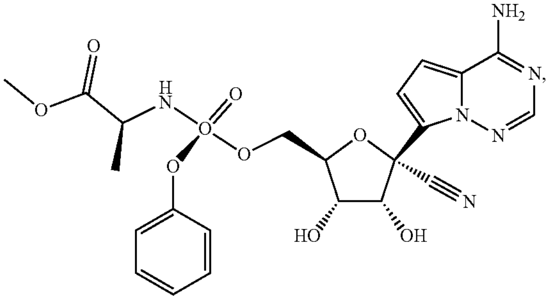

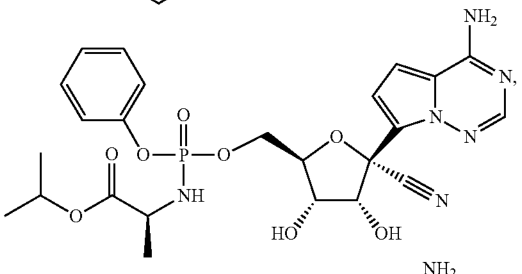

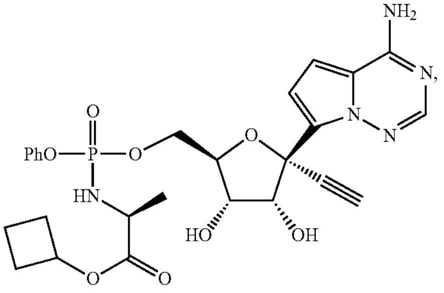

-continued

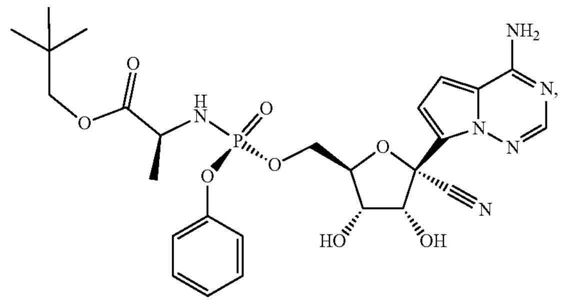

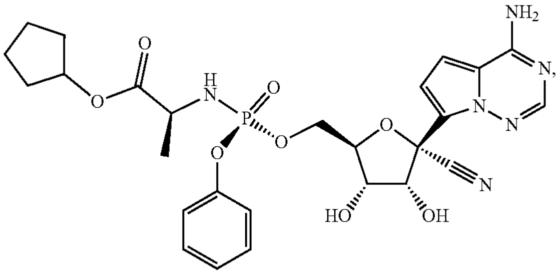

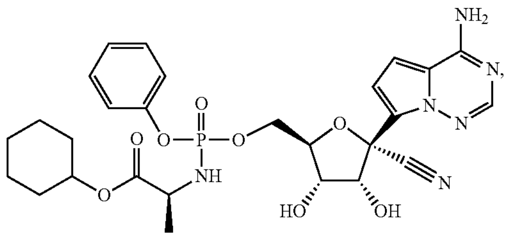

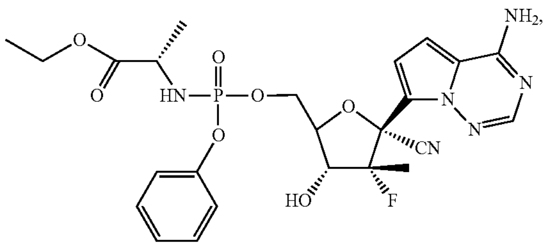

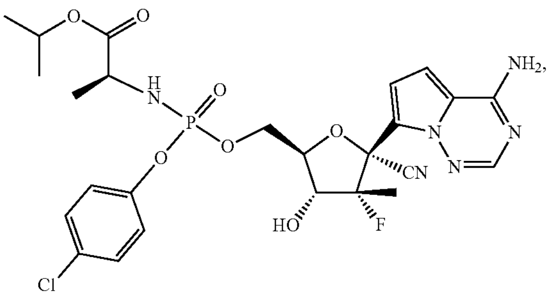

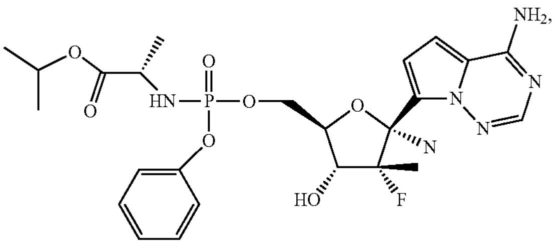

-continued

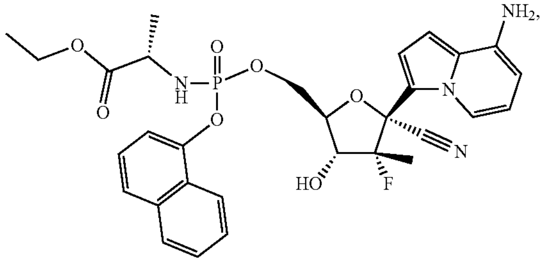

, or

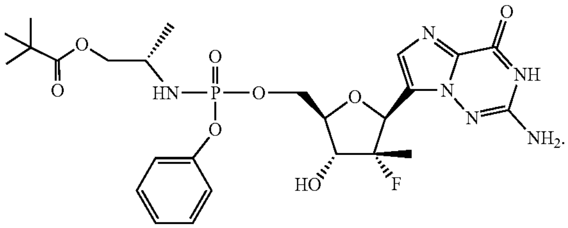

.

All stereoisomers of the compounds of formula (I) are contemplated herein, including the diastereomer of the formula:

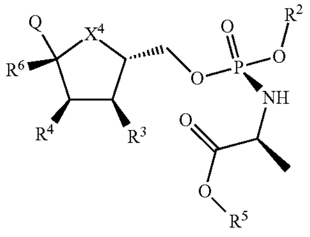

and pharmaceutically acceptable salts, polymorphs, prodrugs, solvates or clathrates thereof.

In the compounds of formula (I), Q can be $Q^1$:

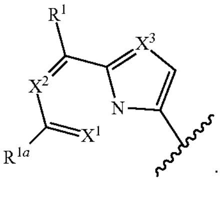

.

In addition or alternatively (e.g., when Q is $Q^2$, $Q^3$, or $Q^4$), $R^1$ can be amino, such as $NH_2$, alkylamino, dialkylamino or an amino group wherein the alkyl groups (when present) are further substituted with, e.g., an aryl group. An example of such a substitution is a benzyl group (e.g., an arylalkyl group, such as phenyl-$CH_2$). In addition, or alternatively, the groups $X^1$—$X^3$ can be any suitable combination of CH or N, such as, e.g., wherein $X^1$ and $X^3$ are N and $X^2$ is CH or N; $X^1$ and $X^2$ are N and $X^3$ is CH or N; and $X^2$ is N and $X^1$ and $X^3$ are CH or N. Thus, for example, compounds of the formula (I) are contemplated herein, wherein the groups $X^1$—$X^3$ can be chosen to form various ring systems, including the following ring systems:

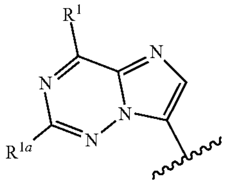

,

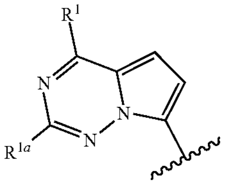

,

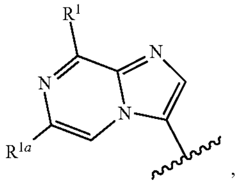

,

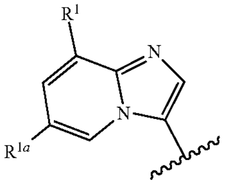

,

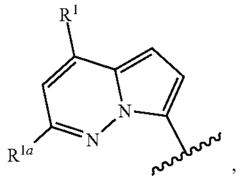

,

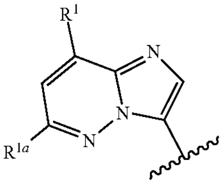

, and

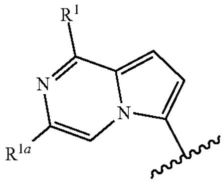

, such as:

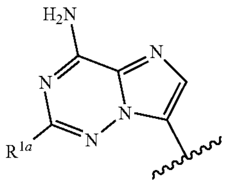

,

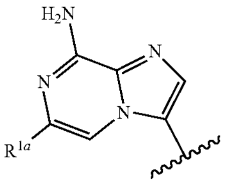

,

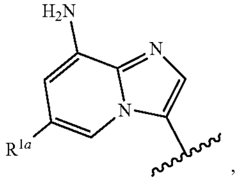

,

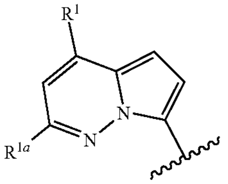

,

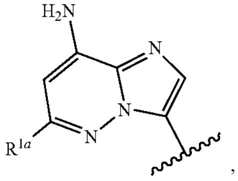

, and

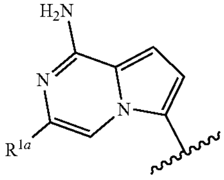

, such as:

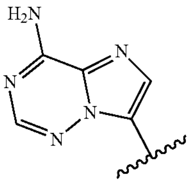

,

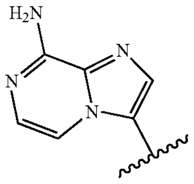

,

-continued

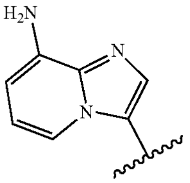
,
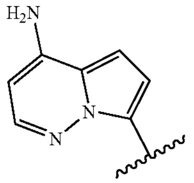
,
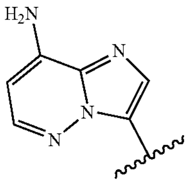
, and
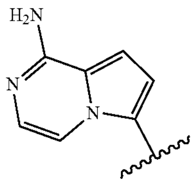
.

In addition, or alternatively, $R^2$ can be aryl, such as phenyl. In addition, or alternatively, at least one of $R^3$ and $R^4$ is OH; $R^3$ and $R^4$ are each OH; at least one of $R^3$ and $R^4$ is halo (e.g., Cl or F) or at least one of $R^3$ and $R^4$ is OH and the other is halo (e.g., Cl or F). Alternatively, or in addition, $X^4$ can be O or alkyl (e.g., $CH_2$ or $CR_2$, wherein R is defined herein and can be, among other things, halo, such that the $CR_2$ group can be, e.g., CFH, $CF_2$, and the like). Thus, for example, compounds of the formula (I) are contemplated herein wherein, the groups $R^3$ and $R^4$ can be chosen to form various ring systems, including the following ring systems:

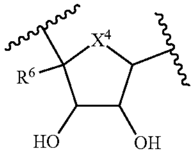
,
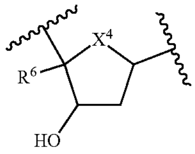
,
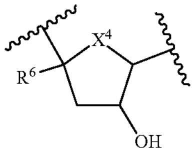
,
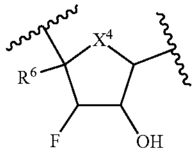
,
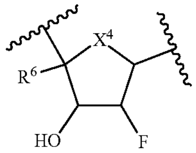
, and
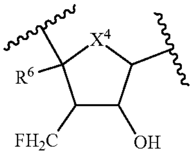

such as:

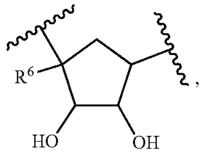
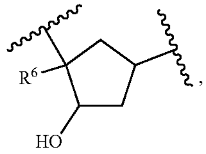
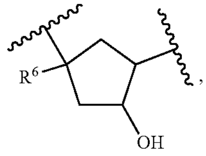
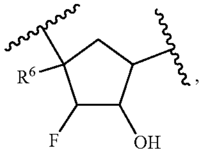

-continued

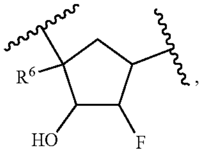
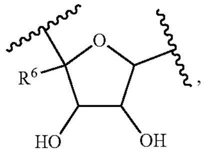
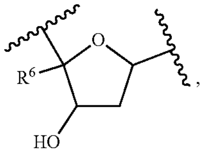
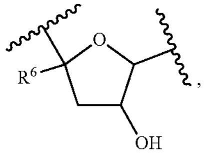
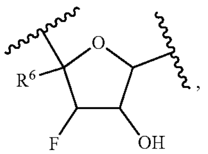
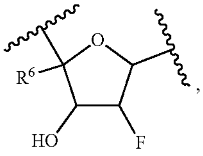
and
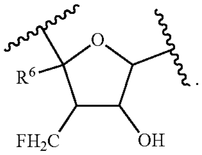

Alternatively, or in addition, $R^6$ can be CN; cycloalkyl or heterocyclo; haloalkyl; aminoalkyl, cyanoalkyl or amido; or halo or $N_3$. $R^6$ can be H, halo, alkyl (e.g., substituted or unsubstituted ($C_1$-$C_5$)-alkyl), hydroxyalkyl (e.g., ($C_1$-$C_5$)-alkyl-OH), alkoxy (e.g., substituted or unsubstituted ($C_1$-$C_8$)-alkoxy), haloalkyl (which is an example of a substituted alkyl; e.g., fluoromethyl, difluoromethyl, and chloromethyl), cycloalkyl (e.g., substituted or unsubstituted ($C_4$-$C_8$)-cycloalkyl), heterocyclo (e.g., 3-5-membered heterocyclo, such as epoxy, aziridino, oxetananyl, and azetanyl), heterocycloalkyl (e.g., a ($C_1$-$C_8$)-alkyl substituted with a 3-5-membered heterocyclo, such as epoxy, aziridino, oxetananyl, and azetanyl), cyano, cyanoalkyl (another example of substituted alkyl; e.g., substituted or unsubstituted ($C_1$-$C_8$)-alkyl-CN), amino (e.g., $NH_2$), aminoalkyl (e.g., substituted or unsubstituted ($C_1$-$C_8$)-alkyl-$NH_2$, such as $CH_2NH_2$), amido (e.g., $C(O)NR^2$, such as $C(O)NH_2$), amidoalkyl (e.g., substituted or unsubstituted ($C_1$-$C_8$)-alkyl-$C(O)NR^2$) or $N_3$.

In some embodiments, $R^6$ can be H, halo, alkyl, alkenyl, hydroxyalkyl, alkoxy, alkoxyalkyl, haloalkyl, cycloalkyl, heterocyclo, cyano, cyanoalkyl, amino, aminoalkyl, amido, amidoalkyl, $CO_2H$, $CO_2Et$, thioalkyl, $C(S)R^7$, $C(NOR^7)(R^7)$, $C(NR^7)(R^7)$ or $N_3$, wherein $R^7$ is H, alkyl, OH or $NH_2$.

Compounds of the formula (I) are contemplated herein wherein, the groups $R^6$ can be chosen to form various ring systems, including the following ring systems:

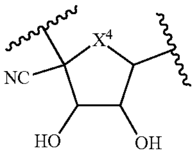
,
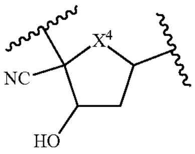
,
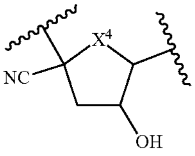
,
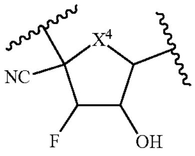
,

-continued

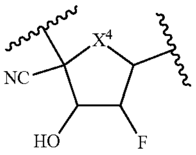
,
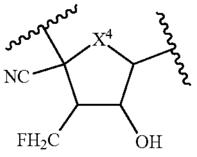
, and
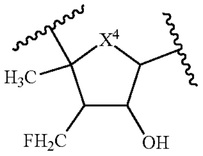

such as:

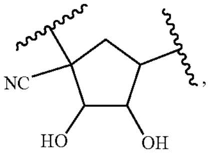
,
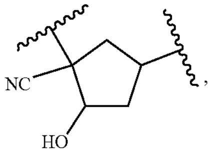
,
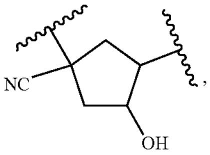
,
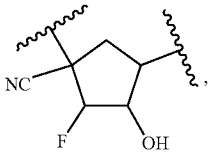
,
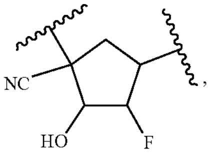
,
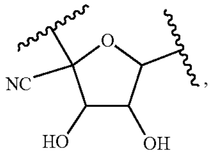
,
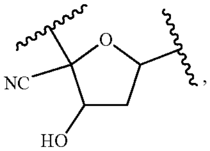
,
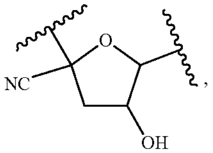
,
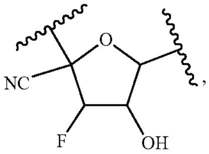
,
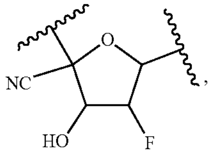
,
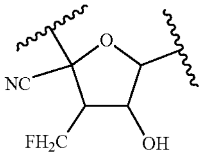
, and
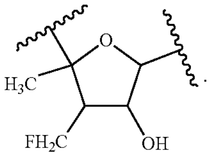
.

Or, instead of the CN group depicted in the foregoing structures, $R^6$ can be cycloalkyl or heterocyclo; haloalkyl; aminoalkyl, cyanoalkyl or amido; or halo or $N_3$. Thus, for example, $R^6$ can be any suitable substituent, including the following:

F, $N_3$, $CH_3$, $CHF_2$, $CF_3$, aminoalkyl (e.g., $CH_2NH_2$), cycloalkyl (e.g., cyclopropyl, cyclobutyl, and cyclopentyl), cyanoalkyl (e.g., $CH_2CN$), amido (e.g., $CONH_2$), $CO_2H$, ester (e.g. $CO_2Et$), oxime (e.g. C═N—OH) and heterocyclyl, such as groups of the formula:

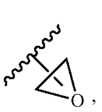
,
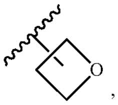
,
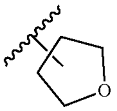
,
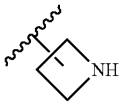
, and
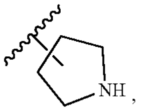
, such as

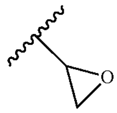
,
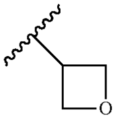
,
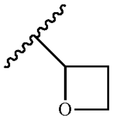
,
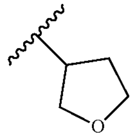
,
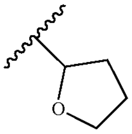
,
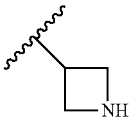
,
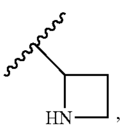
,
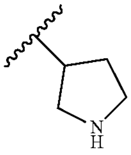
, and
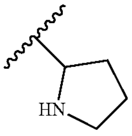
, each of which can be further substituted.

Alternatively, or in addition, $R^5$ can be $C_5$-alkyl, such as

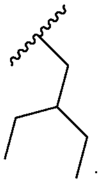 [SMILES: *CC(CC)CC]
.

Examples of compounds encompassed by formula (I) include compounds of the formula:

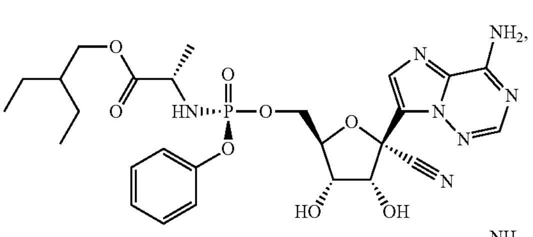

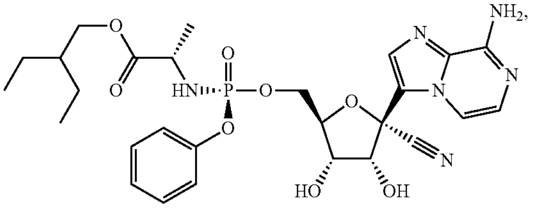

-continued
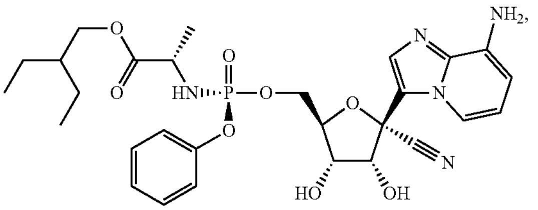
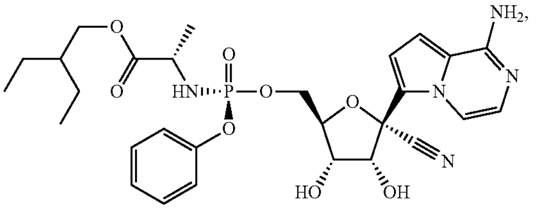
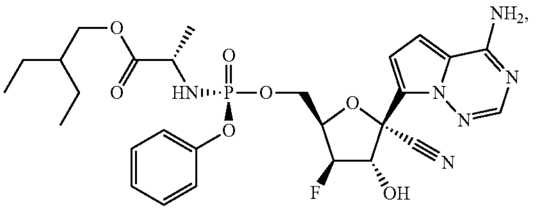
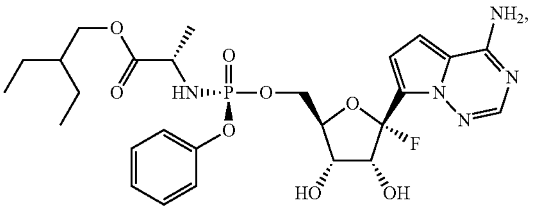
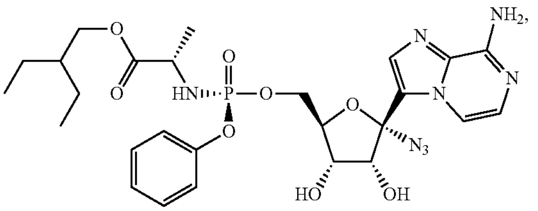
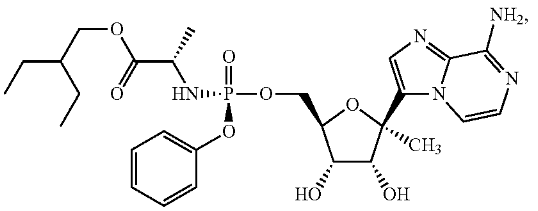
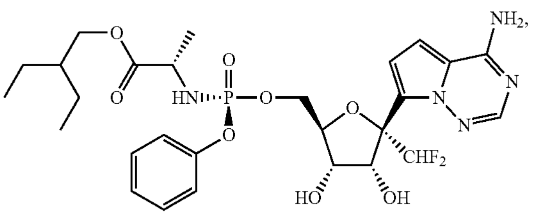
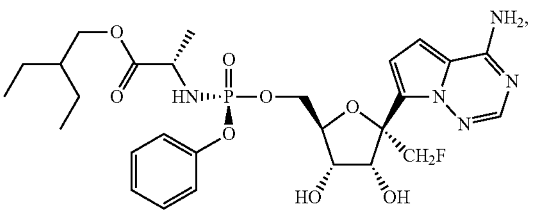
-continued
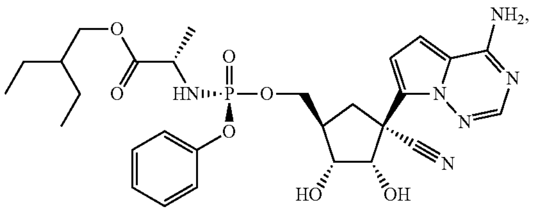
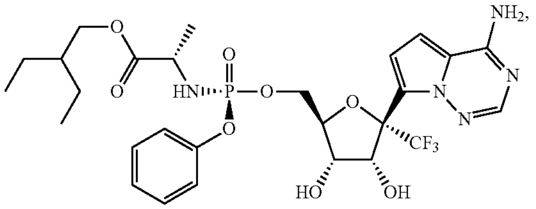
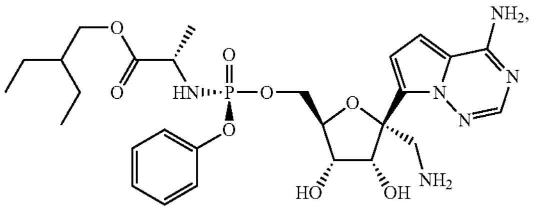
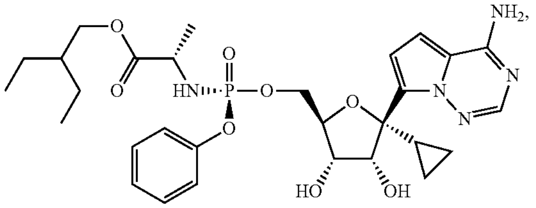
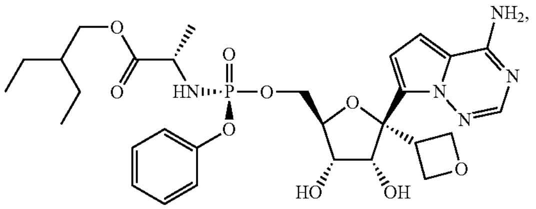
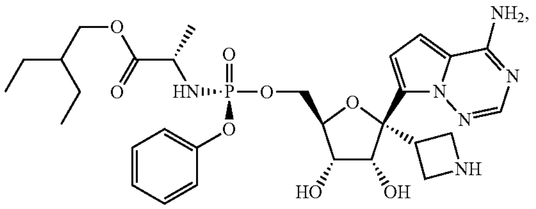
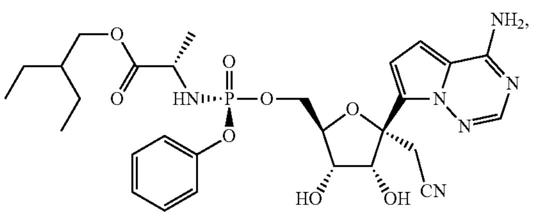
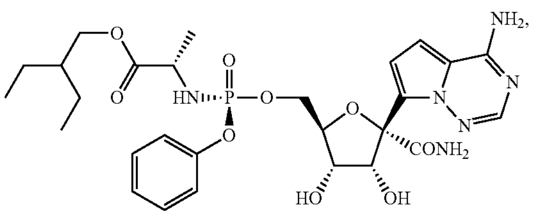

-continued

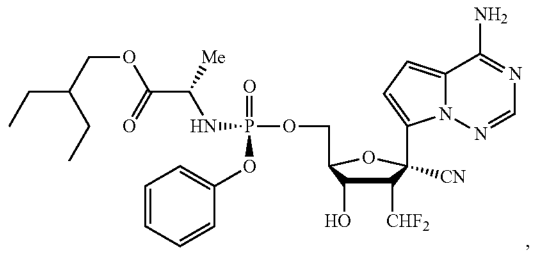

, and

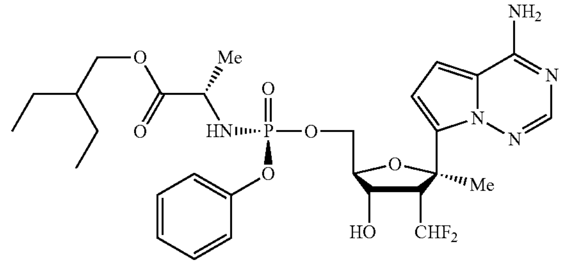

or pharmaceutically acceptable salts, polymorphs, prodrugs, solvates or clathrates thereof.

The disclosure also relates to compounds of the formula (II):

(II)

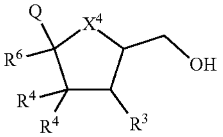

or a pharmaceutically acceptable salt, polymorph, prodrug, solvate or clathrate thereof wherein:

Q is:

$Q^1$

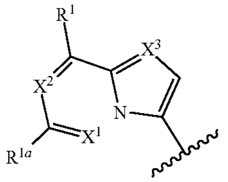

$Q^2$

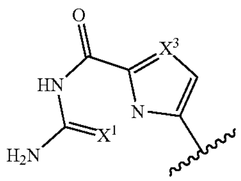

$Q^3$

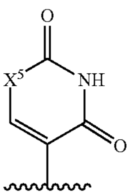

or

-continued $Q^4$

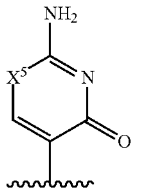

$R^1$ is H, halo, alkyl, amino or $OR^7$, wherein $R^7$ is H, alkyl, OH or $NH_2$;

$R^{1a}$ is H, amino, alkyl, cycloalkyl, alkenyl, alkynyl, aryl, heteroaryl, halo or $OR^7$, wherein $R^7$ is H, alkyl, OH or $NH_2$;

$R^3$ and $R^4$ are each, independently, alkyl, halo, haloalkyl or $OR^7$, wherein $R^7$ is H, alkyl, OH or $NH_2$;

$R^6$ can be H, halo, alkyl, alkenyl, hydroxyalkyl, alkoxy, alkoxyalkyl, haloalkyl, cycloalkyl, heterocyclo, cyano, cyanoalkyl, amino, aminoalkyl, amido, amidoalkyl, $CO_2H$, $CO_2Et$, thioalkyl, $C(S)R^7$, $C(NOR^7)(R^7)$, $C(NR^7)(R^7)$ or $N_3$;

$X^1$ is N or CH;

$X^2$ is N or CH;

$X^3$ is N or CH;

$X^4$ is O, NH, S or alkyl; and $X^5$ is NH, O or S.

All stereoisomers of the compounds of formula (II) are contemplated herein, including the diastereomer of the formula:

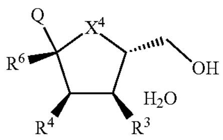

and pharmaceutically acceptable salts, polymorphs, prodrugs, solvates or clathrates thereof.

In the compounds of formula (II), Q can be $Q^1$:

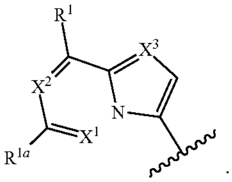

.

In addition or alternatively (e.g., when Q is $Q^2$, $Q^3$, or $Q^4$), $R^1$ can be amino, such as $NH_2$, alkylamino, dialkylamino or an amino group wherein the alkyl groups (when present) are further substituted with, e.g., an aryl group. An example of such a substitution is a benzyl group (e.g., an arylalkyl group, such as phenyl-$CH_2$). In addition, or alternatively, the groups $X^1$—$X^3$ can be any suitable combination of CH or N, such as, e.g., wherein $X^1$ and $X^3$ are N and $X^2$ is CH or N; $X^1$ and $X^2$ are N and $X^3$ is CH or N; and $X^2$ is N and $X^1$ and $X^3$ are CH or N. Thus, for example, compounds of the formula (II) are contemplated herein, wherein the groups $X^1$—$X^3$ can be chosen to form various ring systems, including the following ring systems:

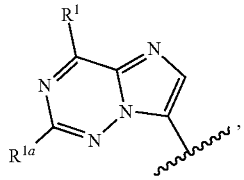, 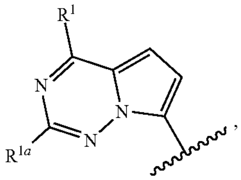,

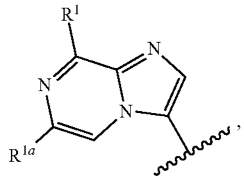, 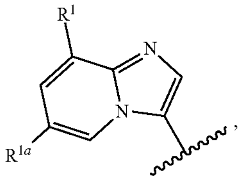,

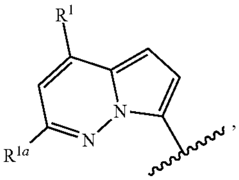, 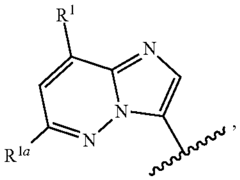, and

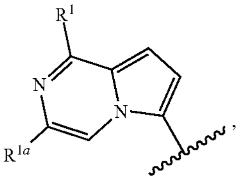, such as:

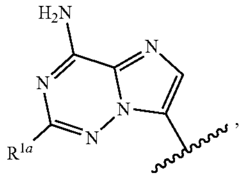, 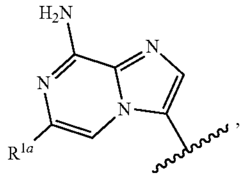,

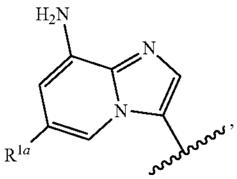, 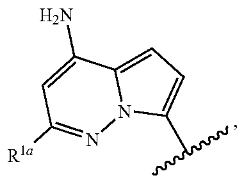,

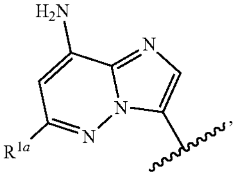, and

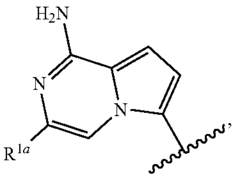, such as: 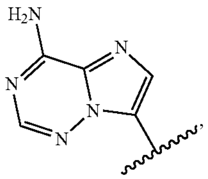,

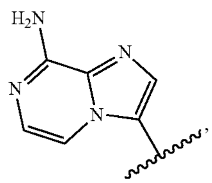, 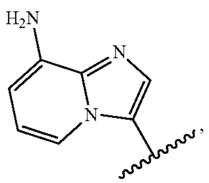,

-continued

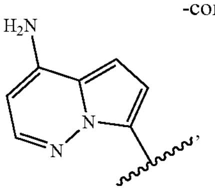, 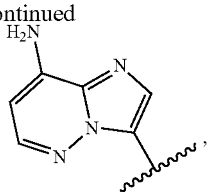, and

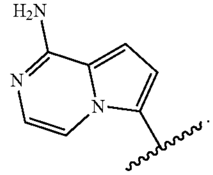.

In addition, or alternatively, at least one of $R^3$ and $R^4$ is OH; $R^3$ and $R^4$ are each OH; at least one of $R^3$ and $R^4$ is halo (e.g., Cl or F) or at least one of $R^3$ and $R^4$ is OH and the other is halo (e.g., Cl or F). Alternatively, or in addition, $X^4$ can be O or alkyl (e.g., $CH_2$ or $CR_2$, wherein R is defined herein and can be, among other things, halo, such that the $CR_2$ group can be, e.g., CFH, $CF_2$, and the like). Thus, for example, compounds of the formula (II) are contemplated herein wherein, the groups $R^3$ and $R^4$ can be chosen to form various ring systems, including the following ring systems:

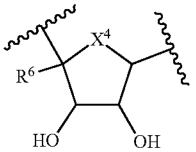, 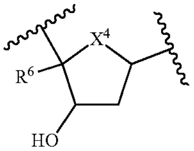,

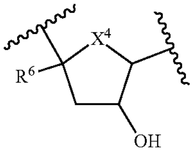, 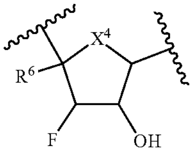,

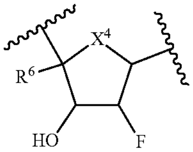, and 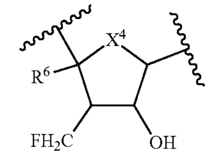

such as:

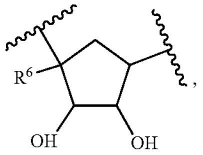, 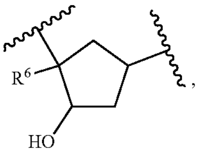,

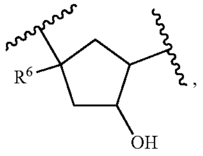, 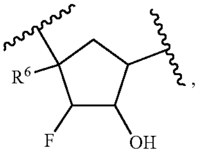,

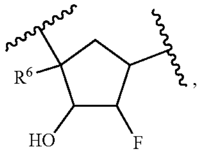, 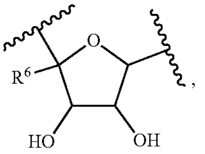,

-continued

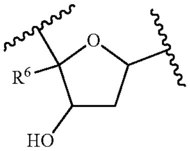, 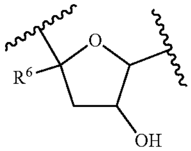,

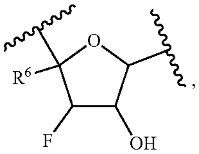, 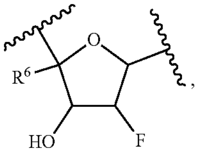, and

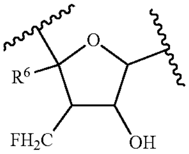.

Alternatively, or in addition, $R^6$ can be CN; cycloalkyl or heterocyclo; haloalkyl; aminoalkyl, cyanoalkyl or amido; or halo or $N_3$. $R^6$ can be H, halo, alkyl (e.g., substituted or unsubstituted ($C_1$-$C_8$)-alkyl), hydroxyalkyl (e.g., ($C_1$-$C_8$)-alkyl-OH), alkoxy (e.g., substituted or unsubstituted ($C_1$-$C_8$)-alkoxy), haloalkyl (which is an example of a substituted alkyl; e.g., fluoromethyl, difluoromethyl, and chloromethyl), cycloalkyl (e.g., substituted or unsubstituted ($C_4$-$C_8$)-cycloalkyl), heterocyclo (e.g., 3-5-membered heterocyclo, such as epoxy, aziridino, oxetananyl, and azetanyl), heterocycloalkyl (e.g., a ($C_1$-$C_8$)-alkyl substituted with a 3-5-membered heterocyclo, such as epoxy, aziridino, oxetananyl, and azetanyl), cyano, cyanoalkyl (another example of substituted alkyl; e.g., substituted or unsubstituted ($C_1$-$C_8$)-alkyl-CN), amino (e.g., $NH_2$), aminoalkyl (e.g., substituted or unsubstituted ($C_1$-$C_8$)-alkyl-$NH_2$, such as $CH_2NH_2$), amido (e.g., $C(O)NR^2$, such as $C(O)NH_2$), amidoalkyl (e.g., substituted or unsubstituted ($C_1$-$C_8$)-alkyl-$C(O)NR^2$) or $N_3$.

In some embodiments, $R^6$ can be H, halo, alkyl, alkenyl, hydroxyalkyl, alkoxy, alkoxyalkyl, haloalkyl, cycloalkyl, heterocyclo, cyano, cyanoalkyl, amino, aminoalkyl, amido, amidoalkyl, $CO_2H$, $CO_2Et$, thioalkyl, $C(S)R^7$, $C(NOR^7)(R^7)$, $C(NR^7)(R^7)$ or $N_3$;

Compounds of the formula (II) are contemplated herein wherein, the groups $R^6$ can be chosen to form various ring systems, including the following ring systems:

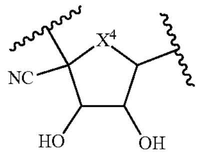, 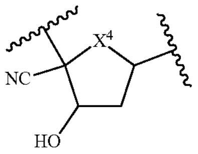,

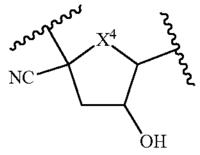, 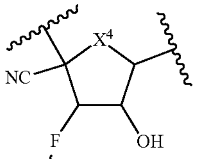,

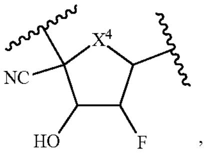, 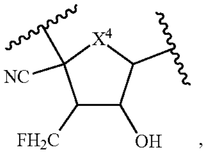, and

-continued

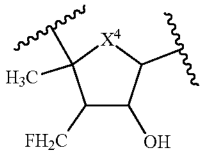

such as:

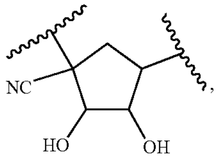, 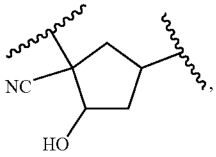,

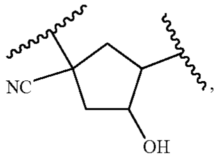, 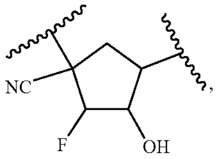,

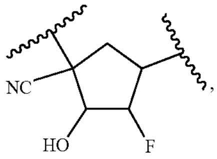, 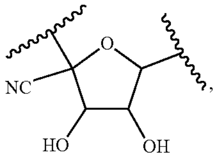,

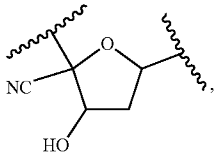, 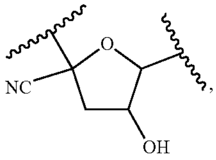,

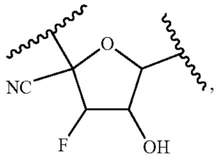, 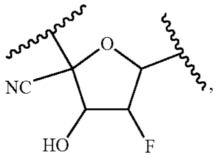,

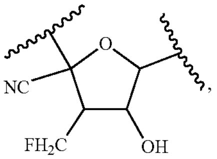, and 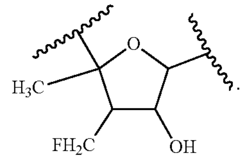.

Or, instead of the CN group depicted in the foregoing structures, Re can be cycloalkyl or heterocyclo; haloalkyl; aminoalkyl, cyanoalkyl or amido; or halo or $N_3$. Thus, for example, $R^6$ can be any suitable substituent, including the following: F, $N_3$, $CH_3$, $CHF_2$, $CF_3$, aminoalkyl (e.g., $CH_2NH_2$), cycloalkyl (e.g., cyclopropyl, cyclobutyl, and cyclopentyl), cyanoalkyl (e.g., $CH_2CN$), amido (e.g., $CONH_2$), and heterocyclyl, such as groups of the formula:

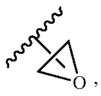, 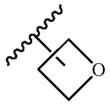, 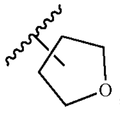,

-continued

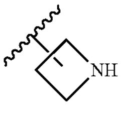

, and

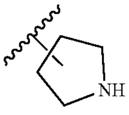

, such as

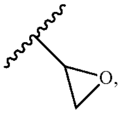

,

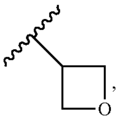

,

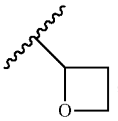

,

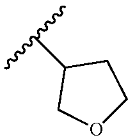

,

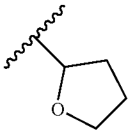

,

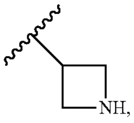

,

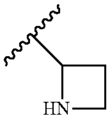

,

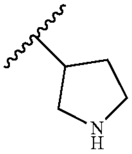

, and

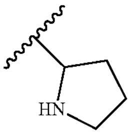

, each of which can be further substituted.

Examples of compounds of the formula (II) include compounds of the formulae:

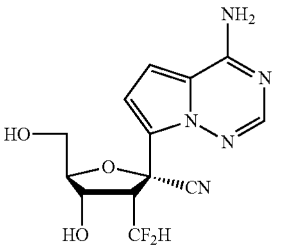

and

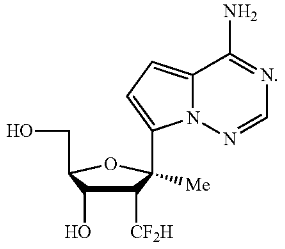

Pharmaceutical compositions are also contemplated herein, comprising one or more compounds of described herein (e.g. a compound of the formula (I) or (II)) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In some cases isotonic agents can be included in the pharmaceutical compositions, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the various embodiments described herein or an appropriate pharmaceutical composition thereof are effective, the compounds of the various embodiments described herein may be administered in an effective amount. The dosages as suitable for this invention may be a composition, a pharmaceutical composition or any other compositions described herein.

The dosage can be administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Compositions comprising a therapeutically effective amount of one or more compounds of the various embodiments described herein (e.g. a compound of the formula (I) or (II)) are also contemplated. The compositions are useful in a method for treating a pulmonary infection caused by an enveloped virus, the method comprising administering one or more compounds described herein (e.g., a compound of formula (I) or (II)) to a subject in need of treatment for the infection. Also contemplated herein is one or more compounds described herein for use as a medicament for treating a patient in need of relief from a pulmonary infection caused by an enveloped virus. As discussed herein, examples of enveloped viruses include, but are not limited to, SARS-COV, MERS-COV, and SARS-COV-2.

The term "therapeutically effective amount" as used herein, refers to that amount of one or more compounds of the various embodiments described herein (e.g. a compound of the formula (I) or (II)) that elicits a biological or medicinal response in a tissue system, animal or human, that is being sought by a researcher, veterinarian, medical doctor or other clinician, which includes alleviation of the symptoms of the disease or disorder being treated (e.g., a pulmonary infection caused by an enveloped virus). The therapeutically effective amount can be that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "substituted," "substituent," and "functional group," as used herein refers to a group that can be or is substituted onto a molecule or onto another group (e.g., on an aryl or an alkyl group). Examples of substituents include, but are not limited to, a halogen (e.g., F, Cl, Br, and I), OR, $OC(O)N(R)_2$, CN, NO, $NO_2$, $ONO_2$, azido, $CF_3$, $OCF_3$, R, O (oxo), S (thiono), C(O), S(O), methylenedioxy, ethylenedioxy, $N(R)_2$, SR, SOR, $SO_2R$, $SO_2N(R)_2$, $SO_3R$, $-(CH_2)_{0-2}P(O)(OR)_2$, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{0-2}N(R)C(O)R$, $(CH_2)_{0-2}N(R)C(O)OR$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, $C(=NH)N(R)_2$, C(O)N(OR)R, or C(=NOR)R wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl, which can be mono- or independently multi-substituted.

The term "alkyl" as used herein refers to substituted or unsubstituted straight chain and branched mono- or divalent alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched mono- or divalent alkenyl groups and cycloalkenyl groups having at least one double bond and having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkenyl groups include those with from 1 to 8 carbon atoms such as $-CH=CH-$, $-CH=CHCH_3$, and $-CH_2CH=CHCH_2-$ groups, wherein the double bonds can have an E- or Z-configuration. And when there are multiple bonds, each double bond can, independently, have an E- or a Z-configuration. Examples of branched alkenyl groups include, but are not limited to, $-CH=C(CH_3)-$ and $CH_2C{=}CH(CH_3)$ groups. Representative substituted alkenyl groups can be substituted one or more times with any of the groups listed herein, for example, amino, hydroxy, cyano, carboxy, nitro, thio, alkoxy, and halogen groups.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups can have any number of carbon atoms, e.g., 3 to 8 carbon atoms ($C_3$-$C_8$), 3 to 6 carbon atoms ($C_3$-$C_6$), and 4 to 8 carbon atoms ($C_4$-$C_8$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" or "heterocyclo" as used herein refers to substituted or unsubstituted aromatic and non-aromatic ring compounds containing 3 or more ring members, of which, one or more (e.g., 1, 2 or 3) is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups. Examples of indolinonyl groups include groups having the general formula:

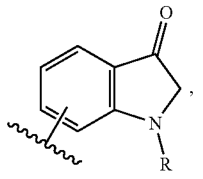

wherein R is as defined herein.

Examples of isoindolinonyl groups include groups having the general formula:

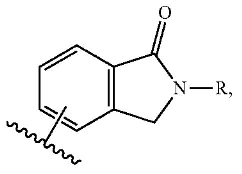

wherein R is as defined herein.

Examples of benzoxazolinyl groups include groups having the general formula:

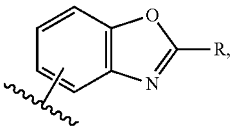

wherein R is as defined herein.

Examples of benzthiazolinyl groups include groups having the general formula:

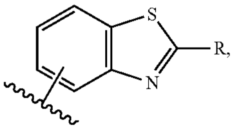

wherein R is as defined herein.

In some embodiments, the group R in benzoxazolinyl and benzthiazolinyl groups is an $N(R)_2$ group. In some embodiments, each R is hydrogen or alkyl, wherein the alkyl group is substituted or unsubstituted. In some embodiments, the alkyl group is substituted with a heterocyclyl group (e.g., with a pyrrolidinyl group).

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heterocyclylalkoxy" as used herein refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkoxy groups include, but are not limited to, $—O—(CH_2)_q$ heterocyclyl, wherein q is an integer from 1 to 5. In some embodiments, heterocyclylalkoxy groups include $—O—(CH_2)_q$morpholinyl such as $—O—CH_2CH_2$-morpholine.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "amine," "amine group," "amino," and "amino group" as used herein refer to a substituent of the form $—NH_2$, —NHR, $—NR^2$, $—NR_3^+$, wherein each R is defined herein, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group.

An "alkylamino" group includes a monoalkylamino, dialkylamino, and trialkylamino group. An example of a "alkylamino" is —NH-alkyl and $—N(alkyl)_2$.

An example of a "cycloalkylamino" group is —NH-cycloalkyl and $—N(cycloalkyl)_2$.

An example of a "cycloalkyl heterocycloamino" group is —NH-(heterocyclo cycloalkyl), wherein the heterocyclo group is attached to the nitrogen and the cycloalkyl group is attached to the heterocyclo group.

An example of a "heterocyclo cycloamino" group is —NH-(cycloalkyl heterocycle), wherein the cycloalkyl group is attached to the nitrogen and the heterocyclo group is attached to the cycloalkyl group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, $—CF(CH_3)_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Those skilled in the art will appreciate that many modifications to the embodiments described herein are possible without departing from the spirit and scope of the present disclosure. Thus, the description is not intended and should not be construed to be limited to the examples given but should be granted the full breadth of protection afforded by the appended claims and equivalents thereto. In addition, it is possible to use some of the features of the present disclosure without the corresponding use of other features. Accordingly, the foregoing description of or illustrative embodiments is provided for the purpose of illustrating the principles of the present disclosure and not in limitation thereof and can include modification thereto and permutations thereof.

EXAMPLES

The disclosure can be better understood by reference to the following examples which are offered by way of illustration. The disclosure is not limited to the examples given herein.

General

C-nucleosides contain a C—C bond between the ribofuranose and the nucleobase, which increases the stability and allows ready introduction of substituents at the 1'-position. Scheme 1-11 show the synthesis of C-nucleosides analogs 1-14.

Scheme 1.
Structure of synthesized C-Nucleoside.

1-14

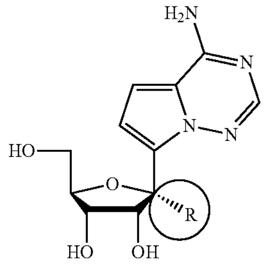

1

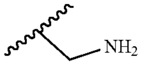

-continued

2

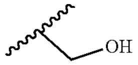

3

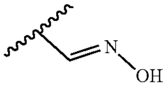

4

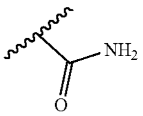

5

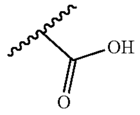

6

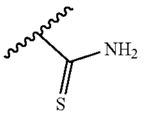

7

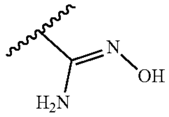

8

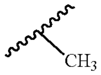

9

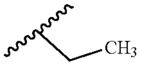

10

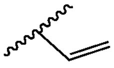

11

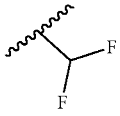

12

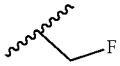

13

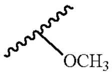

14

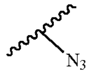

Scheme 2. Synthesis of compound 1.
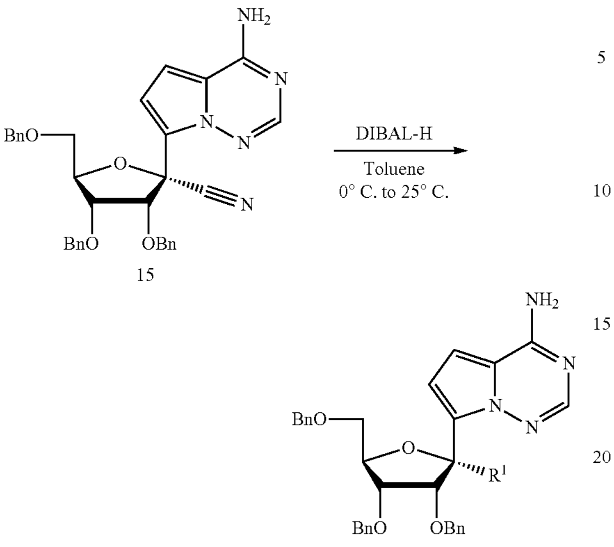
15
16: $R^1$ = CHO, 48%
17: $R^1$ = $CH_2NH_2$, 41%
-continued
17
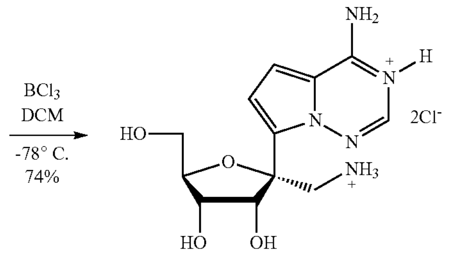
1
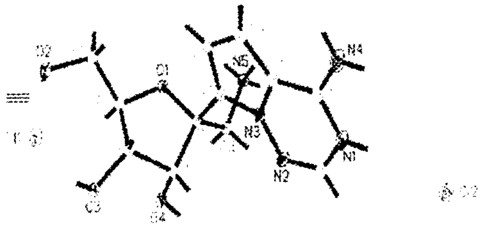
X-ray structure of 1
Scheme 3.
Synthesis of compound 2-3.
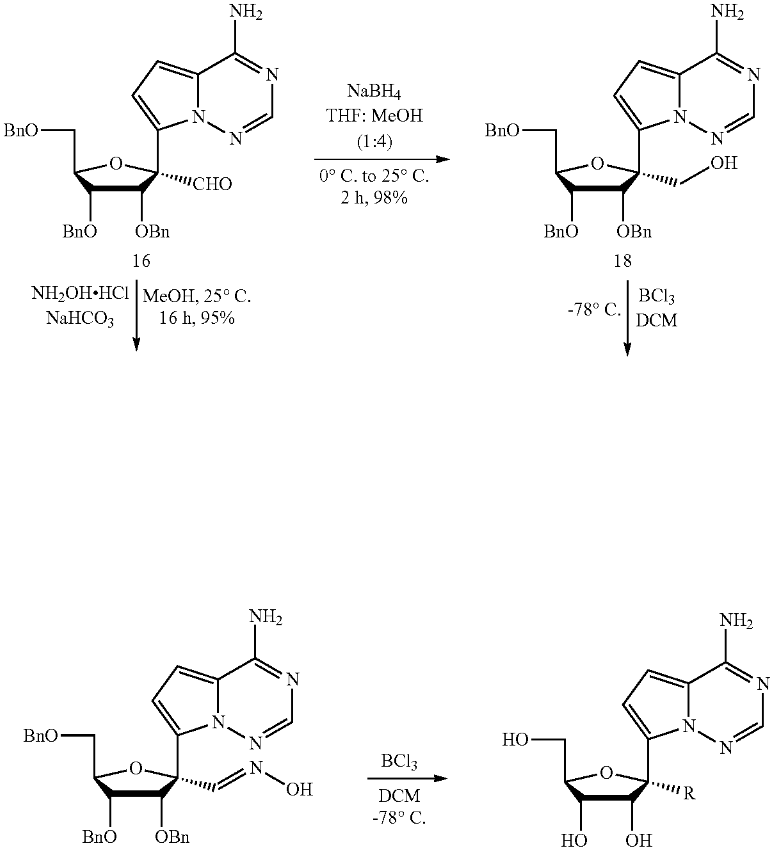
16
18
19
2: R = $CH_2OH$, 78%
3: R = CH═N—OH, 70%

Scheme 4. Synthesis of compound 4-7.
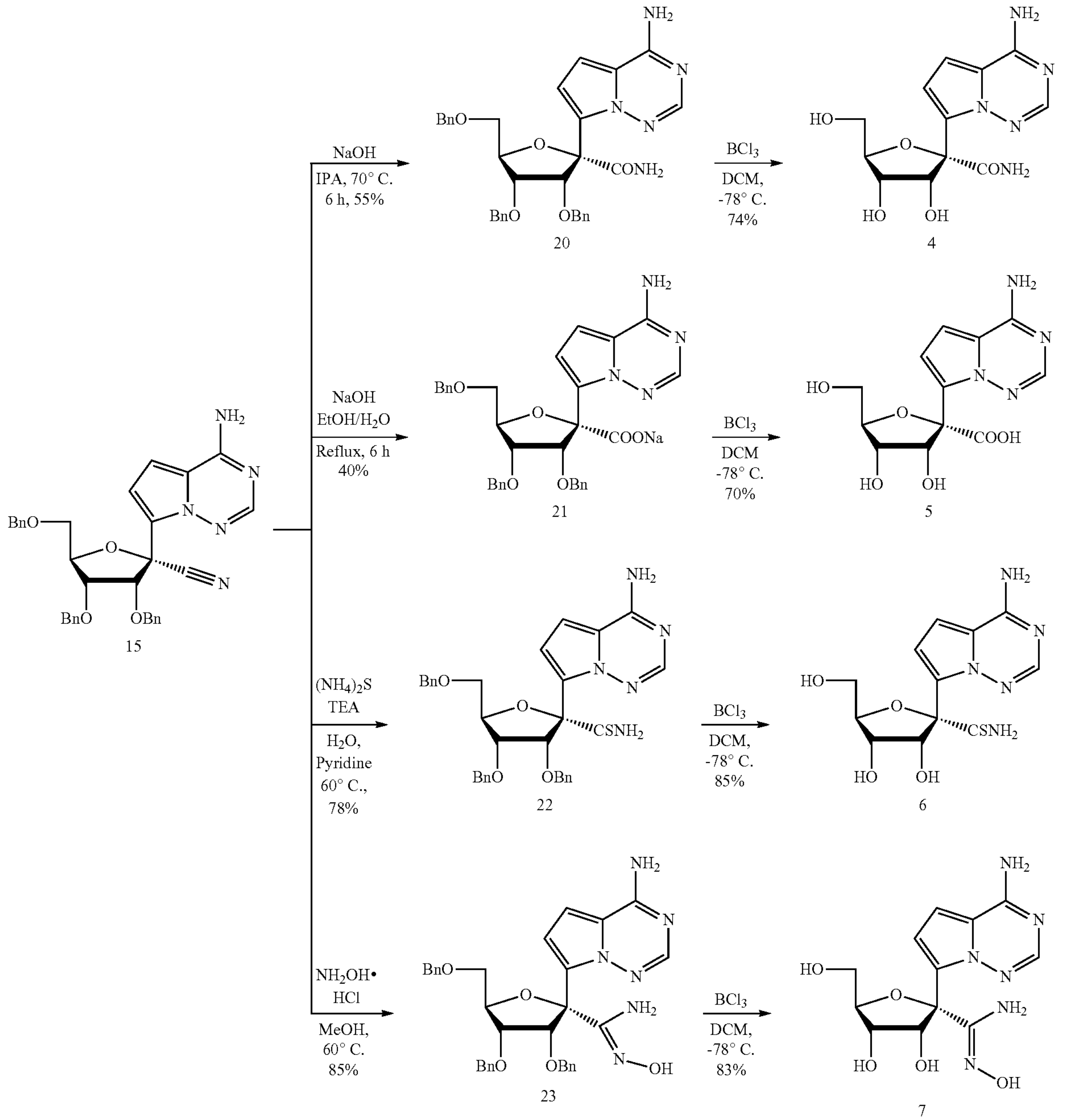
15, 20, 4, 21, 5, 22, 6, 23, 7
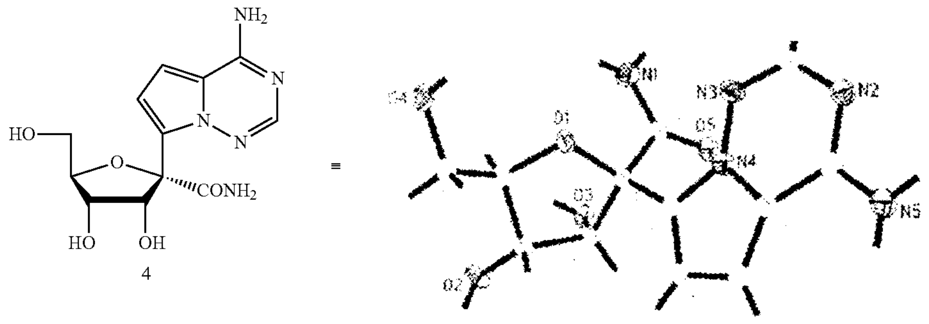
4
X-ray structure of 4

Scheme 5.
(A) Synthesis of compound 8-10 and (B) Synthesis of compound 33.
A.
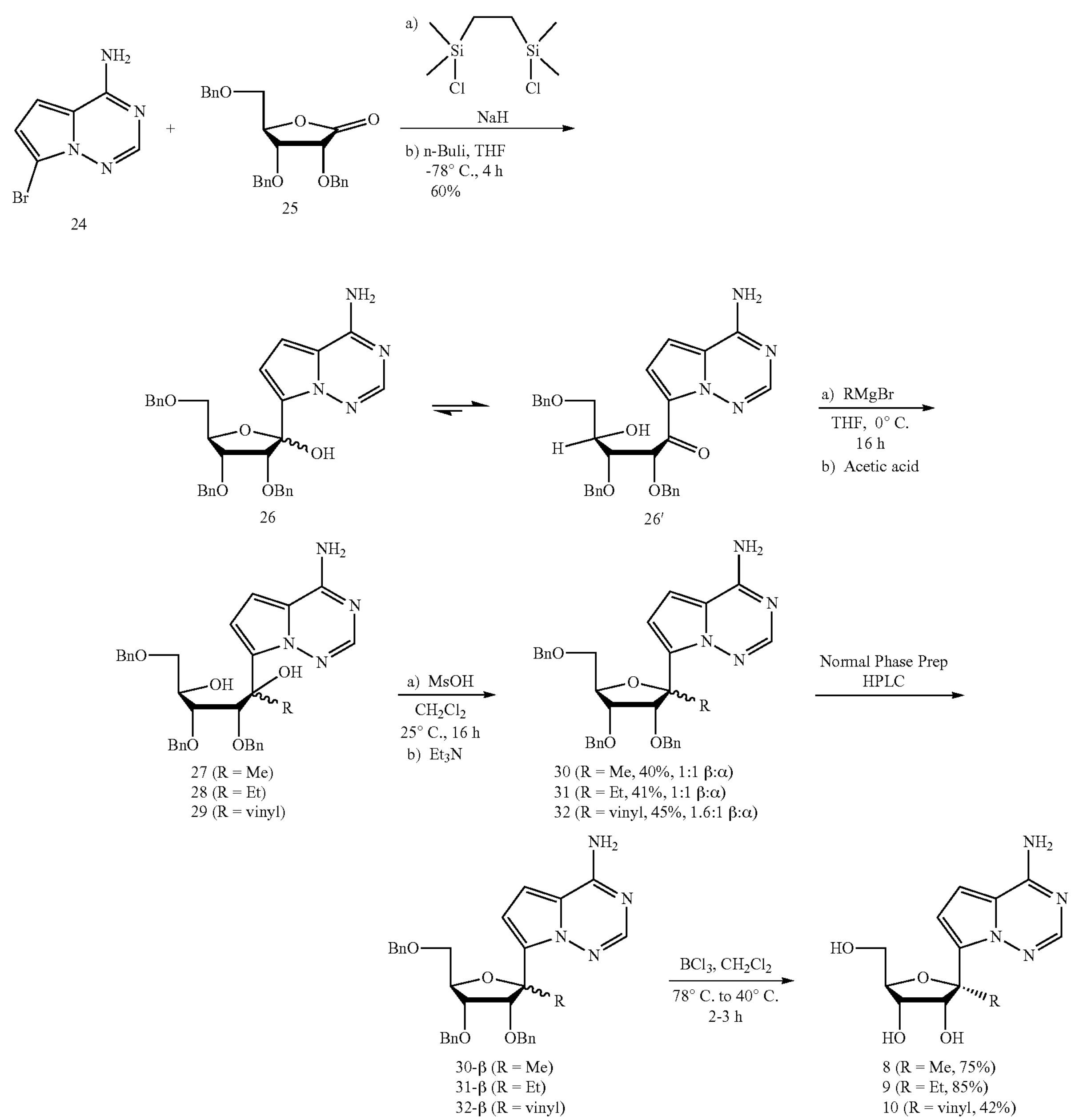
B.
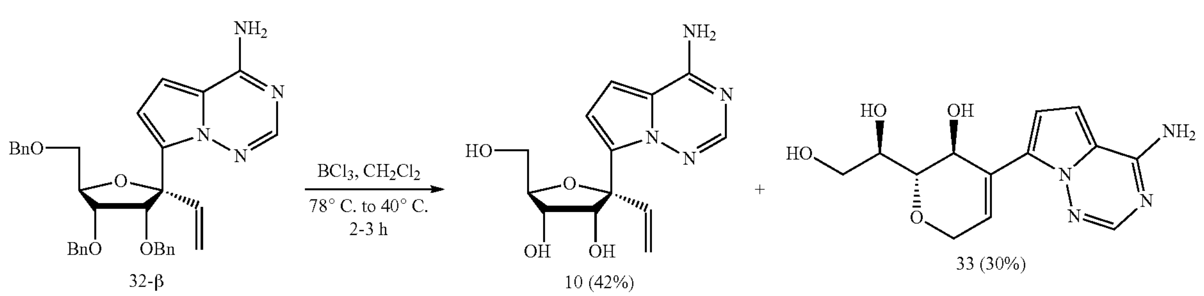

Scheme 6.
(A) Synthesis of the 1′- Difluoromethyl Diol Analogue 38,
(B) MsOH-Mediated Cyclization and Debenzyalation of 38a, and
(C) MsOH-Mediated Cyclization and Debenzyalation of 38b.
A.
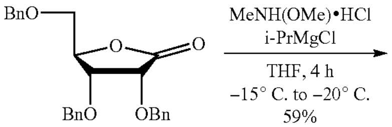
25
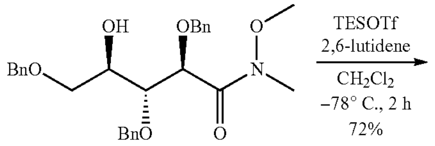
34
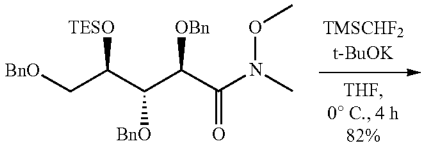
35
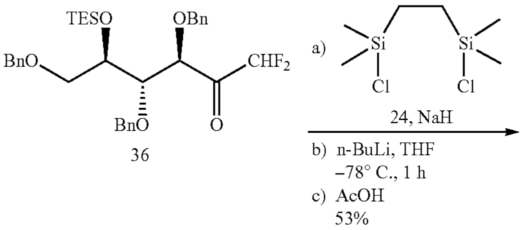
36
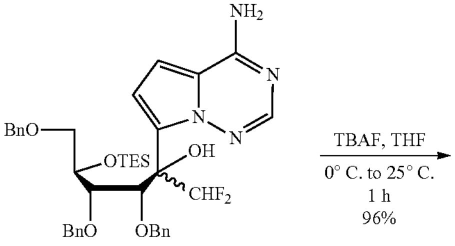
37a/b,
(1.2:1 isomeric mixture)
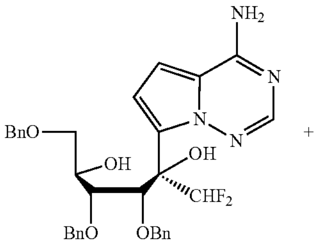
38a,
major
-continued
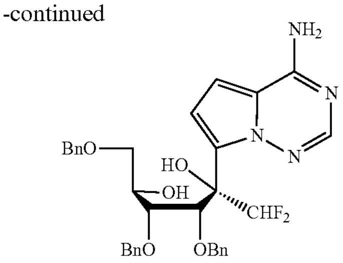
38b,
minor
B.
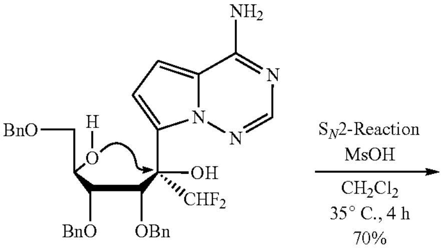
38a
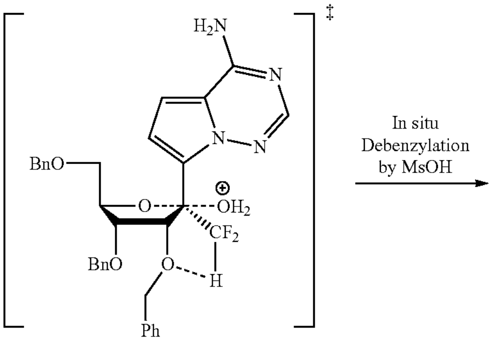
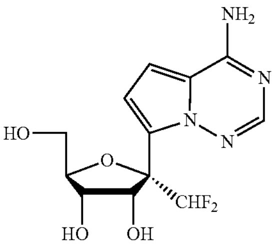
11β
C.
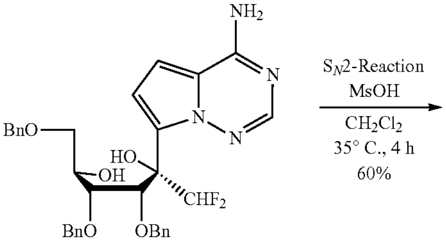
38b -continued
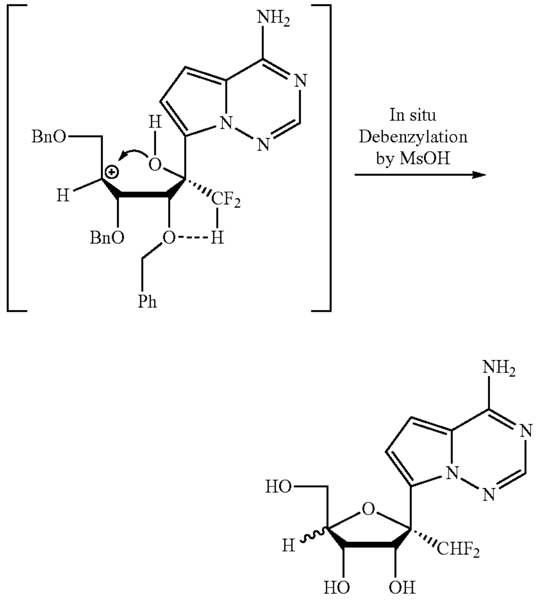
1:1 mixture of
11β: 4'-epi-11β
Scheme 7.
(A) Synthesis of the 1'-Difluoromethyl Diol Analogue 41,
(B) MsOH-Mediated Cyclization and Debenzyalation of 41a, and
(C) MsOH-Mediated Cyclization and Debenzyalation of 41b.
A.
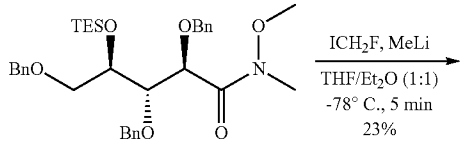
35
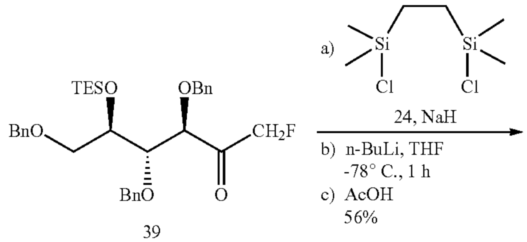
39
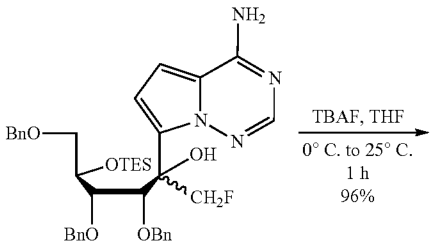
40
(1.2:1 isomeric mixture)
-continued
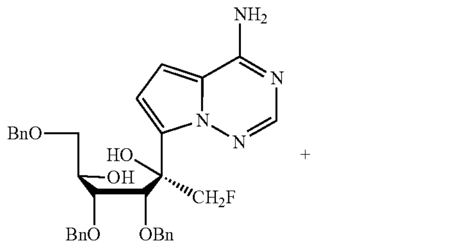
41a, major
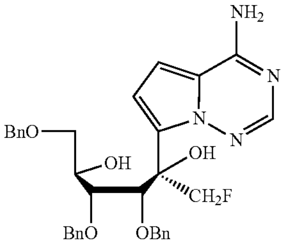
41b, minor
B.
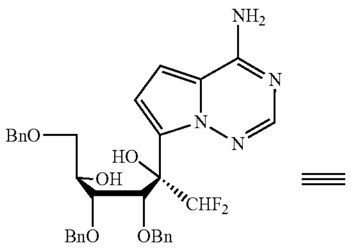
41a
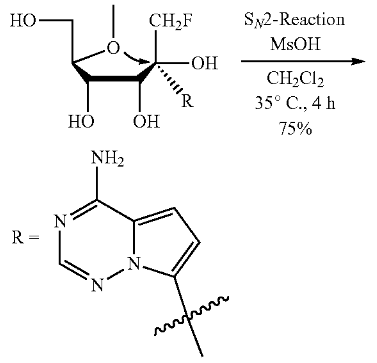
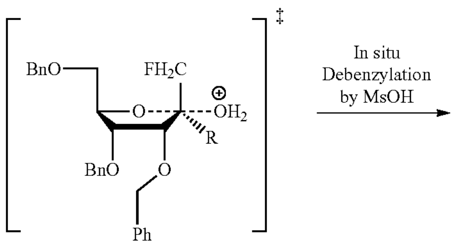

-continued
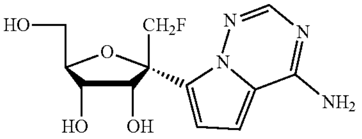
12α
C.
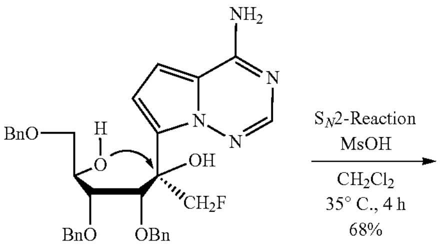
41b
-continued
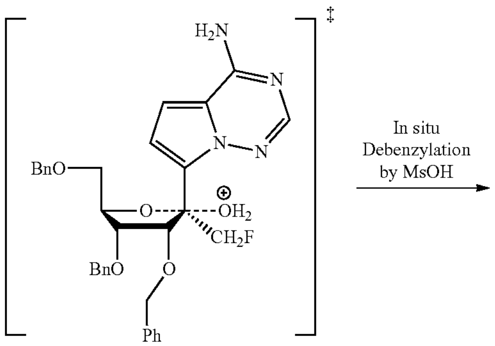
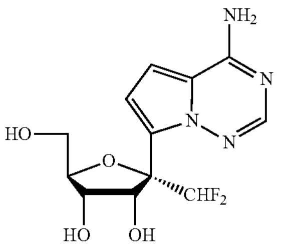
12β
Scheme 8.
Synthesis of compound 42.
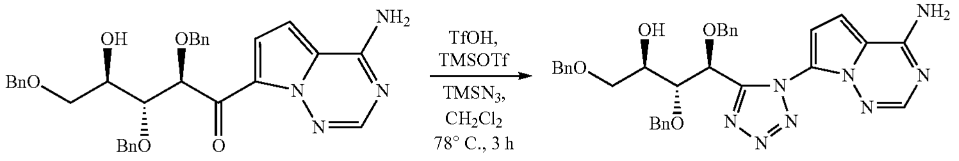
26′
42
Mechanism:
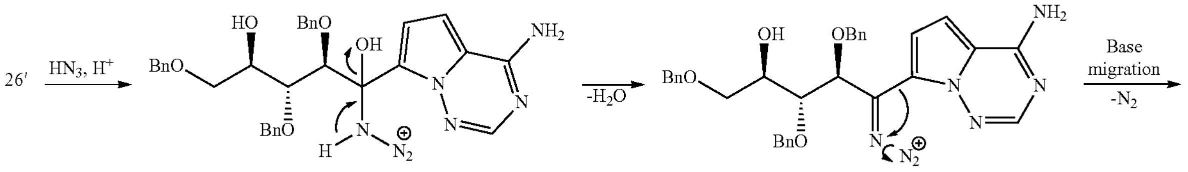
Azidohydrin
43
Diazoiminium ion
44
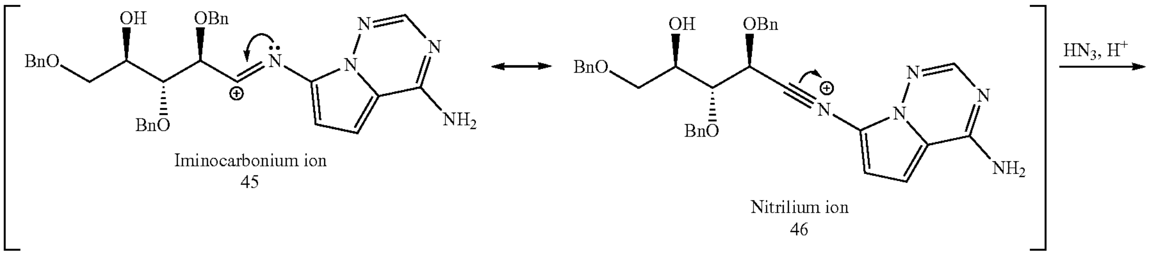
Iminocarbonium ion
45
Nitrilium ion
46

-continued
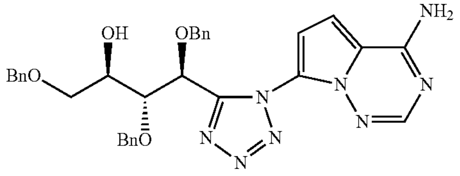
Tetrazole
47
Scheme 9. Synthesis of compound 13.
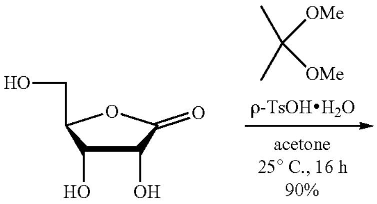
48
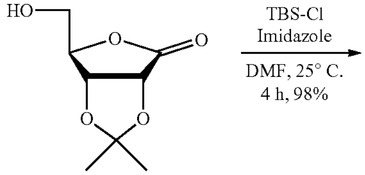
49
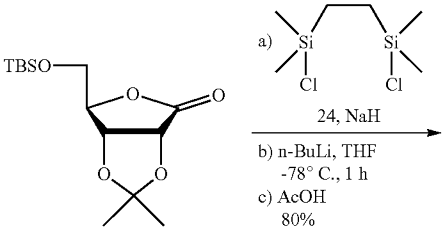
50
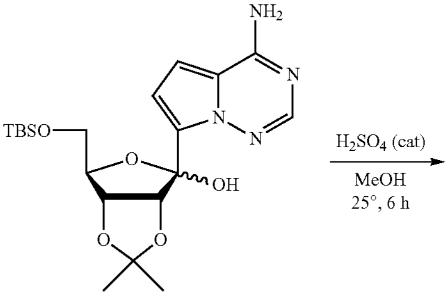
51
-continued
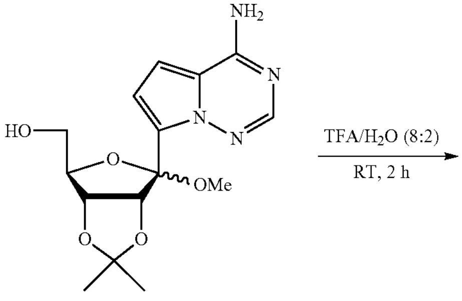
52
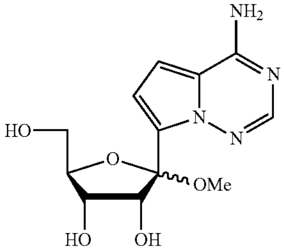
13
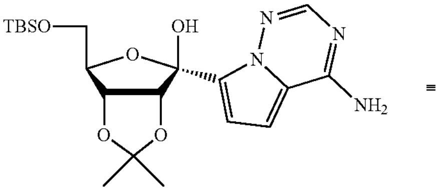
51 (α)
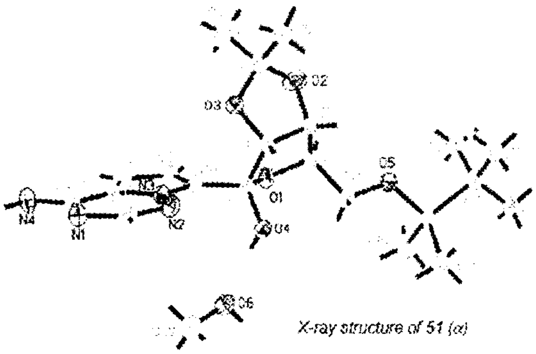
X-ray structure of 51 (α)

Scheme 10.
Synthesis of compound 56.
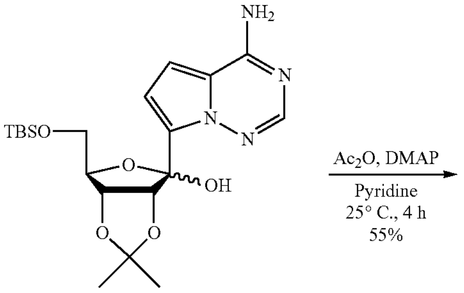
51
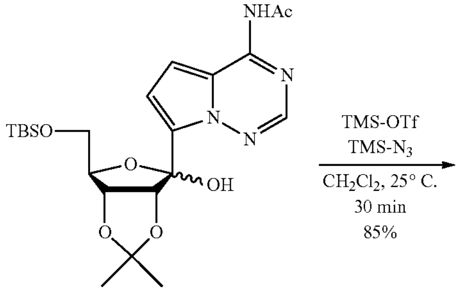
53
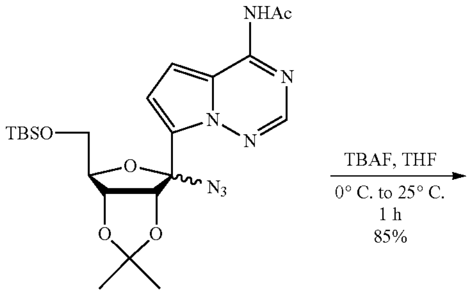
54
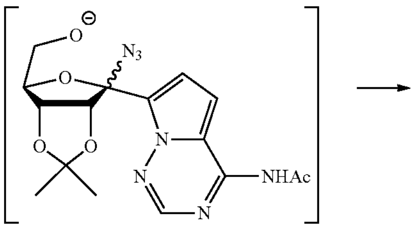
55
-continued
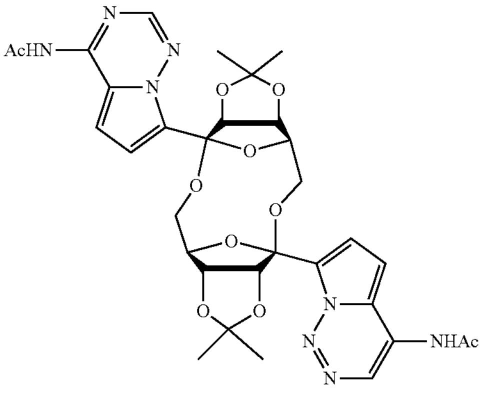
56
Scheme 11.
Synthesis of compound 14.
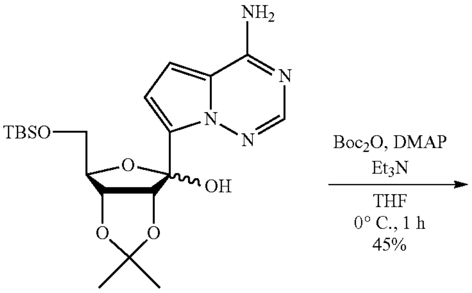
51
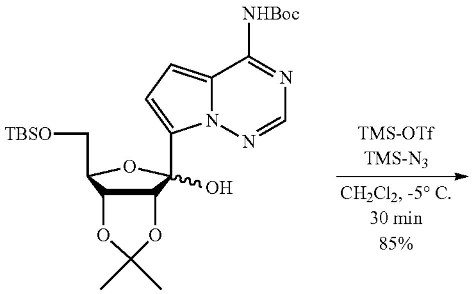
57
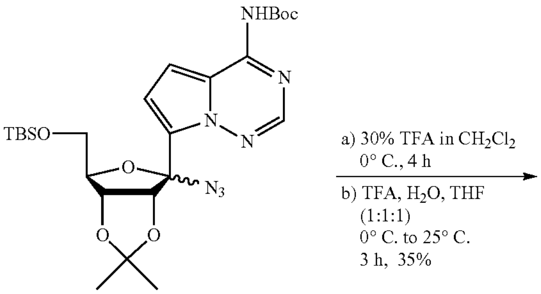
58

-continued

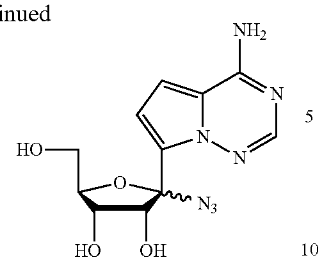

14

General Chemistry Methods. All commercial reagents were used as provided unless otherwise indicated. An anhydrous solvent dispensing system using packed columns of neutral alumina was used for drying THF and $CH_2Cl_2$, while packed columns of 4 Å molecular sieves were used to dry DMF, and the solvents were dispensed under nitrogen. All reactions were performed under an inert atmosphere of argon in oven dried (130-150° C.) glassware. Thin-layer chromatography was performed on a pre-coated silica gel 60 $F_{254}$ plates. The detection of compounds was carried out with UV light. Purification by flash chromatography was performed using a medium-pressure flash chromatography system and flash column silica cartridges with the indicated solvent system. HPLC purifications were performed on instrument equipped with normal-phase waters 5 μm (column description) and for reverse-phase, Phenomenex Gemini 10 μm C18 110 Å (250×21.2 mm) column. All NMR spectra were recorded on a 600 and 400 MHz spectrometer at 600 and 400 MHz for $^1H$, 125 and 100 MHz for $^{13}C$, and 376 MHz for $^{19}F$. $^1H$ NMR spectra were referenced to residual $CDCl_3$ (7.27 ppm), DMSO-$d_6$ (2.50 ppm), or $CD_3OD$ (3.31 ppm); $^{13}C$ NMR spectra were referenced to $CDCl_3$ (77.23 ppm) DMSO-$D_6$ (39.51 ppm), or $CD_3OD$ (49.15 ppm); and $^{19}F$ NMR spectra were referenced to hexafluorobenzene (−162.9 ppm)[i] or trifluoroacetic acid (−76.5 ppm). NMR chemical shift data are reported as follows: chemical shift, multiplicity (br=broad, s=singlet, d=doublet, t=triplet, q=quartet, m=multiplet, ABq=AB quartet, dm=doublet of multiplets), coupling constant, integration. Coupling constants are given in Hertz (Hz). $^1H$ and $^{13}C$ NMR peak assignments were based on gCOSY and gHMQC NMR spectra, respectively. $^{19}F$ NMR peaks were assigned using proton-fluorine coupling constants. High-resolution mass spectra (HRMS) were obtained on a TOF instrument.

General Procedure 1: Boron Trichloride-Mediated Benzyl Deprotection.

To a suspension of 2',3',5'-O-tribenzyl ribono-nucleoside of choice (1.00 mmol, 1.00 equiv) in $CH_2Cl_2$ (5.00 mL) at −78° C., 1.00 M $BCl_3$ in $CH_2Cl_2$ (3.80 mmol, 3.80 equiv) was slowly added down the side of the flask and the reaction mixture was stirred for 5 minutes. Then the reaction temperature was warmed to −40° C. and stirred additional 2 h. When TLC indicated the complete consumption of starting material, the reaction mixture was quenched with MeOH (0.50 mL) followed by water (0.50 mL). Thereafter, the reaction mixture was warmed to room temperature and the volatiles were removed by evaporation under reduced pressure. The crude reaction mixture was washed with hexane and purified by silica gel flash column chromatography (dry loading, $SiO_2$, MeOH/EtOAc gradient) to afford the benzyl deprotected nucleoside.

General Procedure 2: Grignard Addition and Acid-Mediated Cyclization.

The hydroxyketone 26 (1.00 mmol, 1.00 equiv) was dissolved in anhydrous THF and cooled to 0° C. with stirring under inert atmosphere. A solution of respective Grignard reagent (8.00 mmol, 8.00 equiv) was added and the resultant mixture was stirred at 0° C. for 16 h. The reaction mixture was quenched by addition of acetic acid (8.00 mmol, 8.00 equiv) and the solvent was evaporated under reduced pressure. The residue was dissolved in EtOAc and the organic layer was washed with water, brine and dried over anhydrous $Na_2SO_4$. The solvent was evaporated to dryness and the crude material was dissolved in anhydrous dichloromethane. Then, methanesulfonic acid (4.00 mmol, 4.00 equiv) was added and the reaction mixture was stirred for 16 h at room temperature. After the completion of reaction as indicated by TLC, the reaction mixture was quenched by the addition of triethylamine (4.00 mmol, 4.00 equiv). The reaction mixture was concentrated under reduced pressure and the residue was purified by silica gel chromatography to afford the desired product.

Synthesis of 4-Amino-7-(1'-hydroxy-2',3',5'-O-tribenzyl-α/β-D-ribofuranosyl) pyrrolo[2,1-f][1,2,4] triazine (26)

To a suspension of 24 (2.13 g, 10.0 mmol, 1.00 equiv) in THF (40 mL) at 25° C. was added 1,1,4,4-tetramethyl-1,4-dichlorodisilyethylene (2.37 g, 11.0 mmol, 1.10 equiv) along with sodium hydride (0.88 g, 22.0 mmol, 2.20 equiv) and the mixture was stirred for 30 min. The reaction mixture was then cooled to −78° C. and n-BuLi (20.6 mL, 33.0 mmol, 1.6 M in hexane) was slowly added down the side of the flask over 15

26

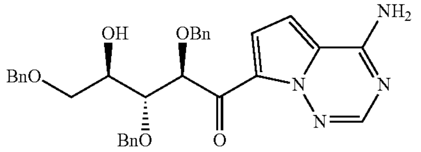

min. The reaction was stirred at −78° C. for a further 15 min, then a solution of ribonolactone 25 (4.60 g, 11.0 mmol, 1.10 equiv) in THF (15 mL) was added dropwise down the side of the flask. After 2 h when TLC indicated complete consumption starting materials, the reaction mixture was quenched with glacial acetic acid (1.2 mL, 20.0 mmol, 2.00 equiv) at −78° C. and stirred for 10 min, warmed to 25° C. and concentrated under reduced pressure. The residue was partitioned between $CH_2Cl_2$ and $H_2O$ (300 mL, 1:1) and the organic layer was dried ($MgSO_4$), filtered and concentrated under reduced pressure. Purification by silica gel flash chromatography (0-45% EtOAc/hexane) afforded pure open-chain hydroxyketone 11' (3.31 g, 60%) as an amorphous white solid. Rt=0.30 (60% EtOAc/hexane); $^1H$ NMR (600 MHz, $CD_3OD$) δ 7.89 (s, 1H), 7.31-7.24 (m, 11H), 7.09-7.05 (m, 3H), 6.94-6.90 (m, 2H), 6.81 (d, J=4.9 Hz, 1H), 5.34 (d, J=6.5 Hz, 1H), 4.59 (dd, J=7.7, 4.2 Hz, 3H), 4.46 (d, J=19.5 Hz, 5H), 4.18 (dt, J=6.3, 4.1 Hz, 1H), 4.01 (dd, J=6.5, 4.4 Hz, 1H), 3.73 (dd, J=10.0, 4.0 Hz, 1H), 3.59 (dd, J=10.0, 6.3 Hz, 1H); $^{13}C$ NMR (150 MHz, $CD_3OD$) đ 191.2, 157.4, 149.6, 139.7, 139.3, 138.9, 130.0, 129.4, 129.4, 129.3, 129.3, 129.1, 129.0, 128.9, 128.9, 128.8, 128.6, 128.5, 128.2, 120.3, 119.8, 103.6, 83.0, 82.2, 74.4, 74.2, 73.4, 72.4, 71.5; FTIR ($cm^{-1}$) 3332, 3215, 2974, 2868, 1638, 1599, 1455, 1269, 1088; HRMS (ESI-TOF) m/z:

$[M+H]^+$ calcd for $C_{32}H_{33}N_4O_5$ 553.2451; found 553.2467. The 1H and 13C NMR in DMSO-$d_6$ matched the reported data.

Synthesis of 4-Amino-7-(1'-cyano-2',3',5'-O-tribenzyl-β-D-ribofuranosyl)pyrolo[2,1-f][1,2,4]triazine (15)

To a suspension of 26 (1.64 g, 2.97 mmol, 1.00 equiv) in $CH_2Cl_2$ (30.0 mL) under nitrogen atmosphere at −78° C. was added TfOH (0.53 mL, 5.94 mmol, 2.00 equiv) and the mixture was stirred for 10 min. Next, TMSOTf (1.13 mL, 6.24 mmol, 2.10 equiv) was slowly added down the side of the flask and the reaction was stirred for an additional 30 minutes at −78° C. Thereafter, TMSCN (1.50 mL, 11.9 mmol, 4.00 equiv) was added dropwise and the reaction mixture was stirred for 2 h at −78° C. When TLC indicated the complete consumption of compound 26, the reaction was

15

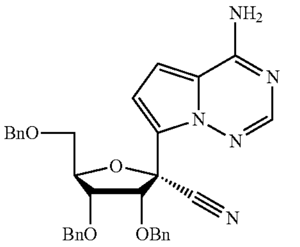

quenched with $Et_3N$ (1.50 mL) and warmed to room temperature. Solid $NaHCO_3$ (2.00 g) was added followed by slow addition of $H_2O$ (10.0 mL) and the reaction stirred for 10 min. The organic layer was separated, dried ($Na_2SO_4$), filtered and concentrated under reduced pressure. Purification by silica gel flash chromatography (30-100% EtOAc/hexane) provided the title compound 15 (1.32 g, 79%) as a white solid of a pure β-anomers. $R_f$=0.30 (50% EtOAc/Hexane); $^1H$ NMR (400 MHz, $CD_3OD$) δ 7.65 (s, 1H), 7.31-7.17 (m, 15H), 6.83 (d, J=8.5 Hz, 2H), 4.94 (d, J=5.1 Hz, 1H), 4.78-4.68 (m, 2H), 4.58-4.55 (m, 1H), 4.50-4.44 (m, 4H), 4.11 (t, J=5.3 Hz, 1H), 3.75-3.70 (m, 1H), 3.63-3.58 (m, 1H); $^{13}C$ NMR (101 MHz, $CD_3OD$) δ 157.1, 147.9, 139.4, 139.1, 138.4, 129.5, 129.3, 129.3, 129.1, 129.1, 128.9, 128.8, 128.8, 128.6, 124.7, 118.1, 118.0, 113.0, 102.3, 83.8, 79.9, 79.8, 77.6, 74.2, 74.1, 73.3, 69.8. FTIR ($cm^{-1}$): 3397, 3032, 2924, 1660, 1602, 1026; HRMS (ESI+) m/z calcd for $C_{33}H_{31}N_5O_4$ [M+H]' 562.2454, found 562.2462.

Synthesis of 4-Amino-7-(1'-formyl-2',3',5'-O-tribenzyl-β-D-ribofuranosyl)pyrolo[2,1-f][1,2,4]triazine (16) and 4-Amino-7-(1'-aminomethyl-2',3',5'-O-tribenzyl-8-D ribofuranosyl)pyrolo[2,1-f][1,2,4] triazine (17)

Compounds 16 and 17 were prepared form 15 via DIBAL-H reduction. To a solution of 15 (1.07 g, 1.90 mmol, 1.00 equiv) in toluene (40 mL) was added 1.00 M solution in DIBAL-H in toluene (5.70 mL, 5.70 mmol, 3.00 equiv) at 0° C. under an argon atmosphere. Then the reaction mixture was slowly warmed to room temperature and kept at room temperature for 6 h. After 8 h, the TLC of the reaction mixture indicated the completion of reaction. The reaction mixture was then added to 2 M AcOH (100 mL) and extracted with ethyl acetate (2×50 mL). The combined

16

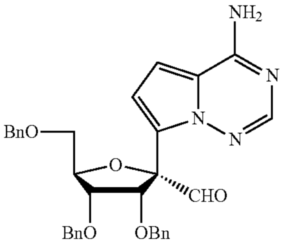

and

17

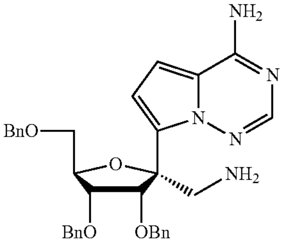

organic layers were dried using anhydrous $MgSO_4$ and concentrated. The residue was purified by flash chromatography eluting with 0-60% EtOAc in hexane to provide 16 (0.51 g, 48%) as an amorphous white solid, while increasing polarity to 20% MeOH in EtOAc afforded 17 (0.43 g, 41%).

Data for 16. $R_f$=0.48 (20% EtOAc/DCM); $^1H$ NMR (400 MHz, $CDCl_3$) δ 10.10 (s, 1H), 7.87 (s, 1H), 7.33-7.25 (m, 13H), 7.17 (dd, J=7.3, 2.3 Hz, 2H), 6.61 (d, J=4.6 Hz, 1H), 6.49 (d, J=4.6 Hz, 1H), 5.47 (s, 2H, —$NH_2$), 5.02 (d, J=4.4 Hz, 1H), 4.80-4.66 (m, 2H), 4.63-4.57 (m, 1H), 4.56-4.47 (m, 2H), 4.46-4.41 (m, 2H), 4.15 (dd, J=5.6, 4.4 Hz, 1H), 3.73-3.58 (m, 2H); $^{13}C$ NMR (100 MHz, $CDCl_3$) δ 197.8, 155.2, 147.1, 138.2, 137.8, 137.5, 128.55, 128.51, 128.4, 128.2, 128.0, 127.98, 127.93, 127.8, 127.67, 127.62, 115.3, 111.5, 99.9, 86.8, 81.8, 81.3, 78.0, 73.4, 73.4, 72.6, 69.4; HRMS (ESI+) calcd for $C_{33}H_{33}N_4O_5$ $[M+H]^+$ 565.2445, found 565.2447.

Data for 17. $R_f$=0.15 (20% MeOH/EtOAc); $^1H$ NMR (400 MHz, $CD_3OD$) δ 7.76 (s, 1H), 7.45-7.37 (m, 2H), 7.35-7.20 (m, 13H), 6.85-6.75 (m, 2H), 4.83-4.71 (m, 2H), 4.68 (d, J=4.6 Hz, 1H), 4.52-4.43 (m, 4H), 4.42-4.36 (m, 1H), 4.04 (dd, J=6.8, 4.6 Hz, 1H), 3.79-3.57 (m, 4H); $^{13}C$ NMR (100 MHz, $CD_3OD$) δ 157.2, 148.0, 139.3, 139.1, 138.9, 130.7, 129.6, 129.48, 129.44, 129.3, 129.2, 129.09, 129.03, 128.8, 128.7, 117.0, 112.4, 102.6, 84.6, 82.1, 81.4, 79.6, 74.9, 74.3, 73.7, 70.9, 43.8; HRMS (ESI+) calcd for $C_{33}H_{35}N_5O_4$ $[M+H]^+$ 566.2762, found 566.2780.

Synthesis of 4-Amino-7-(1'-aminomethyl-2',3',5'-trihydroxy-β-D-ribofuranosyl)pyrolo[2,1-f][1,2,4] triazine (1)

The title compound was prepared from compound 17 (56 mg, 0.10 mmol, 1.00 equiv) using general procedure 1 to afford compound 1 (23 mg, 78%) as a white solid. $R_f$=0.13 (EtOAc:MeOH:$H_2O$:HCOOH=75:20:4:1); $^1H$ NMR (400 MHz, $CD_3OD$) δ 8.11 (s, 1H), 7.44 (d, J=4.7 Hz, 1H), 7.18 (d, J=4.7 Hz, 1H), 4.62 (d,

1

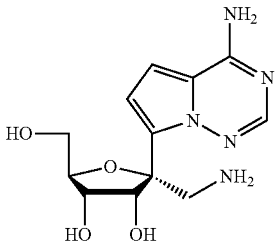

J=4.7 Hz, 1H), 4.13 (ddd, J=8.1, 5.4, 2.8 Hz, 1H), 3.98 (dd, J=8.0, 4.7 Hz, 1H), 3.93-3.87 (m, 2H), 3.73 (dd, J=12.2, 5.4 Hz, 1H), 3.52 (d, J=13.3 Hz, 1H); $^{13}C$ NMR 109.5, 82.0, 82.0, 75.1, 70.7, 61.5, 41.9; HRMS (ESI+) calcd for $C_{12}H_{18}N_5O_4$ $[M+H]^+$ 296.1353, found 296.1345.

Synthesis of 4-Amino-7-(1'-hydroxymethyl-2',3',5'-O-tribenzyl-β-D ribofuranosyl)pyrolo[2,1-f][1,2,4] triazine (18)

To a solution of compound 16 (0.10 g, 0.18 mmol, 1.00 equiv) in THF and MeOH (1:4) (10.0 mL) was added $NaBH_4$ (20 mg, 0.54 mmol, 3.00 equiv) at 0° C. Then the reaction mixture was warmed to 25° C. and stirred for 30 min. The reaction mixture was then diluted with water (30.0 mL) and extracted with $CHCl_3$ (3×30 mL). The combined extracts were dried and concentrated to give a residue, which

18

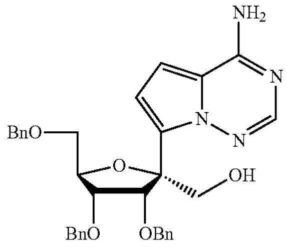

was purified by flash chromatography eluting with 0-80% EtOAc in hexane to provide 18 (88 mg, 98%) as white amorphous solid. $R_f$=0.39 (20% EtOAc/DCM); $^1H$ NMR (400 MHz, $CDCl_3$) δ 7.79 (s, 1H), 7.42-7.35 (m, 2H), 7.35-7.22 (m, 11H), 7.19 (dd, J=7.2, 2.5 Hz, 2H), 6.82 (d, J=4.5 Hz, 1H), 6.41 (d, J=4.5 Hz, 1H), 5.60 (s, 2H), 4.87-4.72 (m, 3H), 4.56 (q, J=12.0 Hz, 2H), 4.46-4.40 (m, 4H), 4.33 (d, J=11.7 Hz, 1H), 3.94 (dd, J=8.0, 4.8 Hz, 1H), 3.82 (dd, J=10.7, 3.1 Hz, 1H), 3.66 (dd, J=10.7, 4.7 Hz, 1H); $^{13}C$ NMR (100 MHz, $CDCl_3$) δ 155.3, 146.7, 138.3, 138.0, 137.8, 131.4, 128.5, 128.48, 128.44, 128.42, 127.9, 127.8, 127.76, 127.73, 115.0, 112.2, 100.0, 86.0, 79.9, 79.5, 78.7, 73.9, 73.4, 72.6, 70.0, 64.1; HRMS (ESI−) calcd for $C_{33}H_{33}N_4O_5$ $[M-H]^-$ 565.2456, found 565.2487.

Synthesis of 4-Amino-7-[1'-hydroxymethyl-2',3',5'-trihydroxy-β-D ribofuranosyl)pyrolo[2,1-f][1,2,4] triazine](2)

The title compound was prepared from compound 19 (55 mg, 0.10 mmol, 1.00 equiv) using general procedure 1 to afford 3 (25 mg, 84%) as a white solid. $R_f$=0.18 ($H_2O$: MeOH:EtOAc=5:15:80); $^1H$ NMR (400 MHz, $D_2O$) δ 7.76 (s, 1H), 6.81 (q, J=4.6 Hz, 2H), 4.71 (d, J=5.2 Hz, 1H), 4.34 (d, J=12.0 Hz, 1H), 4.20-4.15 (m, 2H), 4.10 (dd, J=7.1, 5.2 Hz, 1H), 3.85 (dd, J=12.4, 3.0 Hz, 1H), 3.72 (dd, J=12.4, 5.4 Hz, 1H); $^{13}C$ NMR (101 MHz, $D_2O$) δ 155.1, 146.0, 130.1, 114.7, 111.4, 101.9, 85.7, 82.2, 74.1, 71.1, 62.0, 61.9; HRMS (APCI−) calcd for $C_{12}H_{15}N_4O_5$ $[M-H]^-$ 295.1047, found 295.1061. The anomeric stereochemistry was determined by NMR analysis and the structure was unambiguously confirmed by X-ray

2

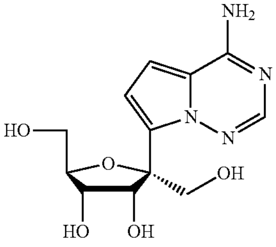

crystallography.

Synthesis of 4-Amino-7-[1'-(hydroxyimino)methyl-2',3',5'-O-tribenzyl-β-D-ribofuranosyl]pyrolo [2,1-t] [1,2,4]triazine (19)

To a stirring solution of 16 (0.10 g, 0.17 mmol, 1.00 equiv) in MeOH/$CH_2Cl_2$ (2:1; 2.00 mL) was added solid $NaHCO_3$ (74 mg, 0.88 mmol, 5.00 equiv) at 25° C. Then hydroxylamine hydrochloride (61 mg, 0.88 mmol, 5.00 equiv) was added to the reaction mixture and stirred the solution for overnight at same temperature. After the complete consumption of 16, the reaction mixture was evaporated to dryness. The crude was diluted with EtOAc and wash the solution with water,

19

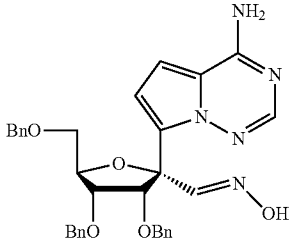

saturated aqueous $NH_4Cl$, then brine. The organic fraction was separated and dried over anhydrous sodium sulphate. Purification by silica gel flash chromatography (40-100% EtOAc/hexane) to afford the title compound (94 mg, 92%) as a white solid. $R_f$=0.3 (EtOAc:$CH_2Cl_2$=40:60); $^1H$ NMR (400 MHz, $CDCl_3$) δ 8.01 (s, 1H, imine-H), 7.66 (s, 1H), 7.38-7.33 (m, 2H), 7.26-7.15 (m, 11H), 7.08-7.05 (m, 2H), 6.65 (d, J=4.4 Hz, 1H), 6.10 (d, J=4.5 Hz, 1H), 4.83-4.73 (m, 3H), 4.56-4.48 (m, 2H), 4.46-4.42 (m, 1H), 4.24 (d, J=11.8 Hz, 1H), 4.10 (d, J=11.7 Hz, 1H), 3.79 (dd, J=10.8, 2.3 Hz, 1H), 3.75 (dd, J=9.1, 4.5 Hz, 1H), 3.61 (dd, J=10.8, 5.7 Hz, 1H); $^{13}C$ NMR (101 MHz, $CDCl_3$) δ 155.0, 147.3, 145.8, 138.2, 137.8, 137.7, 130.3, 128.7, 128.6, 128.4, 128.4, 128.0, 127.9, 127.8, 127.8, 127.6, 115.1, 111.4, 100.4, 84.6, 79.2, 78.9, 73.5, 73.3, 72.4, 70.7.

Synthesis of 4-Amino-[1'-(hydroxyimino)methyl-2',3',5'-trihydroxy-β-D-ribofuranosyl][pyrolo[2,1-f][1,2,4]triazine (3)

Following the general procedure 1, compound 3 was synthesized from 19 (78 mg, 0.13 mmol, 1.00 equiv). The product was purified using flash silica gel

3

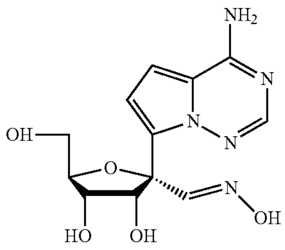

chromatography (0-15% MeOH/EtOAc) to afford the title compound 3 (35 mg, 85%) as a light yellow solid. $R_f$=0.25 (MeOH:EtOAc=8:92); $^1$H NMR (400 MHz, $CD_3OD$) δ 7.99 (s, 1H), 7.76 (s, 1H), 6.84 (d, J=4.6 Hz, 1 Hz), 6.78 (d, J=4.6 Hz, 1H), 4.81 (d, J=5.1 Hz, 1H), 4.17-4.14 (m, 1H), 4.05 (dd, J=6.1, 5.1 Hz, 1H), 3.81 (dd, J=12.1, 3.1 Hz, 1H), 3.69 (dd, J=12.1, 4.8 Hz, 1H); $^{13}$C NMR (101 MHz, $CD_3OD$) δ 157.2, 150.9, 147.6, 131.7, 116.5, 112.0, 102.5, 85.2, 84.7, 76.5, 73.0, 63.8; FTIR ($cm^{-1}$): 3285, 1656, 1604, 1553, 1054; HRMS (ESI+) calcd for $C_{12}H_{15}N_5O_5$ $[M+H]^+$ 310.1107, found 310.1114.

Synthesis of 4-Amino-7-(1'-carboxamide-2',3',5'-O-tribenzyl-β-D-ribofuranosyl)pyrolo[2,1-t][1,2,4]triazine (20)

Compound 15 (0.28 g, 0.50 mmol, 1.00 equiv) and sodium hydroxide (40 mg, 1.00 mmol, 2.00 equiv) dissolved in isopropyl alcohol (2.00 mL) were heated at 70° C. for 6 h. After completion of the reaction, the crude reaction mixture was evaporated to dryness. The residue was then purified by column chromatography (0-80% EtOAc/Hexane) to obtain the title compound 20 (0.15 g, 55%) as an

20

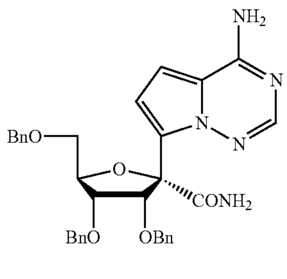

amorphous white solid. $R_f$=0.21 (60% EtOAc/Hexane); $^1$H NMR (400 MHz, $CDCl_3$) δ 7.73 (s, 1H), 7.37-7.30 (m, 2H), 7.26-7.14 (m, 8H), 7.10 (dd, J=5.2, 1.9 Hz, 3H), 6.87 (dd, J=7.0, 2.6 Hz, 2H), 6.37-6.32 (m, 2H), 5.01 (d, J=3.9 Hz, 1H), 4.78 (d, J=11.4 Hz, 1H), 4.67 (d, J=11.4 Hz, 1H), 4.50-4.37 (m, 3H), 4.24-4.13 (m, 3H), 3.49 (dd, J=11.2, 2.9 Hz, 1H), 3.36 (dd, J=11.3, 4.4 Hz, 1H); $^{13}$C NMR (100 MHz, $CDCl_3$) δ 172.4, 155.2, 146.6, 138.1, 137.7, 128.56, 128.53, 128.45, 128.43, 128.40, 128.3, 128.28, 128.23, 128.1, 128.08, 128.03, 127.97, 127.94, 127.8, 127.4, 127.2, 115.1, 110.7, 100.6, 85.9, 85.9, 81.27, 80.3, 79.2, 74.4, 73.1, 72.9, 69.4; HRMS (ESI+) calcd for $C_{33}H_{34}N_5O_5$ $[M+H]^+$ 580.2560, found 580.2600.

Synthesis of 4-Amino-7-(1'-carboxamide-2',3',5'-trihydroxy-β-D-ribofuranosyl)pyrolo[2,1-f][1,2,4]triazine (4)

The title compound was prepared from 20 (57 mg, 0.10 mmol, 1.00 equiv) using general procedure 1 to afford compound 4 (23 mg, 74%) as a white solid. Rr=0.12 (EtOAc:MeOH:$H_2O$:HCOOH=75:20:4:1); $^1$H NMR (400 MHz, $CD_3OD$) δ 7.77 (s, 1H), 6.86 (d, J=4.6 Hz, 1H), 6.75 (d, J=4.6 Hz, 1H), 5.04 (d, J=3.8 Hz, 1H) 4.23 (dd, J=4.4, 2.4 Hz, 2H), 3.75 (dd, J=11.6, 1.9 Hz, 1H), 3.52 (dd, J=

4

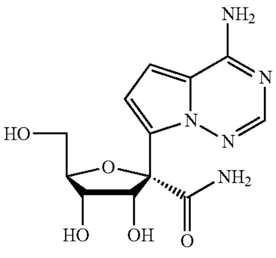

12.0, 4.4 Hz, 1H).; $^{13}$C NMR (151 MHz, $CD_3OD$) δ 175.9, 157.2, 147.8, 129.4, 116.8, 112.2, 102.6, 85.86, 85.4, 7635, 73.4, 63.9; HRMS (ESI−) calcd for $C_{12}H_{15}N_5O_5$ $[M-H]^-$ 308.1000, found 308.1016. The anomeric stereochemistry was determined by NMR analysis and the structure was unambiguously confirmed by X-ray crystallography.

4-Amino-7-(1'-carboxy-2',3',5'-O-tribenzyl-β-D-ribofuranosyl)pyrrolo[2,1-f][1,2,4]triazine (21)

Nitrile 15 (0.10 g, 0.19 mmol, 1.00 equiv.) was dissolved in a mixture of ethanol and water (1:1) was added with sodium hydroxide (20 mg, 0.50 mmol, 5.00 equiv). Then the reaction mixture was refluxed for 10 h. After completion of the reaction, the crude reaction mixture was evaporated to dryness. The residue was then purified by column chromatography (0-80% EtOAc/Hexane) to obtain the title

21

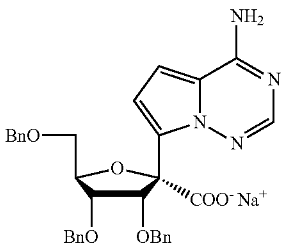

compound 21 (0.08 g, 40%) as an amorphous white. $R_f$=0.18 (60% EtOAc/Hexane); $^1$H NMR (400 MHz, MeOD) δ 7.74 (s, 1H), 7.43-7.38 (m, 2H), 7.34-7.22 (m, 8H), 7.20-7.14 (m, 3H), 6.92-6.87 (m, 2H), 6.79 (d, J=4.6 Hz, 1H), 6.61 (d, J=4.6 Hz, 1H), 5.14 (d, J=3.8 Hz, 1H), 4.82 (d, J=11.0 Hz, 1H), 4.76 (d, J=11.0 Hz, 1H), 4.63 (d, J=11.8 Hz, 1H), 4.54 (d, J=11.7 Hz, 1H), 4.44 (ddd, J=8.8, 4.1, 2.4 Hz, 1H), 4.37 (dd, J=8.9, 3.8 Hz, 1H), 4.23 (d, J=2.2 Hz, 2H), 3.59 (dd, J=11.3, 2.4 Hz, 1H), 3.44-3.36 (m, 1H); $^{13}C$ NMR (100 MHz, MeOD) δ 174.8, 157.1, 147.5, 139.6, 139.4, 139.1, 129.9, 129.4, 129.3, 129.26, 129.21, 129.1, 129.0, 128.6, 128.3, 128.2, 116.5, 111.7, 102.4, 87.1, 82.4, 81.7, 80.0, 75.6, 74.1, 73.8, 70.1; FTIR ($cm^{-1}$): 3337, 2950, 1680, 1607, 1264, 1083; HRMS (ESI+) calcd for $C_{33}H_{31}N_4O_6Na$ $[M+H]^+$ 602.2141, found 602.2156. $[\alpha]^{23}_D$ 18.38 (c 0.21, MeOH); Melting point above 200° C.

4-Amino-7-(1'-carboxyl-2',3',5'-trihydroxy-β-D-ribofuranosyl)pyrrolo[2,1-f][1,2,4]triazine (5)

The title compound was prepared from 21 (0.06 g, 0.10 mmol, 1.00 equiv) using general procedure 1 to afford compound 5 (0.10 g, 85%) as a white solid. R, =0.15 (20% MeOH in EtOAC); $^1H$ NMR (400 MHz, $CD_3OD$) δ 7.96 (s, 1H), 7.38 (d, J=4.8 Hz, 1H), 6.98 (d, J=4.8 Hz, 1H), 5.01 (d, J=4.0 Hz, 1H), 4.27-4.19 (m, 2H), 3.74 (dd, J=12.1, 2.4 Hz, 1H), 3.47 (dd, J=12.2, 4.6 Hz, 1H); $^{13}C$ NMR

5

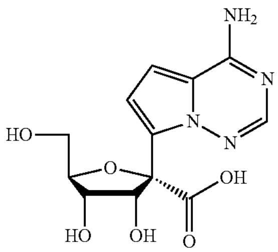

(151 MHz, $CD_3OD$) 174.8, 150.4, 136.5, 136.0, 114.4, 113.58, 110.6, 86.4, 85.4, 76.5, 72.9, 62.8.; FTIR ($cm^{-1}$): 2933, 2862, 1742, 1522, 1455, 1369, 1056; HRMS (ESI+) calcd for $C_{12}H_{14}N_4O_5$ $[M]^+$ 310.1123, found 310.1150; $[\alpha]^{23}_D$=15.38 (c 0.01, MeOH); Melting point above 200° C.

4-Amino-7-(1'-carboxthioamide-2',3',5'-O-tribenzyl-3-D-ribofuranosyl) pyrrolo [2,1-f][1,2,4]triazine (22)

Nitrile 15 (0.21 g, 0.38 mmol, 1.00 equiv.) was dissolved in pyridine (2.00 mL). Triethylamine (0.84 mmol, 2.20 equiv.) and ammonium sulfide 40-48% wt % solution in water (0.84 mmol, 2.2 equiv.) were added into the mixture. The reaction mixture was stirred at 50° C. for 6 h. After being cooled to room temperature, the reaction mixture was diluted with cold water (30 mL) and extracted with ethyl

22

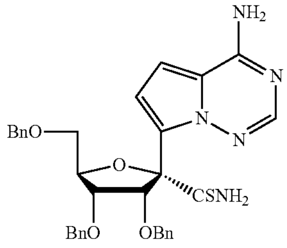

acetate (3×20 mL). The combined organic layer was concentrated and purified using column chromatography to (0-80% EtOAc/Hexane) to obtain the title compound 22 (0.17 g, 78%) as an amorphous white solid. $R_f$=0.23 (60% EtOAc/Hexane); $^1H$ NMR (400 MHz, $CDCl_3$) δ 8.78 (d, J=5.2 Hz, 1H), 8.29 (s, 1H), 7.92 (s, 1H), 7.50-7.42 (m, 2H), 7.36-7.27 (m, 8H), 7.21-7.14 (m, 3H), 6.86 (dd, J=6.7, 2.9 Hz, 2H), 6.46 (q, J=4.6 Hz, 2H), 5.68 (s, 2H), 5.07 (d, J=3.4 Hz, 1H), 4.95 (d, J=10.5 Hz, 1H), 4.83 (d, J=10.5 Hz, 1H), 4.64-4.55 (m, 2H), 4.54-4.46 (m, 2H), 4.23 (d, J=12.2 Hz, 1H), 4.15 (d, J=12.2 Hz, 1H), 3.53 (dd, J=11.5, 2.5 Hz, 1H), 3.37 (dd, J=11.4, 4.0 Hz, 1H); $^{13}C$ NMR (100 MHz, $CDCl_3$) δ 202.7, 155.3, 146.9, 138.2, 138.1, 137.7, 129.6, 128.6, 128.5, 128.4, 128.2, 128.19, 128.14, 127.9, 127.3, 127.1, 114.8, 110.2, 100.0, 90.6, 82.3, 81.9, 79.2, 75.9, 73.2, 73.0,; FTIR ($cm^{-1}$):1617, 1511, 1470, 1421, 1358, 1265; HRMS (ESI+) calcd for $C_{33}H_{34}N_5O_4S$ $[M+H]^+$ 596.2332, found 596.2323. $[\alpha]^{23}_D$=−64.08 (c 0.04, $CHCl_3$); Melting point: Decomposition begins at 200° C.

4-Amino-7-(1'-carboxthioamide-2',3',5'-trihydroxy-β-D-ribofuranosyl) pyrrolo[2,1-f][1,2,4]triazine (6)

The title compound was prepared from 22 (0.20 g, 0.37 mmol, 1.00 equiv) using general procedure 1 to afford compound 6 (0.10 g, 85%) as a yellow solid. $R_f$=0.15 (20% MeOH in EtOAC); $^1H$ NMR (400 MHz, $CD_3OD$) δ 7.93 (s, 1H), 7.40 (d, J=4.8 Hz, 1H), 6.97 (d, J=4.9 Hz, 1H), 5.02 (d, J=4.1 Hz, 1H), 4.39 (dd, J=

6

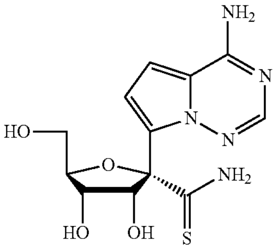

8.6, 4.2 Hz, 1H), 4.23 (ddd, J=8.5, 4.8, 2.5 Hz, 1H), 3.69 (dd, J=12.3, 2.5 Hz, 1H), 3.41-3.33 (m, 1H); $^{13}C$ NMR (151 MHz, $CD_3OD$) δ 203.1, 150.0, 138.0, 135.3, 114.1, 112.8, 110.8, 91.2, 85.7, 77.8, 72.6, 62.6; FTIR ($cm^1$): 3185, 1667, 1612, 1423, 1354; HRMS (ESI+) calcd for $C_{12}H_{16}N_5O_4S$ $[M+H]^+$ 326.0923, found 326.0920. $[\alpha]^{23}_D$=−60 (c 0.01, MeOH); Melting point above 200° C.

4-Amino-7-(1'-amidoxime-2',3',5'-O-tribenzyl-β-D-ribofuranosyl)pyrrolo[2,1-f][1,2,4]triazine (23)

Nitrile 15 (0.20 g, 0.36 mmol, 1.00 equiv.) and hydroxylamine hydrochloride (0.12 g, 1.80 mmol, 5.00 equiv.) was dissolved in methanol and the reaction mixture was heated at 60° C. for 8 h. After being cooled to room temperature, the reaction mixture was diluted with cold water (40 mL) and

23

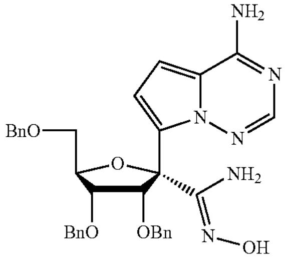

extracted with ethyl acetate (3×20 mL). The combined organic layer was concentrated and purified using column chromatography to (0-80% EtOAc/Hexane) to obtain the title compound 23 (0.18 g, 85%). $R_f$=0.18 (65% EtOAc/Hexane); $^1$H NMR (400 MHz, $CD_3OD$) δ 7.70 (s, 1H), 7.42-7.37 (m, 2H), 7.31-7.25 (m, 8H), 7.22-7.16 (m, 3H), 6.97-6.92 (m, 2H), 6.76 (d, J=4.6 Hz, 1H), 6.60 (d, J=4.6 Hz, 1H), 5.06 (d, J=4.1 Hz, 1H), 4.81 (d, J=11.3 Hz, 1H), 4.71 (d, J=11.3 Hz, 1H), 4.57 (d, J=11.9 Hz, 1H), 4.49 (d, J=11.8 Hz, 1H), 4.40 (ddd, J=7.4, 4.1, 3.0 Hz, 1H), 4.27 (dd, J=6.6, 4.3 Hz, 3H), 3.58 (dd, J=11.3, 3.0 Hz, 1H), 3.41 (dd, J=11.2, 4.1 Hz, 1H); $^{13}$C NMR (101 MHz, $CD_3OD$) δ 157.1, 157.0, 147.4, 139.5, 139.4, 139.1, 130.5, 129.5, 129.4, 129.38, 129.30, 129.2, 129.1, 128.9, 128.7, 128.35, 128.33, 116.6, 111.8, 102.3, 84.1, 82.4, 82.3, 79.5, 75.2, 74.1, 73.6, 70.2; FTIR ($cm^{-1}$): 3052, 1612, 1423, 1354, 1265, 896; HRMS (ESI+) calcd for $C_{33}H_{32}N_6O_5$ $[M-H]^-$ 593.2512, found 593.2509. $[\alpha]^{23}_D$=−32.43 (c 0.03, $CHCl_3$); Melting point above 200° C.

4-Amino-7-(1'-amidoxime-2',3',5'-trihydroxy-3-D-ribofuranosyl)pyrrolo[2,1-f][1,2,4]triazine (7)

The title compound was prepared from 23 (0.15 g, 0.25 mmol, 1.00 equiv) using general procedure 1 to afford compound 7 (0.0.07 g, 83%) as a white solid. $R_f$=0.12 (25% MeOH in EtOAC); $^1$H NMR (400 MHz, $CD_3OD$) δ 7.96 (s, 1H), 7.38 (d, J=4.8 Hz, 1H), 6.98 (d, J=4.8 Hz, 1H), 5.01 (d, J=4.0 Hz, 1H), 4.27-4.19 (m, 2H), 3.74 (dd, J=12.1, 2.4 Hz, 1H), 3.47 (dd, J=12.2, 4.6 Hz, 1H); $^{13}$C NMR (151 MHz, $CD_3OD$) 174.8, 150.4, 136.5, 136.0, 114.4, 113.58, 110.6, 86.4, 85.4, 76.5, 72.9, 62.8.; FTIR ($cm^{-1}$): 3043, 3021, 3004, 1667, 1360, 1235, 1025; HRMS (ESI−) calcd for $C_{12}H_{15}N_6O_5$ $[M-H]^-$ 323.1104, found 323.1108 $[\alpha]^{23}$D=480 (c 0.05, MeOH); Melting point 129-131° C.

7

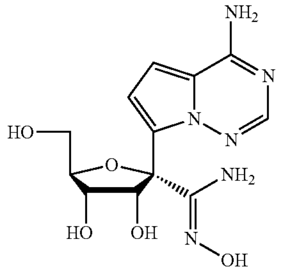

4-Amino-7-(1'-methyl-2',3',5'-O-tribenzyl-α,β-D-ribofuranosyl)pyrrolo[2,1-f][1,2,4]triazine (30)

Compounds 30 was prepared from 26 (1.06 g, 2.30 mmol, 1.00 equiv), methyl magnesium bromide (6.13 mL, 18.4 mmol, 3.00 M in diethylether), acetic acid (1.32 mL, 21.0 mmol) and methanesulfonic acid (0.60 mL, 8.22 mmol) using general procedure 2 to afford 30 (0.50 g, 0.92 mmol, 40%) as a 1:1 mixture of beta and alpha-anomers respectively. Both anomers were successfully separated by normal phase preparative HPLC using 10% isopropanol and n-heptane (isocratic). Although this compound has been disclosed; no physical or spectroscopic

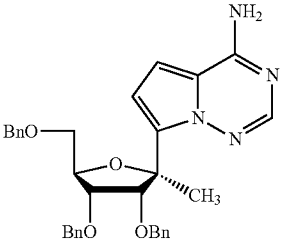

+

30 (β-anomer)

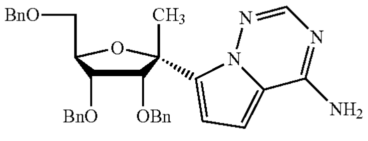

30 (α-anomer)

characterization data was reported, thus we have provided complete characterization data.

Data for 30 (α-anomer): HPLC ($t_R$=8.14 min; k'=2.25); $R_f$=0.33 (60% EtOAc/Hexane); $[\alpha]^{23}_D$ +43 (c 0.40, $CHCl_3$); $^1$H NMR (400 MHz, $CDCl_3$) δ 7.76 (s, 1H), 7.39-7.25 (m, 10H), 7.07 (q, J=6.8, 6.2 Hz, 3H), 6.87 (d, J=4.5 Hz, 1H), 6.68 (d, J=4.5 Hz, 1H), 6.66-6.60 (m, 2H), 5.75 (s, 2H), 4.66 (dd, J=15.6, 11.8 Hz, 3H), 4.55 (dd, J=12.0, 6.0 Hz, 2H), 4.50 (d, J=3.6 Hz, 1H), 4.43-4.33 (m, 2H), 4.30 (d, J=11.5 Hz, 1H), 3.86 (dd, J=11.0, 2.2 Hz, 1H), 3.66 (dd, J=11.0, 3.5 Hz, 1H), 1.73 (s, 3H); $^{13}$C NMR (101 MHz, $CDCl_3$) δ 154.6, 145.2, 138.6, 138.6, 138.0, 135.3, 128.5, 128.4, 127.95, 127.93, 127.79, 127.71, 127.5, 127.1, 126.9, 113.9, 110.7, 100.8, 84.5, 82.5, 79.2, 79.1, 73.9, 73.4, 72.9, 69.5, 25.5; FTIR ($cm^{-1}$) 3336, 2974, 2875, 1604, 1455, 1265, 1047; HRMS (APCI-TOF) m/z: $[M-H]^-$ calcd for $C_{33}H_{33}N_4O_4$ 549.2507; found 549.2507. The anomeric stereochemistry was determined by NMR analysis and the structure was confirmed by a 2D-NOESY experiment. Key 2D-NOESY correlations of [H4'-H8] and [H2'—$CH_3$1'] were observed.

Data for 30 (β-anomer): HPLC ($t_R$=9.80 min; k'=2.92); $R_f$=0.33 (60% EtOAc/Hexane); $[\alpha]^{23}_D$ −24 (c 0.15, $CHCl_3$); $^1$H NMR (400 MHz, $CDCl_3$) δ 7.77 (s, 1H), 7.31 (dd, J=7.0, 2.5 Hz, 2H), 7.28-7.13 (m, 11H), 7.09 (dd, J=7.1, 2.7 Hz, 2H), 6.76 (d, J=4.5 Hz, 1H), 6.52 (d, J=4.5 Hz, 1H), 5.76 (s, 2H), 4.80-4.70 (m, 2H), 4.58-4.44 (m, 3H), 4.31 (dd, J=13.2, 8.4 Hz, 2H), 4.19 (d, J=11.9 Hz, 1H), 3.81 (dd, J=8.1, 4.9 Hz, 1H), 3.72 (dd, J=10.7, 3.3 Hz, 1H), 3.56 (dd, J=10.6, 4.9 Hz, 1H); $^{13}$C NMR (101 MHz, $CDCl_3$) δ 154.6, 145.0, 138.5, 138.1, 135.7, 128.4, 128.3, 128.2, 127.77, 127.74, 127.68, 127.61, 114.62, 111.2, 100.9, 83.7, 78.9, 78.8, 78.6, 73.3, 73.2, 72.3, 70.1, 20.7; FTIR ($cm^{-1}$) 3050, 2927, 2864, 1604, 1265, 1088, 1026; HRMS (ESI-TOF) m/z: $[M+H]^+$: calcd for $C_{33}H_{35}N_4O_4$ 551.2652; found 551.2660. The anomeric stereochemistry was determined by NMR analysis and the structure was confirmed by a 2D-NOESY experiment. Key 2D-NOESY correlations of [H5'-H8] and [H4'—$CH_3$1'] were observed.

4-Amino-7-(1'-ethyl-2',3',5'-O-tri benzyl-α,β-D-ribofuranosyl)pyrrolo[2,1-f][1,2,4]triazine (31)

The title compound was prepared from 26 (0.50 g, 1.15 mmol, 1.00 equiv), ethyl magnesium bromide (3.10 mL, 9.20 mmol, 3.00 M in diethylether), acetic acid (0.65 mL, 10.50 mmol) and methanesulfonic acid (0.30 mL, 4.11 mmol) using general procedure 2 to afford 31 (0.25 g, 0.45 mmol, 41%) as a 1:1 mixture

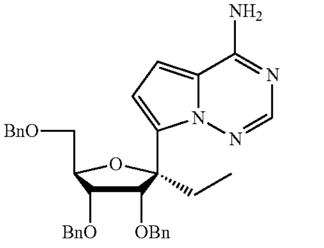

31 (β-anomer)

+

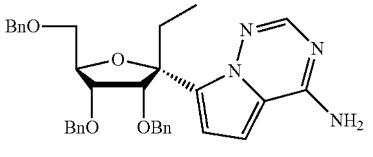

31 (α-anomer)

of beta and alpha-anomers. Both anomers were successfully separated by normal phase preparative HPLC using 10% isopropanol and n-heptane (isocratic).

Data for 31 (α-anomer): HPLC ($t_R$=9.96 min; k'=2.98); $R_f$=0.34 (60% EtOAc/Hexane); $[\alpha]^{23}_D$ −31 (c 0.19, $CHCl_3$); $^1$H NMR (600 MHz, $CD_3OD$) δ 7.63 (s, 1H), 7.39-7.31 (m, 8H), 7.29 (ddt, J=7.8, 6.3, 2.8 Hz, 2H), 7.08-7.04 (m, 1H), 7.04-6.96 (m, 3H), 6.79 (d, J=4.5 Hz, 1H), 6.56-6.52 (m, 2H), 4.71 (dd, J=11.7, 2.2 Hz, 2H), 4.64-4.59 (m, 2H), 4.56 (d, J=12.0 Hz, 1H), 4.51 (d, J=4.1 Hz, 1H), 4.39-4.32 (m, 2H), 4.25 (ddd, J=9.2, 4.3, 2.3 Hz, 1H), 3.81 (dd, J=10.9, 2.4 Hz, 1H), 3.61 (dd, J=11.0, 4.2 Hz, 1H), 2.47 (dq, J=14.8, 7.5 Hz, 1H), 1.74 (dq, J=14.4, 7.3 Hz, 1H), 0.65 (t, J=7.3 Hz, 3H); $^{13}$C NMR (151 MHz, $CD_3OD$) δ 154.8, 143.7, 140.1, 139.7, 139.4, 135.8, 129.4, 129.3, 129.1, 128.9, 128.7, 128.6, 127.9, 127.4, 114.6, 113.1, 104.7, 89.3, 84.3, 80.7, 80.5, 75.3, 74.3, 74.0, 70.8, 31.0, 8.4; FTIR ($cm^{-1}$) 3343, 2974, 2883, 1604, 1276, 1045; HRMS (ESI-TOF) m/z: $[M+H]^+$ calcd for $C_{34}H_{38}N_4O_4$ 565.2820; found 565.2817. The anomeric stereochemistry was determined by NMR analysis and the structure was confirmed by a 2D-NOESY experiment. Key 2D-NOESY correlations of [H4'-H8] and [H2'-$C_2H_5$1'] were observed.

Data for 31 (β-anomer): HPLC ($t_R$=12.06 min; k'=3.84); $R_f$=0.34 (60% EtOAc/Hexane); $[\alpha]^{23}_D$ +63 (c 0.22 $CHCl_3$); $^1$H NMR (600 MHz, $CD_3OD$) δ 7.81 (s, 1H), 7.45-7.40 (m, 2H), 7.3-7.26 (m, 8H), 7.20 (dt, J=5.1, 2.3 Hz, 3H), 7.14 (dd, J=6.9, 2.9 Hz, 2H), 6.87 (d, J=4.6 Hz, 1H), 6.79 (d, J=4.6 Hz, 1H), 4.85 (d, J=3.9 Hz, 1H), 4.64-4.57 (m, 2H), 4.52 (d, J=11.9 Hz, 1H), 4.35 (d, J=11.6 Hz, 1H), 4.22 (d, J=11.7 Hz, 2H), 3.86 (dd, J=9.2, 4.5 Hz, 1H), 3.78 (dd, J=10.8, 2.6 Hz, 1H), 3.61 (dd, J=10.8, 4.7 Hz, 1H), 2.58 (dq, J=14.9, 7.5 Hz, 1H), 2.21 (dq, J=14.6, 7.4 Hz, 1H), 0.60 (t, J=7.5 Hz, 3H); $^{13}$C NMR (151 MHz, $CD_3OD$) b 155.3, 144.5, 139.8, 139.6, 139.1, 135.6, 129.52, 129.50, 129.4, 129.3, 129.29, 129.25, 129.06, 129.04, 128.8, 128.77, 128.75, 128.6, 115.3, 113.75, 104.2, 88.4, 80.7, 79.9, 79.7, 75.0, 74.1, 73.5, 70.9, 26.5, 8.3; FTIR ($cm^{-1}$) 3343, 2974, 1606, 1276, 1045; HRMS (ESI-TOF) m/z: $[M+H]^+$ calcd for $C_{34}H_{38}N_4O_4$ 565.2820; found 565.2817. The anomeric stereochemistry was determined by NMR analysis and the structure was confirmed by a 2D-NOESY experiment. Key 2D-NOESY correlations of [H5'-H8] and [H3'-H8] were observed.

4-Amino-7-(1'-vinyl-2',3',5'-O-tribenzyl-α/β-D-ribofuranosyl)pyrrolo[2,1-f][1,2,4]triazine (32)

This title compound was prepared from hydroxyketone 26 (0.50 g, 0.90 mmol, 1.00 equiv) and vinyl magnesium bromide (5.40 mL, 5.40 mmol, 6.00 equiv) using the general procedure 2. Purification by flash chromatography (20% EtOAc/$CH_2Cl_2$) afforded 32 (229 mg, 45%; after two step) as a light-yellow solid as a 1:1.6 mixture of α and β-anomers. The two anomers were separated by normal

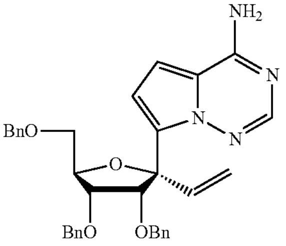

32 (β-anomer)

+

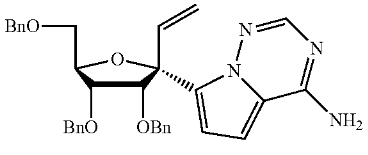

32 (α-anomer)

phase prep-HPLC using 15% isopropanol/n-heptane (isocratic). Although these compounds have been disclosed; no physical or spectroscopic characterization data was reported, thus we have provided complete characterization data.

Data for 32 (α-anomer): HPLC ($t_R$=7.23 min; k'=1.89); $R_f$=0.30 (60% EtOAc/$CH_2Cl_2$); $[\alpha]^{23}_D$+17 (c 0.60, $CHCl_3$); $^1$H NMR (600 MHz, $CDCl_3$) δ 7.78 (s, 1H), 7.38-7.27 (m, 10H), 7.10-7.03 (m, 3H), 6.87 (d, J=4.5 Hz, 1H), 6.67-6.61 (m, 4H), 5.62 (dd, J=17.0, 1.6 Hz, 1H), 5.13 (dd, J=10.6, 1.6 Hz, 1H), 4.69-4.64 (m, 3H), 4.64-4.58 (m, 2H), 4.53 (d, J=11.8 Hz, 1H), 4.44 (ddd, J=9.5, 4.5, 2.3 Hz, 1H), 4.34 (d, J=11.4 Hz, 1H), 4.28 (dd, J=9.5, 3.8 Hz, 1H), 3.93 (dd, J=11.0, 2.4 Hz, 1H), 3.72 (dd, J=11.0, 4.5 Hz, 1H); $^{13}$C NMR (101 MHz, $CDCl_3$) δ 154.8, 145.8, 138.6, 138.5, 138.0, 137.6, 133.0, 128.5, 128.4, 127.9, 127.9, 127.7, 127.7, 127.6, 127.1, 126.8, 115.3, 114.0, 110.5, 100.6, 86.7, 81.4, 78.8, 74.0, 73.3, 72.9, 69.7; FTIR ($cm^{-1}$) 2924, 2857, 1638, 1602, 1257; HRMS (ESI-TOF) m/z: $[M+H]^+$ calcd for $C_{34}H_{35}N_4O_5$ 563.2653; found 563.2647. The anomeric stereochemistry was determined by NMR analysis and the structure was confirmed by a 2D-NOESY experiment. Key 2D-NOESY correlations of [H4'-H8], [H3'-1'-vinyl] and [H5'-1'-vinyl] were observed.

Data for 32 (β-isomer): HPLC ($t_R$=8.65 min; k'=2.65); Rdf=0.30 (60% EtOAc/$CH_2Cl_2$); $[\alpha]^{23}_D$+3.1 (c 0.93, $CHCl_3$); $^1$H NMR (600 MHz, $CDCl_3$) δ 7.79 (s, 1H), 7.37-7.29 (m, 2H), 7.26-7.11 (m, 11H), 7.07 (dd, J=7.4, 2.1 Hz, 2H), 6.75 (d, J=4.5 Hz, 1H), 6.64 (dd, J=17.2, 10.7 Hz, 1H), 6.44 (d, J=4.5 Hz, 1H), 5.76 (br s, 2H), 5.29-5.15 (m, 2H), 4.84-4.67 (m, 3H), 4.60-4.45 (m, 2H), 4.37 (ddd, J=8.0, 4.5, 3.1 Hz, 1H), 4.30-4.09 (m, 2H), 3.82 (dd, J=8.4, 4.8 Hz, 1H), 3.78 (dd, J=10.8, 3.1 Hz, 1H), 3.60 (dd, J=10.7, 4.6 Hz, 1H); $^{13}$C NMR (101 MHz, $CDCl_3$) δ 155.0, 145.8, 138.5, 138.4, 138.0, 135.1, 132.7, 128.4, 128.3, 128.3, 127.7, 127.7, 127.6, 127.6, 127.5, 115.8, 114.8, 112.0, 100.5, 85.9, 79.4, 78.9, 73.3, 73.0, 72.1, 69.8; FTIR ($cm^{-1}$) 2924, 2857, 1638, 1602, 1257; HRMS (ESI-TOF) m/z: $[M+H]^+$ calcd for $C_{34}H_{35}N_4O_5$ 563.2653; found 563.2647. The anomeric stereochemistry was determined by NMR analysis and the structure was confirmed by a 2D-NOESY experiment. Key 2D-NOESY correlations of [H4'-1'-vinyl], [H3'-H8] and [H5'-H8] were observed.

4-Amino-7-(1'-methyl-2',3',5'-trihydroxy-α/β-D-ribofuranosyl)pyrrolo[2,1-f][1,2,4]triazine (8)

The title compound was prepared from compound 30 (108 mg, 0.20 mmol, 1.00 equiv) using general procedure 1 to afford the 8 (pure, β-anomer, 25 mg, 42%) as a white solid after recrystallization using methanol and water (9:1). Although this compound has been disclosed; no physical or spectroscopic

8

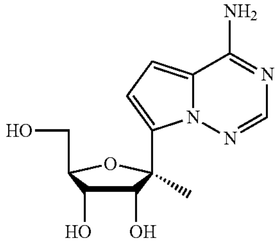

characterization data was reported, thus we have provided complete characterization data. Mp: Decomposition begins at 190° C.; $R_f$=0.18 ($H_2O$:MeOH:EtOAc=5:15:80); $R_f$=0.40 (10% MeOH/EtOAc); $[\alpha]^{23}_D$ +23 (c 0.070, MeOH); $^1H$ NMR (400 MHz, $CD_3OD$) δ 7.75 (s, 1H), 6.85 (d, J=4.5 Hz, 1H), 6.77 (d, J=4.5 Hz, 1H), 4.65 (d, J=5.4 Hz, 1H), 4.10-4.00 (m, 2H), 3.82 (dd, J=11.9, 2.7 Hz, 1H), 3.71 (dd, J=11.9, 4.4 Hz, 1H), 1.72 (s, 3H); $^{13}C$ NMR (101 MHz, $CD_3OD$) δ 147.4, 135.6, 116.4, 111.3, 102.6, 84.8, 84.5, 75.1, 73.3, 64.3, 20.6; FTIR ($cm^{-1}$) 3342, 2976, 2892, 1613, 1269, 1088, 1045; HRMS (ESI-TOF) m/z: $[M+H]^+$ calcd for $C_{12}H_{15}N_4O_4$ 281.1255; found 281.1249. The anomeric stereochemistry was determined by NMR analysis and the structure was unambiguously confirmed by X-ray crystallography.

Data for 8 (α-anomer). The mother liquor containing α-anomer of 8 from above experiment was collected and dried (24 mg, 42%); $R_f$=0.25 (1

8

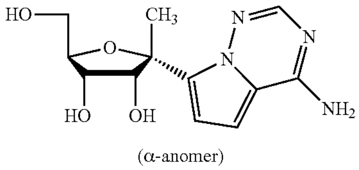

(α-anomer)

$H_2O$:MeOH:EtOAc=5:15:80); $^1H$ NMR (400 MHz, $CD_3OD$) δ 7.75 (s, 1H), 6.89 (d, J=4.4 Hz, 1H), 6.67 (d, J=4.6 Hz, 1H), 4.46 (d, J=8.0 Hz, 1H), 3.86-3.79 (m, 1H), 3.78-3.71 (m, 1H), 3.68-3.60 (m, 2H), 1.77 (s, 3H); $^{13}C$ NMR (101 MHz, $CD_3OD$) δ 157.1, 147.4, 132.4, 116.4, 113.8, 102.6, 81.5, 77.5, 74.7, 73.7, 63.8, 50.7, 18.2; HRMS (ESI+) calcd for $C_{12}H_{17}N_4O_4$ $[M+H]^+$ 281.1255, found 281.1249 (error-2.1 ppm).

4-Amino-7-(1'-ethyl-2',3',5'-trihydroxy-α/β-D-ribofuranosyl)pyrrolo[2,1-f][1,2,4]triazine (9)

The title compound was prepared from 32 (0.11 g, 0.20 mmol, 1.00 equiv) using general procedure 1 to afford 9 (49 mg, 85%) as mixture of beta and alpha-anomers. Both anomers were separated by normal phase preparative HPLC using a linear gradient of isopropanol (30-70%) and hexane.

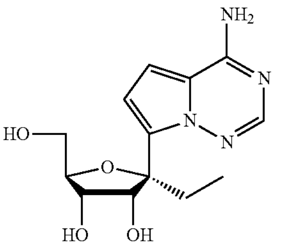

9 (β-anomer)

+

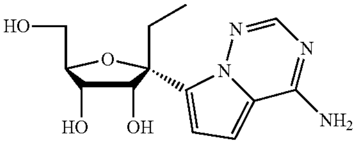

9 (α-anomer)

Data for 9. (β-anomer): HPLC ($t_R$=11.7 min, k'=3.6). $R_f$=0.17 (20% MeOH/EtOAc); $[\alpha]^{23}_D$ −25 (c 0.050, MeOH); $^1H$ NMR (400 MHz, $CD_3OD$) δ 7.74 (s, 1H), 6.84 (d, J=4.5 Hz, 1H), 6.79 (d, J=4.5 Hz, 1H), 4.56 (d, J=5.2 Hz, 1H), 3.99 (td, J=5.3, 2.7 Hz, 1H), 3.90 (dd, J=7.6, 5.2 Hz, 1H), 3.81 (dd, J=11.9, 2.9 Hz, 1H), 3.69 (dd, J=11.9, 5.6 Hz, 1H), 2.40 (dq, J=15.0, 7.6 Hz, 1H), 2.14 (dq, J=14.6, 7.4 Hz, 1H), 0.63 (t, J=7.4 Hz, 3H); $^{13}C$ NMR (101 MHz, $CD_3OD$) δ 157.2, 147.4, 134.5, 112.5, 102.4, 88.0, 83.4, 76.0, 73.1, 64.2, 25.8, 8.1; FTIR ($cm^{-1}$) 3317, 2944, 2832, 1610, 1420, 1110, 1021; HRMS (APCI-TOF) m/z: $[M-H]^-$ calcd for $C_{13}H_{16}N_4O_4$ 293.1255; found 293.1271. The anomeric stereochemistry was determined by NMR analysis and the structure was confirmed by a 2D-NOESY experiment. Key 2D-NOESY correlations of [H4'-1'-Et], [H5'—H8], [H3'—H8] and [H2'—H8] were observed.

Data for 9 (α-anomer): HPLC ($t_R$=13.8 min, k'=4.5). $R_f$=0.17 (20% MeOH/EtOAc); $^1H$ NMR (600 MHz, CD3OD) δ 7.75 (s, 1H), 6.85 (d, J=4.4 Hz, 1H), 6.73 (d, J=4.4 Hz, 1H), 4.45 (d, J=5.0 Hz, 1H), 4.16 (dd, J=8.8, 5.0 Hz, 1H), 3.96 (ddd, J=8.5, 5.4, 2.5 Hz, 1H), 3.89 (dd, J=11.9, 2.5 Hz, 1H), 3.67 (dd, J=11.9, 5.4 Hz, 1H), 2.45-2.37 (m, 1H), 1.72 (dq, J=14.4, 7.3 Hz, 1H), 0.66 (t, J=7.4 Hz, 3H); $^{13}C$ NMR (101 MHz, $CD_3OD$) δ 156.9, 147.1, 134.2, 112.2, 102.4, 89.3, 83.1, 77.9, 72.8, 63.7, 31.2, 8.4; HRMS (APCI−) calcd for $C_{13}H_{17}N_4O_4$ $[M-H]^-$ 293.1255, found 293.1271 (error 5.4 ppm). The anomeric stereochemistry was determined by NMR analysis and the structure was confirmed by 2D-NOESY experiments.

4-Amino-7-(1'-vinyl-2',3',5'-trihydroxy-β-D-ribofuranosyl)pyrrolo[2,1-f][1,2,4]triazine (10) and (R)-1-((2S,3S)-4-(4-aminopyrrolo[2,1-f][1,2,4]triazin-7-yl)-3-hydroxy-3,6-dihydro-2H-pyran-2-yl)ethane-1,2-diol (33)

The title compounds were prepared from 32β (78 mg, 0.14 mmol, 1.00 equiv) using the general procedure 1.

Purification by flash chromatography (0-20% MeOH/EtOAc) afforded 10 (17 mg, 42%) and 33 (12 mg, 30%) as off-white solids. Although compound 10 has been disclosed; no physical or spectroscopic characterization data was reported, thus we have provided complete characterization data.

Data for 10: $R_f$=0.2 (15% MeOH/EtOAc); $[\alpha]^{23}_D$ −27 (c 0.10, MeOH); $^1$H NMR (600 MHz, $CD_3OD$) δ 7.81 (s, 1H), 6.94 (d, J=4.6 Hz, 1H), 6.79 (d, J=4.5 Hz, 1H), 6.60 (dd, J=17.3, 10.7 Hz, 1H), 5.31-5.13 (m, 2H), 4.78 (d, J=5.4 Hz, 1H), 4.10 (ddd, J=7.4, 5.0, 2.8 Hz, 1H), 4.01 (t, J=5.9 Hz, 1H), 3.86 (dd, J=12.0, 2.8 Hz, 1H), 3.72 (dd, J=12.0, 4.9 Hz, 1H); $^{13}$C NMR (151 MHz, $CD_3OD$) δ 156.0, 145.5, 136.9, 134.8, 115.6, 112.6, 104.1, 86.8, 84.6, 75.8, 73.1, 64.1; FTIR ($cm^{-1}$) 3353, 2974, 2885, 1647, 1608, 1407, 1269, 1086, 1045; HRMS (ESI-TOF) m/z: $[M+H]^+$: calcd for $C_{13}H_{17}N_4O_4$ 293.1205; found 293.1218. The anomeric stereochemistry was determined by NMR analysis and the structure was confirmed by a 2D-NOESY experiment. Key 2D-NOESY correlations of [H4'-1'-vinyl], [H5'—H8], [H3'—H8] and [H2'—H8] were observed.

Data for 33: $R_f$=0.25 (15% MeOH/EtOAc); $[\alpha]^{23}_D$ −45 (c 0.050, MeOH); $^1$H NMR (600 MHz, $CD_3OD$) δ 7.80 (s, 1H), 6.91-6.87 (m, 2H), 6.81 (d, J=4.6 Hz,

34

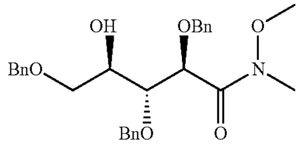

1H), 4.90 (d, J=4 Hz, 1H), 4.40-4.30 (m, 2H), 3.91 (td, J=6.3, 3.3 Hz, 1H), 3.81 (dd, J=11.7, 3.3 Hz, 1H), 3.73-3.63 (m, 2H); $^{13}$C NMR (151 MHz, $CD_3OD$) δ157.1, 147.9, 130.4, 129.7, 128.3, 116.1, 112.2, 103.3, 80.4, 73.1, 65.0, 64.8, 64.6; FTIR ($cm^{-1}$) 3319, 2916, 1651, 1612, 1518, 1463, 1267; HRMS (ESI-TOF) m/z: $[M+H]^+$ calcd for $C_{13}H_{17}N_4O_4$ 293.1205; found 293.1212.

Synthesis of (2R,3R,4R)-2,3,5-O-tris(Benzyl)-4-hydroxy-N-methoxy-N-methylpentanamide (34)

A solution of 2,3,5-O-tribenzylribonolactone 25 (0.50 g, 1.20 mmol,

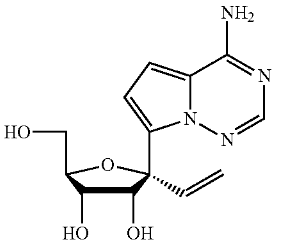

+

10

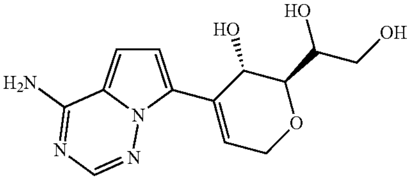

33

1.20 equiv) and N,O-dimethylhydroxylamine hydrochloride (0.18 g, 1.80 mmol, 1.50 equiv) in THF (5 mL) was cooled to −15° C. using a low temperature reaction bath (Eyela PSL-1820). Isopropylmagnesium chloride (2.00 M solution in THF, 1.8 mL, 3.60 mmol, 3.00 equiv) was added slowly to the reaction mixture and then the reaction temperature was set to −20° C. for 4 h. The solution was quenched with saturated aqueous $NH_4Cl$ solution (2 mL) and extracted with EtOAc. The combined organic phases were washed with water, brine, and then dried over anhydrous $Na_2SO_4$. The combined organic fraction was concentrated under reduced pressure. Purification using flash chromatography

35

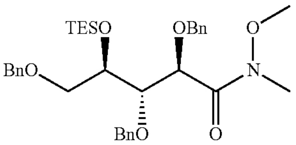

(10-60% EtOAc/hexanes) afforded the title compound (335 mg, 59%) as a colorless oil. $R_f$=0.3 (30% EtOAc/Hexane); $[\alpha]^{23}_D$ +89 (c 0.12, $CHCl_3$); $^1$H NMR (400 MHz, $CDCl_3$) δ 7.35-7.24 (m, 13H), 7.22-7.16 (m, 2H), 4.68-4.63 (m, 2H), 4.56-4.45 (m, 4H), 4.42 (d, J=11.7 Hz, 1H), 4.18 (q, J=5.1 Hz, 1H), 3.91 (t, J=5.8 Hz, 1H), 3.62 (d, J=4.6 Hz, 2H), 3.45 (s, 3H), 3.16 (s, 3H); $^{13}$C NMR (101 MHz, $CDCl_3$) (5173.7, 138.3, 138.1, 137.3, 128.4, 128.4, 128.3, 128.3, 128.1, 128.0, 128.0, 127.9, 127.8, 127.7, 81.8, 79.7, 75.4, 73.5, 72.0, 71.1, 71.0, 61.2, 31.4; FTIR ($cm^{-1}$) 3005, 2870, 1779, 1105, 1026; HRMS (ESI-TOF) m/z: $[M—C_2H_6NO]^+$ calcd for $C_{26}H_{27}O_5$ 419.1853; found 419.1856. The $^1$H and $^{13}$C NMR in DMSO-$d_6$ matched the reported data.

Synthesis of (2R,3R,4R)-2,3,5-O-tris(Benzyl)-4-O-triethylsilyl-N-methoxy-N-methylpentanamide (35)

To a suspension of Weinreb amide 34 (0.30 g, 0.63 mmol, 1.00 equiv) in $CH_2Cl_2$ (0.5 M) at −78° C. was added 2,6-lutidine (0.12 mL, 0.95 mmol, 1.50 equiv). After 5 min of stirring at −78° C., TESOTf (0.17 mL, 0.70 mmol, 1.10 equiv) was added slowly to the reaction mixture and the reaction was stirred for 2 h at −78° C. After the consumption of 34 as indicated by TLC (30% EtOAc; $R_f$=0.2), the solution was quenched with saturated aqueous $NaHCO_3$ (5 mL). The crude mixture was diluted with EtOAc and washed consecutively with water, saturated aqueous $CuSO_4$ and brine. The organic phase was separated, dried over anhydrous $Na_2SO_4$ and then concentrated under reduced pressure. Purification by silica gel flash chromatography (10-40% EtOAc/hexane) afforded the title compound 35 (270 mg, 72%) as a colorless oil. $R_f$=0.3 (20% EtOAc/hexane); $[\alpha]^{23}_D$+14 (c 0.62, $CHCl_3$); $^1$H NMR (400 MHz, $CDCl_3$) δ 7.31-7.23 (m, 15H), 4.74 (d, J=11.1 Hz, 2H), 4.57 (d, J=11.7 Hz, 1H), 4.49-4.40 (m, 4H), 4.31 (t, J=5.9 Hz, 1H), 3.96 (d, J=9.2 Hz, 1H), 3.72 (dd, J=9.8, 5.3 Hz, 1H), 3.52 (dd, J=9.8, 6.3 Hz, 1H), 3.41 (s, 3H), 3.12 (s, 3H), 0.96 (t, J=7.9 Hz, 9H), 0.63 (q, J=7.9 Hz, 6H); $^{13}$C NMR (101 MHz, $CDCl_3$) δ 172.1, 138.7, 138.6, 137.7, 128.3, 128.2, 128.1, 128.0, 128.0, 127.7, 127.6, 127.4, 82.7, 81.8, 74.5, 73.2, 72.3, 72.2, 72.0, 61.2, 32.0, 7.0, 5.0; FTIR ($cm^{-1}$) 3065, 2953, 2875, 1666, 1455, 1092; HRMS (ESI-TOF) m/z: $[M+H]^+$ calcd for $C_{34}H_{48}NO_6Si$ 594.3245; found 594.3214.

(3R,4S,5R)-3,4,6-O-tris(Benzyl)-1,1-difluoro-5-[(triethylsilyl)oxy]hexan-2-one (36)

To a stirring solution of 35 (3.70 g, 6.23 mmol, 1.00 equiv) in THF (20 mL) at 0° C. was added $TMSCHF_2$ (0.9 mL, 7.48 mmol, 1.20 equiv). After 10 min of stirring at 0° C., 1.00 M tBuOK in THF (9 mL, 9.34 mmol, 1.50 equiv) was added slowly to the reaction mixture and the reaction was stirred for another 4 h

36

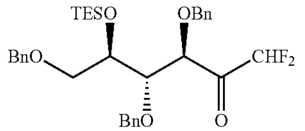

at 0° C. After the consumption of 35 as indicated by TLC (10% EtOAc; $R_f$=0.5), the solution was quenched with saturated aqueous $NH_4Cl$ (10 mL). The reaction mixture was diluted with $Et_2O$, washed consecutively with water and then brine. The organic phase was separated, dried over anhydrous $Na_2SO_4$ and then concentrated under reduced pressure. Purification by silica gel flash chromatography (5% EtOAc/hexane) afforded the title compound (1.60 g, 82%) as a colorless semisolid. $R_f$=0.5 (10% EtOAc/hexane); $[\alpha]^{23}_D$ +24 (c 0.18, $CHCl_3$); $^1H$ NMR (400 MHz, $CDCl_3$) δ 7.34-7.28 (m, 13H), 7.20-7.17 (m, 2H), 5.93 (t, J=53.8 Hz, 1H), 4.66-4.57 (m, 3H), 4.52-4.41 (m, 4H), 4.13 (t, J=4.7 Hz, 1H), 4.02 (t, J=5.1 Hz, 1H), 3.60 (dd, J=9.8, 4.7 Hz, 1H), 3.53 (dd, J=9.9, 4.6 Hz, 1H), 0.93 (t, J=7.9 Hz, 9H), 0.61 (q, J=7.9 Hz, 6H); $^{13}C$ NMR (101 MHz, $CDCl_3$) δ 198.3, 198.1, 198.1, 197.9, 138.1, 137.3, 137.0, 128.6, 128.5, 128.4, 128.4, 128.1, 128.1, 128.0, 128.0, 127.9, 127.7, 111.4, 108.9, 106.4, 81.6, 73.7, 73.5, 73.21, 71.2, 71.1, 6.8, 4.9; $^{19}F$ NMR (376 MHz, $CDCl_3$) δ −131.2 (dd, $^2J_{F,F}$=308.3 Hz, $^2J_{F,H}$=53.7 Hz), −129.9 (dd, $^2J_{F,F}$=308.6 Hz, $^2J_{F,H}$=53.7 Hz); FTIR ($cm^{-1}$) 2924, 2877, 1757, 1455, 1252; HRMS (ESI-TOF) m/z: $[M+H]^+$ calcd for $C_{33}H_{43}F_2O_5Si$ 585.2803; found 585.2794.

Synthesis of (3S,4R,5R)-2-(4-Aminopyrrolo[2,1-f][1,2,4]triazin-7-yl)-3,4,6-O-tribenzyl-1,1-difluoro-5-[(triethylsilyl)oxy]hexan-2-ol (37)

A suspension of 7-bromo-4-amino-pyrrolo[2,1-f][1,2,4]-triazine 24 (0.65 g, 3.02 mmol, 1.30 equiv), NaH (0.31 g, 6.04 mmol, 2.60 equiv), and 1,2-bis(chlorodimethylsilyl) ethane (0.65 g, 3.48 mmol, 1.30 equiv) in THF (40 mL) at 25° C. was stirred for 20 min. The reaction mixture was cooled down to −78° C. and then 1.60 M n-BuLi in hexane (6.20 mL, 9.99 mmol, 3.30 equiv) was slowly added down the side of the flask over 15 min. The reaction was stirred at −78° C. for a

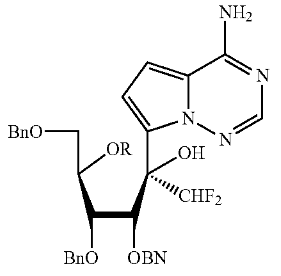

37a: major

+

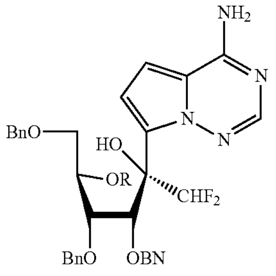

37b: minor

R = TES further 15 min, then a solution of difluoromethylketone 36 (1.36 g, 2.33 mmol, 1.00 equiv) in THF (10 mL) was added dropwise down the side of the flask. After 1 h, when TLC indicated complete consumption of 24, the reaction mixture was quenched with glacial acetic acid (0.6 mL, 10.0 mmol, 2.00 equiv) at −78° C. and stirred for 10 min, warmed to 25° C. and concentrated under reduced pressure. The residue was diluted with EtOAc, and then washed consecutively with saturated aqueous $NH_4Cl$, $H_2O$, and brine. The organic phase was separated, dried ($MgSO_4$), filtered and concentrated under reduced pressure. Purification by silica gel flash chromatography (0-45% EtOAc/hexane) afforded the title compound (0.90 g, 53%) as a white semi-solid as a 1.2:1 mixture of diastereomers. The two diastereomers were separated by normal phase preparative HPLC using 10% isopropanol/n-hexane (isocratic).

Data for major diastereomer (37a): HPLC ($t_R$=12.29 min; k'=3.91); $R_f$=0.3 (60% EtOAc/Hexane); $[O]^{23}_D$ −8.2 (c 0.17, $CHCl_3$); $^1H$ NMR (600 MHz, $CDCl_3$) δ 7.71 (s, 1H), 7.37-7.27 (m, 1 OH), 7.18-7.16 (m, 3H), 6.91-6.86 (m, 2H), 6.61 (d, J=4.6 Hz, 1H), 6.53 (d, J=4.6 Hz, 1H), 6.40 (t, J=56.3 Hz, 1H), 5.83 (br s, 2H), 4.83 (d, J=10.8 Hz, 1H), 4.62 (t, J=8.4 Hz, 2H), 4.56-4.45 (m,

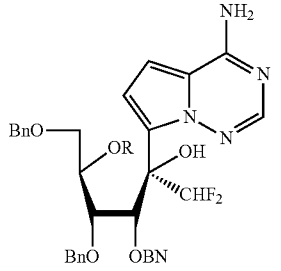

Major isomer
37a: R = TES

3H), 4.34 (td, J=5.6, 2.1 Hz, 1H), 4.26 (d, J=11.3 Hz, 1H), 3.94 (dd, J=7.1, 2.1 Hz, 1H), 3.80 (dd, J=9.6, 5.1 Hz, 1H), 3.54 (dd, J=9.6, 5.8 Hz, 1H), 0.89 (t, J=8.0 Hz, 9H), 0.56 (qd, J=7.8, 3.3 Hz, 6H); $^{13}C$ NMR (101 MHz, $CDCl_3$) δ 155.2, 155.1, 145.7, 138.5, 138.4, 137.8, 128.4, 128.3, 128.1, 128.0, 127.8, 127.7, 127.5, 127.1, 127.0, 126.7, 118.3, 115.9, 114.3, 113.4, 111.9, 100.7, 82.1, 81.3, 78.2, 78.0, 74.8, 73.3, 73.3, 72.7, 72.4, 6.9, 4.9; $^{19}F$ NMR (376 MHz, $CDCl_3$) δ −125.9 (dd, $^2J_{F,F}$=282 Hz, $^2J_{F,H}$=56.4 Hz), −136.5 (dd, $^2J_{F,F}$=278.2 Hz, $^2J_{F,H}$=56.4 Hz); FTIR ($cm^{-1}$) 3032, 2875, 2912, 1606, 1455, 1069; HRMS (ESI-TOF) m/z: $[M+H]^+$ calcd for $C_{39}H_{49}F_2N_4O_5Si$ 719.3396; found 719.3398.

Data of minor diastereomer 37b: ($t_R$=13.92 min; k'=4.56); $R_f$=0.3 (60% EtOAc/hexane); $[\alpha]^{23}_{\alpha}$+2.4 (c 0.23, $CHCl_3$); $^1H$ NMR (600 MHz, $CDCl_3$) δ 7.66 (s, 1H), 7.36 (br s, 1H), 7.24-7.14 (m, 8H), 7.12 (dd, J=5.1, 1.9 Hz, 3H), 7.10-7.06 (m, 2H), 6.91-6.84 (m, 2H), 6.76 (d, J=4.6 Hz, 1H), 6.45 (d, J=4.6 Hz, 1H), 6.19 (t, J=55.5 Hz, 1H), 5.72 (br s, 2H), 4.69 (d, J=11.4 Hz, 1H), 4.50 (d, J=10.8 Hz, 1H), 4.37 (q, J=12.0 Hz, 2H), 4.30 (d, J=11.4 Hz, 1H), 4.25 (d,

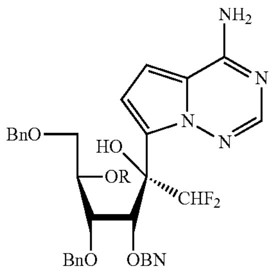

37b: minor
R = TES

J=6.8 Hz, 1H), 4.20 (tt, J=5.4, 2.2 Hz, 1H), 3.94 (ddd, J=6.9, 3.1, 1.5 Hz, 1H), 3.85 (d, J=10.8 Hz, 1H), 3.65 (ddd, J=9.7, 4.7, 1.4 Hz, 1H), 3.47 (ddd, J=9.7, 5.7, 1.3 Hz, 1H), 0.83 (t, J=6 Hz 9H), 0.54-0.45 (m, 6H); t$^3$C NMR (101 MHz, $CDCl_3$) δ 155.1, 145.6, 138.5, 138.3, 138.0, 128.3, 128.3, 128.1, 127.8, 127.5, 127.5, 127.3, 127.1, 126.7, 118.2, 115.7, 114.2, 113.3, 111.3, 100.8, 81.8, 81.5, 79.7, 79.5, 79.3, 74.3, 73.4, 73.2, 72.9, 72.3, 6.9, 4.9; $^{19}$F NMR (376 MHz, $CDCl_3$) δ −129.6 (dd, $^2J_{F,F}$=278.2 Hz, $^2J_{F,H}$=56.4 Hz), −130.0 (dd, $^2J_{F,F}$=278.2 Hz, $^2J_{F,H}$=52.6 Hz); FTIR ($cm^{-1}$) 2952, 2875, 1604, 1474, 1453, 1254; HRMS (ESI-TOF) m/z: [M+H] calcd for $C_{39}H_{49}F_2N_4O_5Si$ 719.3396; found 719.3398.

Synthesis of (2S,3S,4S,5R)-2-(4-Aminopyrrolo[2,1-f][1,2,4]triazin-7-yl)-3,4,6-tris(benzyloxy)-1,1-difluorohexane-2,5-dioi (38a)

To a stirring solution of 37a (0.30 g, 0.41 mmol, 1.00 equiv) in THF (4 mL) at 0° C. was added 1.00 M TBAF in THF (0.6 mL, 0.62 mmol, 1.50 equiv). After the addition of TBAF, the reaction mixture was warmed to 25° C. and stirred for 1 h. The solution was quenched with saturated aqueous $NH_4Cl$ (2 mL). After the consumption of 37a as indicated by TLC, the reaction mixture was diluted with $Et_2O$ 38a

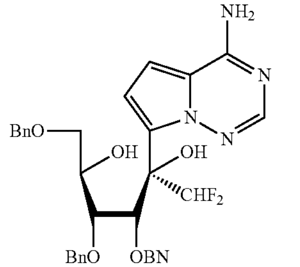

and washed consecutively with water and brine. The organic phase was separated, dried over anhydrous $Na_2SO_4$ and then concentrated under reduced pressure. Purification by silica gel flash chromatography (30-85% EtOAc/hexane) afforded the title compound (242 mg, 96%) as a white solid. $R_f$=0.2 (65% EtOAc/hexane); $[\alpha]^{23}_D$ −17 (c 0.13, MeOH); $^1$H NMR (400 MHz, $CD_3OD$) δ7.70 (s, 1H), 7.39-7.13 (m, 13H), 6.96-6.89 (m, 3H), 6.80 (d, J=4.6 Hz, 1H), 6.39 (dd, J=56.9, 55.0 Hz, 1H), 5.14 (d, J=2.2 Hz, 1H), 4.89 (s, 1H), 4.69 (d, J=11.0 Hz, 1H), 4.48-4.35 (m, 2H), 4.23 (d, J=11.3 Hz, 1H), 4.16-4.10 (m, 1H), 4.03 (d, J=11.3 Hz, 1H), 3.68 (dd, J=10.2, 2.7 Hz, 1H), 3.51 (td, J=5.5, 3.3 Hz, 2H); $^{13}$C NMR (101

MHz, $CD_3OD$) δ 157.0, 147.2, 139.5, 139.1, 139.1, 129.5, 129.2, 129.2, 129.2, 129.1, 128.8, 128.8, 128.6, 128.5, 128.5, 119.2, 116.7, 116.4, 114.3, 113.3, 103.2, 81.5, 81.4, 78.6, 78.6, 78.4, 75.9, 74.1, 73.6, 72.6, 70.5; $^{19}$F NMR (376 MHz, $CD_3OD$) δ −126.2 (dd, 2$J_{F,F}$=278.2 Hz, $^2J_{F,H}$=52.6 Hz), −134.7 (dd, $^2J_{F,F}$=278.2 Hz, $^2J_{F,H}$=56.4 Hz); FTIR ($cm^{-1}$) 3337, 2972, 2870, 1606, 1455, 1071, 1047; HRMS (ESI-TOF) m/z: $[M+Na]^+$ calcd for $C_{33}H_{34}F_2N_4O_5Na$ 627.2389; found 627.2419.

(2R,3S,4S,5R)-2-(4-Aminopyrrolo[2,1-f][1,2,4]triazin-7-yl)-3,4,6-tris(benzyloxy)-1,1-difluorohexane-2,5-diol (38b)

To a stirring solution of 37b (0.28 g, 0.39 mmol, 1.00 equiv) in THF (4 mL) at 0° C. was added 1.0 M TBAF in THF (0.58 mL, 0.58 mmol, 1.50 equiv).

38b

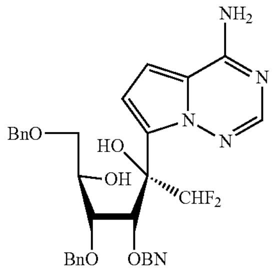

After the addition of TBAF, the reaction mixture was warmed to 25° C. and stirred for 2 h. The solution was quenched with saturated aqueous $NH_4Cl$ (2 mL) After the consumption of 37b as indicated by TLC (65% EtOAc/hexane; $R_f$=0.4), the reaction mixture was diluted with $Et_2O$ and washed consecutively with water and brine. The organic phase was separated, dried over anhydrous $Na_2SO_4$ and then concentrated under reduced pressure. Purification by silica gel flash chromatography (30-85% EtOAc/hexane) afforded the title compound (221 mg, 94%) as a white solid. $R_f$=0.2 (65% EtOAc/hexane); $[\alpha]^{23}_D$+56 (c 0.10, $CHCl_3$); $^1$H NMR (400 MHz, $CD_3OD$) δ7.61 (s, 1H), 7.34-7.22 (m, 8H), 7.20-7.15 (m, 2H), 7.12 (d, J=6.8 Hz, 3H), 6.89-6.80 (m, 3H), 6.78 (d, J=4.6 Hz, 1H), 6.43 (t, J=56 Hz, 1H), 4.64 (d, J=2.4 Hz, 1H), 4.55 (dd, J=11.2, 2.2 Hz, 2H), 4.52-4.43 (m, 3H), 4.17 (d, J=11.1 Hz, 1H), 4.12-4.06 (m, 2H), 3.74 (dd, J=10.1, 2.5 Hz, 1H), 3.65 (dd, J=10.1, 5.3 Hz, 1H); $^{13}$C NMR (101 MHz, $CD_3OD$) δ 157.1, 147.0, 139.6, 139.4, 139.0, 129.3, 129.2, 129.0, 128.9, 128.9, 128.8, 128.6, 128.5, 128.5, 118.7, 116.2, 115.9, 113.8, 112.4, 102.7, 81.5, 81.4, 79.5, 79.3, 79.1, 75.1, 74.2, 74.1, 72.8, 71.1; $^{19}$F NMR (376 MHz, $CD_3OD$) δ −131.3 (dd, $^2J_{F,F}$=278.2, $^2J_{F,H}$=56.4 Hz), −132.2 (dd, $^2J_{F,F}$=259.4, $^2J_{F,H}$=56.4 Hz); FTIR ($cm^{-1}$) 3356, 2976, 2899, 1610, 1455, 1267, 1047, 879; HRMS (ESI-TOF) m/z: $[M+Na]^+$ calcd for $C_{33}H_{34}F_2N_4O_5Na$ 627.2389; found 627.2419.

Synthesis of 4-Amino-7-(1-difluoromethyl-2',3',5-trihydroxy-β-D-ribofuranosylpyrrolo[2,1-f][1,2,4]triazine (11)

To a stirring solution of 38a (0.10 g, 0.17 mmol, 1.00 equiv) in dichloromethane (2 mL) was added methanesulfonic acid (0.08 mL, 1.32 mmol, 8.00 equiv) at 25° C. The reaction mixture was warmed to 35° C. and stirred for 4 h. The reaction was quenched with $Et_3N$ (0.10 mL) and the mixture was

11

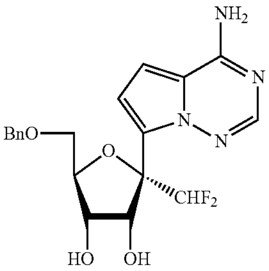

concentrated under vacuum. Purification using silica gel flash chromatography (0-10% EtOAc/MeOH) afforded the title compound (36 mg, 62%) as a white solid. $R_f$=0.3 (8% MeOH/EtOAc); $[\alpha]^{23}_D$+12 (c 0.33, MeOH); $^1$H NMR (600 MHz, $CD_3OD$) δ7.78 (s, 1H), 6.90 (d, J=4.6 Hz, 1H), 6.73 (d, J=4.6 Hz, 1H), 6.25 (t, J=54 Hz, 1H), 4.54 (dd, J=4.3, 1.7 Hz, 1H), 4.16 (q, J=5.1 Hz, 1H), 4.12 (t, J=4.8 Hz, 1H), 4.05 (dd, J=9.0, 5.1 Hz, 1H), 3.74 (dd, J=9.0, 4.9 Hz, 1H); $^{13}$C NMR (101 MHz, $CD_3OD$) δ 157.2, 147.3, 125.4, 119.5, 117.0, 116.1, 114.6, 112.6, 103.0, 86.1, 86.1, 78.3, 78.1, 77.9, 74.0, 73.4, 72.6; $^{19}$F NMR (376 MHz, $CD_3OD$) δ −128.4 (dd, $^2J_{F,F}$=263.2 Hz, $^2J_{F,H}$=56.4 Hz), −137.2 (dd, $^2J_{F,F}$=263.2 Hz, $^2J_{F,H}$=56.4 Hz); FTIR ($cm^{-1}$) 3350, 2927, 2834, 1608, 1451, 1086, 1025 HRMS (ESI-TOF) m/z: $[M+H]^+$ calcd for $C_{12}H_{15}F_2N_4O_4$ 317.1017; found 317.1010. The anomeric stereochemistry was determined by NMR analysis and the structure was confirmed by a 2D-NOESY experiment. Key 2D-NOESY correlations of [H5'—H8], [H3'—H8], [H2'—H8], [H3'-1'-$CHF_2$] and [H2'-1'-$CHF_2$] were observed.

4-Amino-7-(1'-difluoromethyl-2',3',5-trihydroxy-β-D-ribofuranosyl) pyrrolo [2,1-f][1,2,4]triazine (11β) and 4-Amino-7-(1-difluoromethyl-2',3,5'-trihydroxy-β-D-lyxonofuranosyl)pyrrolo[2,1-f][1,2,4]triazine (4'-epi-11β)

To a stirring solution of 38b (0.10 g, 0.17 mmol, 1.00 equiv) in dichloromethane (2 mL) was added methanesulfonic acid (0.08 mL, 1.32 mmol, 8.00 equiv) at 25° C. The reaction mixture was warmed to 35° C. and stirred for 4 h. The reaction was quenched with $Et_3N$ (0.1 mL) and the solution was

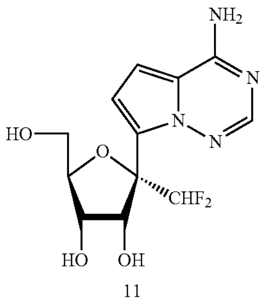

11

+

-continued

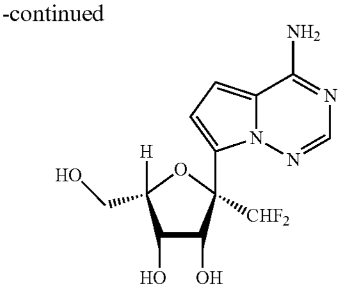

4'-epi-11β concentrated under vacuum. Purification using silica gel flash chromatography (0-15% EtOAc/MeOH) afforded a mixture of compound 11β and 4'-epi-11β (1:1 mixture; 37 mg, 72%) as a white solid. The diastereomers were separated by normal-phase preparative HPLC using 35% isopropanol/n-heptane (isocratic).

Data of 4'-epi-11β: HPLC ($t_R$=10.01 min; k'=3.00); $[\alpha]^{23}_D$ −4.8 (c 0.080, MeOH); $^1$H NMR (600 MHz, $CD_3OD$) δ 7.78 (s, 1H), 6.90 (d, J=4.6 Hz, 1H), 6.74 (d, J=4.6 Hz, 1H), 6.47 (t, J=55.3 Hz, 1H), 4.45 (d, J=5.4 Hz, 1H), 4.35-4.33 (m, 1H), 3.81 (q, J=5.0 Hz, 2H), 3.61 (dd, J=10.1, 6.1 Hz, 1H); $^{13}$C NMR (151 MHz, $CD_3OD$) δ 157.2, 147.4, 127.5, 117.7, 116.1, 116.1, 114.5, 112.5, 103.0, 85.5, 78.2, 78.1, 77.9, 73.5, 72.6, 72.6; $^{19}$F NMR (376 MHz, $CD_3OD$) δ −132.1 (dd, $^2J_{F,F}$=282 Hz, $^2J_{F,H}$=52.6 Hz), −135.7 (dd, $^2J_{F,F}$=282 Hz, $^2J_{F,H}$=56.4 Hz); FTIR ($cm^{-1}$) 3367, 2976, 2890, 1608, 1269, 1086, 1045; HRMS (ESI-TOF) m/z: $[M+H]^+$ calcd for $C_{12}H_{15}F_2N_4O_4$ 317.1017; found 317.1010. The anomeric stereochemistry was determined by NMR analysis and the structure was confirmed by a 2D-NOESY experiment. Key 2D-NOESY correlations of [H2'—H8], [H3'—H8], [H4'—H8] and [H2'-1'-$CHF_2$] were observed.

Synthesis of (3R,4S,5R)-3,4,6-O-tris(Benzyl)-1-fluoro-5-[(triethylsilyl)oxy]hexan-2-one (39)

A solution of 35 (0.70 g, 1.18 mmol, 1.50 equiv) in a mixture of 1:1 THF and $Et_2O$ (12 mL; 0.09 M) was cooled to −78° C. To the reaction flask, fluoroiodomethane (0.05 mL, 0.78 mmol, 1.00 equiv) and MeLi (1 mL, 1.57 mmol, 2.00 equiv) were consecutively added slowly at −78° C. and stirred for 5 min. The

39

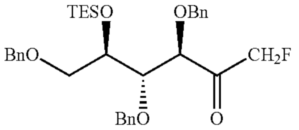

reaction was quenched with the addition of saturated aqueous $NH_4Cl$ (2 mL). The mixture was warmed to 25° C. and then diluted with $Et_2O$. The organic layer was washed consecutively with water and brine. The organic phase was separated, dried over anhydrous $Na_2SO_4$ and then concentrated under reduced pressure. Purification by silica gel flash chromatography (5% EtOAc/hexane) afforded the title compound (104 mg, 23%) as a colorless oil. $R_f$=0.3 (5% EtOAc/hexane); $[\alpha]^{23}_D$ +8.1 (c 0.32, $CHCl_3$); $^1$H NMR (400 MHz, $CDCl_3$) δ 7.38-7.26 (m, 13H), 7.24-7.17 (m, 2H), 5.13-4.98 (m, 1H), 4.98-4.84 (m, 1H), 4.60 (d, J=11.1 Hz, 3H), 4.58-4.46 (m, 3H), 4.36 (dt, J=3.8, 1.7 Hz, 1H), 4.10 (dtd, J=5.9, 4.0, 1.6 Hz, 1H), 4.00 (ddd, J=6.1, 4.1, 1.6 Hz, 1H), 3.59 (dt, J=4.0, 1.8 Hz, 2H), 0.94 (td, J=7.9, 1.7 Hz, 9H), 0.63 (qd, J=8.0, 1.6 Hz, 6H); $^{13}C$ NMR (101 MHz, $CDCl_3$) δ 204.6, 204.4, 138.1, 137.8, 137.1, 128.6, 128.5, 128.4, 128.4, 128.2, 128.1, 128.0, 128.0, 127.9, 127.9, 127.7, 86.0, 84.2, 82.0, 74.2, 73.5, 73.0, 71.5, 71.1, 6.9, 5.05; $^{19}F$ NMR (376 MHz, $CDCl_3$) δ −233.6 (t, $^2J_{F,H}$=45 Hz); FTIR ($cm^{-1}$) 3032, 2952, 2911, 2877, 1727, 1455, 1207, 1099, 1026; HRMS (ESI-TOF) m/z: $[M+K]^+$ calcd for $C_{33}H_{43}FO_5SiK$ 605.2495: found 605.2520.

Synthesis of (2R/S,3S,4R,5R)-2-(4-Aminopyrrolo[2,1-f][1,2,4]triazin-7-yl)-3,4,6-O-tris(benzyl)-1-fluoro-5-[(triethylsilyl)oxy]hexan-2-ol (40)

The suspension of 7-bromo-4-aminopyrrolo[2,1-f][1,2,4]triazine 24 (0.35 g, 1.60 mmol, 2.00 equiv) and NaH (60% in mineral; 0.13 g, 3.20 mmol, 4.00 equiv) was added 1,2-bis(chlorodimethylsilyl)ethane (0.35 g, 1.60 mmol, 2.00 equiv) in THF (40 mL) at 25° C. The reaction was stirred for 20 min, then cooled to −78° C. and 1.6 M n-BuLi in hexane (3.3 mL, 5.28 mmol, 6.60 equiv) was slowly

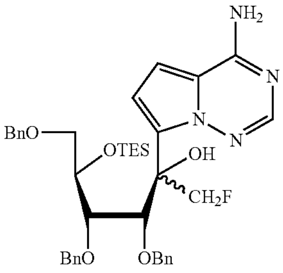

Isomeric mixture (1.2:1)

added down the side of the flask over 15 min. The reaction was stirred at −78° C. for a further 15 min, then a solution of monofluoromethylketone 39 (0.45 g, 0.80 mmol, 1.00 equiv) in THF (8 mL) was added dropwise down the side of the flask. After 40 min, when TLC indicated complete consumption of 24, the reaction mixture was quenched with glacial acetic acid (0.06 mL, 1.60 mmol, 2.00 equiv) at −78° C. and stirred for 10 min, warmed to 25° C. and concentrated under reduced pressure. The residue was diluted with EtOAc, and was washed consecutively with saturated aqueous $NH_4Cl$, $H_2O$, and brine. The organic phase was separated, dried ($MgSO_4$), filtered and concentrated under reduced pressure. Purification by silica gel flash chromatography (0-45% EtOAc/hexane) afforded the title compound (311 mg, 57%) as white semisolid as a 1.2:1 mixture of diastereomers. $R_f$=0.3 (40% EtOAc/hexane); $^1H$ NMR (400 MHz, $CDCl_3$) δ 7.59 (s, 1H), 7.32-7.14 (m, 14H), 7.01-6.86 (m, 2H), 6.83 (dd, J=11.6, 4.5 Hz, 1H), 5.07 (dd, J=46.8, 9.4 Hz, 1H), 4.92-4.73 (m, 1H), 4.73-4.65 (m, 1H), 4.56 (d, J=5.9 Hz, 1H), 4.51-4.35 (m, 3H), 4.33-4.16 (m, 2H), 4.00 (d, J=11.3 Hz, 1H), 3.83-3.61 (m, 2H), 3.52 (ddd, J=13.0, 9.5, 5.3 Hz, 1H), 0.98-0.78 (m, 9H), 0.58 (qd, J=8.2, 7.5, 2.6 Hz, 6H); $^{13}C$ NMR (101 MHz, $CD_3OD$) δ 156.6, 156.0, 146.7, 145.5, 139.5, 139.2, 138.9, 138.8, 132.3, 132.3, 129.8, 129.3, 129.2, 129.2, 129.2, 129.1, 129.1, 129.0, 128.9, 128.9, 128.7, 128.7, 128.6, 128.4, 116.1, 113.5, 112.9, 103.7, 103.4, 87.5, 85.7, 81.4, 80.9, 80.5, 79.8, 78.1, 77.9, 75.3, 74.7, 74.2, 74.1, 73.8, 73.1, 72.7, 70.9, 70.9, 70.0, 6.9, 6.5, 4.7; $^{19}F$ NMR (376 MHz, $CDCl_3$) δ −225.5 (t, $^2J_{F,H}$=45.1 Hz, minor isomer), −229.5 (t, $^2J_{F,H}$=45.1 Hz, major isomer); FTIR ($cm^{-1}$) 3367, 2974, 1673, 1455, 1276, 1086, 1047; HRMS (ESI-TOF) m/z: $[M+H-TES]^+$ calcd for $C_{33}H_{35}FN_4O_5$ 587.2664; found 587.2625.

(3S,4S,5R)-2-(4-Aminopyrrolo[2,1-f][1,2,4]triazin-7-yl)-3,4,6-O-tris(benzyl)-1-fluorohexane-2,5-diol (41)

To a stirring solution of 40 (0.10 g, 0.14 mmol, 1.00 equiv) in THF (4 mL) at 0° C. was added 1.00 M TBAF in THF (0.20 mL, 0.21 mmol, 1.50 equiv). After the addition of TBAF, the reaction mixture was warmed to 25° C. and stirred for 1 h. The solution was quenched with saturated aqueous $NH_4Cl$ (2 mL) After the consumption of 40 as indicated by TLC (65% EtOAc/hexane; $R_f$=0.4), the reaction mixture was diluted with $Et_2O$ and washed consecutively with water and

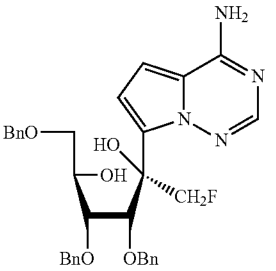

41a, major

+

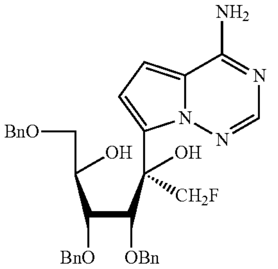

41b, minor brine. The organic phase was separated, dried over anhydrous $Na_2SO_4$ and then concentrated under reduced pressure. Purification by silica gel flash chromatography (30-85% EtOAc/hexane) afforded the title compound (80 mg, 96%) as a white solid. The two diastereomers were separated by normal phase prep-HPLC using 16% isopropanol/n-heptane (isocratic).

Data of major isomer 41a: HPLC ($t_R$=11.22 min; k'=3.48); $[\alpha]^{23}_D$ −23 (c 0.35, $CHCl_3$); $^1H$ NMR (400 MHz, $CD_3OD$) δ 7.72 (s, 1H), 7.39-7.13 (m, 14H), 6.95-6.83 (m, 3H), 6.80 (d, J=4.5 Hz, 1H), 5.31 (dd, J=46.3, 9.1 Hz, 1H), 4.99-4.91 (m, 1H), 4.85-4.70 (m, 2H), 4.59 (d, J=11.3 Hz, 1H), 4.50-4.34 (m, 2H), 4.12-4.00 (m, 2H), 3.80 (d, J=11.3 Hz, 1H), 3.65 (dd, J=10.2, 2.4 Hz, 1H), 3.46 (dd, J=10.1, 5.4 Hz, 1H), 3.42-3.37 (m, 1H); $^{13}C$ NMR (101 MHz, $CD_3OD$) δ 157.2, 147.5, 139.6, 139.0, 138.9, 132.0, 131.9, 129.8, 129.5, 129.3, 129.2, 129.2, 129.1, 129.1, 128.9, 128.8, 128.8, 128.6, 128.6, 128.5, 128.4, 116.3, 113.4, 102.9, 87.5, 85.7, 81.0, 80.9, 80.6, 80.5, 78.2, 78.0, 75.4, 74.1, 74.1, 73.2, 73.1, 72.7, 70.1; $^{19}F$ NMR (376 MHz, $CD_3OD$) δ −233.4 (t, J=48.8 Hz); FTIR ($cm^{-1}$) 3343, 3241, 2971, 2870, 1608, 1515, 1455, 1047; HRMS (ESI-TOF) m/z: $[M-H]^-$ calcd for $C_{33}H_{34}FN_4O_5$ 585.2519; found 585.2524.

Data of minor isomer 41b: HPLC ($t_R$=12.31 min; k'=3.92); $[\alpha]^{23}_D$ +4.5 (c 1.0, $CHCl_3$); $^1H$ NMR (400 MHz, $CD_3OD$) δ 7.61 (s, 1H), 7.35-7.23 (m, 10H), 7.11-7.04 (m, 3H), 6.88 (d, J=4.5 Hz, 1H), 6.79 (dd, J=9.9, 5.9 Hz, 3H), 4.95 (dd, $^2J_{F,H}$=44 Hz, $^2J_{H,H}$=8 Hz, 1H), 4.75 (dd, $^2J_{F,H}$=48 Hz, $^2J_{H,H}$=12 Hz, 1H), 4.68 (d, J=3.1 Hz, 1H), 4.62-4.51 (m, 4H), 4.45 (d, J=11.2 Hz, 1H), 4.15 (td, J=6.1, 2.8 Hz, 1H), 4.12-4.04 (m, 1H), 3.92 (dd, J=6.4, 3.1 Hz, 1H), 3.77 (dd, J=10.1, 2.9 Hz, 1H), 3.68 (dd, J=10.1, 5.7 Hz, 1H); $^{11}C$ NMR (101 MHz, $CD_3OD$) δ 156.6, 146.3, 139.6, 139.4, 139.0, 132.2, 132.1, 129.3, 129.1, 129.0, 129.0, 128.8, 128.6, 128.6, 128.4, 115.7, 112.7, 103.1, 86.9, 85.2, 81.6, 80.2, 78.6, 78.4, 74.8, 74.3, 73.9, 72.7, 71.1; $^{19}F$ NMR (376 MHz, $CD_3OD$) δ −228.7, (t, J=45.1 Hz); FTIR ($cm^{-1}$) 3326, 3213, 2925, 2864, 1606, 1476, 1455, 1252, 1088; HRMS (ESI-TOF) m/z: $[M-H]^-$ calcd for $C_{33}H_{34}FN_4O_5$ 585.2519; found 585.2524.

4-Amino-7-(1-fluoromethyl-2,3,5-trihydroxy-α-D-ribofuranosyl)pyrrolo[2,1-f][1,2,4]triazine (12α)

To a stirring solution of 41a (0.10 g, 0.17 mmol, 1.00 equiv) in dichloromethane (2 mL) was added methanesulfonic acid (0.08 mL, 1.32 mmol, 8.00 equiv) at 25° C. The reaction mixture was warmed to 35° C. and stirred for 4 h. The reaction was quenched with $Et_3N$ (0.10 mL) and the solution was

12α

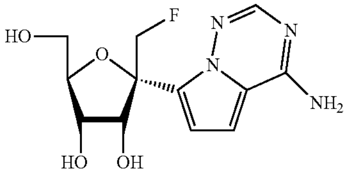

concentrated under vacuum. Purification using silica gel flash chromatography (0-15% EtOAc/MeOH) afforded the title compound (38 mg, 75%) as a white solid. $R_f$=0.3 (20% MeOH/EtOAc); $[\alpha]^{23}_D$ −59.3 (c 0.10, $CHCl_3$); $^1H$ NMR (600 MHz, $CD_3OD$) δ 7.99 (s, 1H), 7.36 (d, J=4.7 Hz, 1H), 7.01 (d, J=4.7 Hz, 1H), 4.94 (dd, $^2J_{H,F}$=48.0 Hz, $^2J_{H,H}$=6.0 Hz, 1H), 4.60 (d, J=4.9 Hz, 1H), 4.59 (dd, $^2J_{H,F}$=48.0 Hz, $^2J_{H,H}$=12.0 Hz, 1H), 4.09 (ddd, J=8.9, 4.9, 2.3 Hz, 1H), 4.05-4.00 (m, 1H), 3.92 (dd, J=12.0, 2.3 Hz, 1H), 3.71 (dd, J=12.0, 5.9 Hz, 1H); $^{13}C$ NMR (151 MHz, $CD_3OD$) δ 150.6, 137.2, 136.6, 136.6, 115.0, 113.4, 110.3, 88.7, 88.6, 86.4, 85.2, 83.6, 74.8, 74.8, 73.1, 73.1, 63.6; $^{19}F$ NMR (376 MHz, $CD_3OD$) δ −229.2 (t, J=48.8 Hz); FTIR ($cm^{-1}$) 3339, 974, 2891, 1656, 1269, 1088, 1045; HRMS (ESI-TOF) m/z: $[M+H]^+$ calcd for $C_{12}H_{16}FN_4O_4$ 299.1150; found 299.1165. The anomeric stereochemistry was determined by NMR analysis and the structure was confirmed by a 2D-NOESY experiment. Key 2D-NOESY correlations of [H4'—H8], [H3'-1'-$CH_2F$] and [H2'-1'-$CH_2F$] were observed.

4-Amino-7-(1'-fluoromethyl-2,3;5-trihydroxy-β-D-ribofuranosyl)pyrrolo[2,1-f][1,2,4]triazine (12β)

To a stirring solution of 41b (60 mg, 0.10 mmol, 1.00 equiv) in dichloromethane (2 mL) was added methanesulfonic acid (0.05 mL, 0.80 mmol, 8.00 equiv) at 25° C. The reaction mixture was warmed to 30° C. and stirred for 4 h. The reaction mixture was quenched with $Et_3N$ (0.05 mL) and the solution was concentrated under vacuum. Purification using silica gel flash chromatography (0-

12β

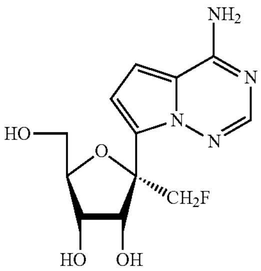

10% EtOAc/MeOH) afforded the title compound 12β(20 mg, 68%) as a white solid. $R_f$=0.3 (20% MeOH/EtOAc); $[\alpha]^{23}_D$ +52 (c 0.050, MeOH); $^1H$ NMR (600 MHz, CD3OD) δ 7.82 (s, 1H), 6.91 (d, J=6.0 Hz, 1H), 6.89 (d, J=6.0 Hz, 1H), 5.36 (dd, $^2J_{H,F}$=48.0 Hz, $^2J_{HH}$=12.0 Hz, 1H), 4.91 (dd, $^2J_{H,F}$=54.1 Hz, $^2J_{H,H}$=6.0 Hz, 1H), 4.65 (d, J=5.1 Hz, 1H), 4.10 (ddd, J=7.8, 5.2, 2.7 Hz, 1H), 3.95 (dd, J=7.7, 5.1 Hz, 1H), 3.88 (dd, J=12.1, 2.7 Hz, 1H), 3.73 (dd, J=12.1, 5.2 Hz, 1H); $^{13}C$ NMR (151 MHz, $CD_3OD$) δ 156.4, 146.3, 131.9, 116.1, 113.2, 103.5, 86.3, 85.3, 84.1, 83.9, 75.8, 72.4, 63.5; $^{19}F$ NMR (376 MHz, $CD_3OD$) δ −235.9 (t, J=48.8 Hz); FTIR ($cm^{-1}$) 3339, 2976, 2888, 1608, 1451, 1269, 1088, 1045; HRMS (ESI-TOF) m/z: $[M+H]^+$ calcd for $C_{12}H_{16}FN_4O_4$ 299.1150; found 299.1165. The anomeric stereochemistry was determined by NMR analysis and the structure was confirmed by a 2D-NOESY experiment Key 2D-NOESY correlations of [H5'—H8], [H3'—H8], [H2'—H8], and [H4'-1'-$CH_2F$] were observed.

Synthesis of (2R,3R,4R)-5-(4-Aminopyrrolo[2,1-f][1,2,4]triazin-7-yl)-1-[1,2,4-tris(benzyloxy)-3-hydroxybutyl]-1H-tetrazole (47)

To a suspension of 26 (0.12 g, 0.23 mmol, 1.00 equiv) in $CH_2Cl_2$ (10 mL) at −78° C. was added TfOH (40 μL, 0.46 mmol, 2.00 equiv) and the mixture was stirred for 10 min. Then, TMSOTf (90 μL, 0.48 mmol, 2.10 equiv) was slowly added and the reaction was stirred for an additional 30 min at −78° C. Thereafter,

47

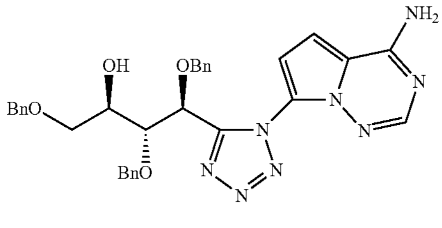

$TMSN_3$ (0.12 mL, 0.92 mmol, 4.00 equiv) was added dropwise and the reaction mixture was stirred for 3 h at −78° C. When TLC indicated the complete consumption of compound 26, the reaction was quenched with $Et_3N$ (1.50 mL) and warmed to 25° C. Solid $NaHCO_3$ (2.00 g) was added followed by slow addition of $H_2O$ (10 mL) and the reaction was stirred for 10 min. The organic layer was separated, dried ($Na_2SO_4$), filtered and concentrated under reduced pressure. Purification by silica gel flash chromatography (30-100% EtOAc/hexane) afforded the title compound (51 mg, 38%) as a white foamy solid. $R_f$=0.43 (60% EtOAc/hexane); $[\alpha]^{23}_D$ +11 (c 0.050, $CHCl_3$); $^1$H NMR (400 MHz, $CD_3OD$) δ7.71 (s, 1H), 7.37-7.19 (m, 11H), 7.11-7.01 (m, 2H), 6.90 (s, 2H), 6.73-6.64 (m, 2H), 4.63-4.46 (m, 5H), 4.43-4.31 (m, 3H), 4.07 (d, J=11.7 Hz, 1H), 3.72 (dd, J=10.7, 3.0 Hz, 1H), 3.58 (dd, J=10.7, 5.6 Hz, 1H); $^{13}$C NMR (101 MHz, $CD_3OD$) δ 157.0, 147.9, 139.5, 139.26, 139.25, 129.5, 129.4, 129.33, 129.30, 129.2, 129.16, 129.14, 129.13, 129.0, 128.9, 128.88, 128.84, 128.6, 128.5, 128.4, 127.9, 116.4, 115.1, 108.6, 102.5, 81.8, 81.2, 81.1, 74.5, 74.1, 73.7, 72.3; FTIR ($cm^{-1}$) 3030, 2860, 1602, 1518, 1474, 1097; HRMS (ESI+) calcd for $C_{32}H_{33}N_8O_4$ $[M+H]^+$ 593.2625, found 593.2622.

Synthesis of 2,3-O-Isopropylidene-D-ribonolactone (49)

To a stirring solution of D-ribonolactone 48 (2.00 g, 13.5 mmol, 1.00 equiv) in acetone (40 mL) was added p-TsOH·$H_2O$ (0.50 g, 2.70 mmol, 0.20 equiv) and 2,2-dimethoxypropane (5 mL, 40.5 mmol, 3.00 equiv) at 25° C. and the reaction mixture was stirred for overnight. After the consumption of lactone as indicated by TLC (40% EtOAc/hexane; $R_f$ 0.3), the reaction mixture was

49

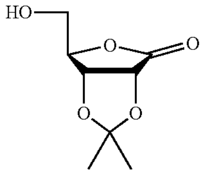

concentrated in vacuo. The crude mixture was diluted with EtOAc and washed consecutively with water and brine. The organic phase was separated, dried over anhydrous $Na_2SO_4$ and then concentrated under reduced pressure. Purification by silica gel flash chromatography (20-100% EtOAc/hexane) afforded the title compound 49 (2.28 g, 90%) as a white solid. $R_f$=0.3 (40% EtOAc/hexane); $[\alpha]^{23}_D$ −64 (c 0.49, $CHCl_3$); $^1$H NMR (400 MHz, $CD_3OD$) δ 4.82-4.61 (s, 2H), 4.61 (t, J=2.2 Hz, 1H), 3.78 (dd, J=12.0, 2.4 Hz, 1H), 3.74 (dd, J=12.4, 2.0 Hz, 1H), 1.42 (s, 3H), 1.37 (s, 3H); $^{13}$C NMR (101 MHz, $CD_3OD$) δ 176.9, 113.8, 84.5, 79.8, 76.9, 62.1, 27.0, 25.5; FTIR ($cm^{-1}$) 3464, 2991, 2933, 1764, 1379, 1075; HRMS (APCI+) calcd for $C_8H_{12}O_5$ $[M+H]^+$ 189.0757, found 189.0757.

Synthesis of 5-O-tert-Butyldimethylsilyl-2,3-O-isopropylidene-D-ribonolactone (50)

To a stirring solution of lactone 49 (1.00 g, 5.30 mmol, 1.00 equiv) in DMF (8 mL) was added imidazole (0.70 g, 10.6 mmol, 2.00 equiv) and TBSCI (1.20 g, 7.90 mmol, 1.50 equiv) at 25° C. and the reaction was stirred for 4 h. After the consumption of lactone as indicated by TLC (10% EtOAc/hexane; $R_f$=0.4), the reaction mixture was diluted with EtOAc and washed consecutively with cold water and brine. The organic phase was separated, dried over anhydrous $Na_2SO_4$ and then concentrated under reduced pressure. Purification by silica gel flash chromatography (0-40% EtOAc/hexane) afforded the title compound (1.55 g, 98%) as a white solid. $R_f$=0.4 (10% EtOAc/hexane); $[\alpha]^{23}_D$ −33.3 (c 0.16, $CHCl_3$); $^1$H NMR (400 MHz, $CDCl_3$) δ 4.75-4.68 (m, 2H), 4.59 (d, J=1.9 Hz, 1H), 3.88 (dd, J=11.3, 2.1 Hz, 1H), 3.79 (dd, J=11.3, 1.4 Hz, 1H), 1.46 (s, 3H), 1.38 (s, 3H), 0.87 (s, 9H), 0.05 (d, J=6.6 Hz, 6H); $^{13}$C NMR (101 MHz, $CDCl_3$) δ 174.3, 113.1,

50

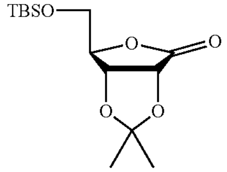

82.4, 75.9, 63.1, 26.9, 25.8, 25.7, 25.7, 18.3, −5.4, −5.6; FTIR ($cm^{-1}$) 2989, 2933, 2857, 1774, 1671, 1256, 1155; HRMS (ESI+) calcd for $C_{14}H_{26}O_5Si$ $[M+H]^+$ 303.1583, found 303.1581.

Synthesis of 4-Amino-7-(1-hydroxy-2',3-O-isopropylidene-5-O-tert-butyldimethylsilyl-α/β-D-ribofuranosyl)pyrrolo[2,1-f][1,2,4]triazine (51)

A suspension of 7-bromo-4-amino-pyrrolo[2,1-f][1,2,4]-triazine 24 (0.84 g, 3.90 mmol, 1.20 equiv), NaH (0.31 g, 7.80 mmol, 2.40 equiv), and 1,2-bis(chlorodimethylsilyl) ethane (0.84 g, 3.90 mmol, 1.20 equiv) in THF (40 mL) was stirred for 20 min at 25° C. Thereafter, the reaction mixture was cooled to −78° C. Then 1.60 M n-BuLi in hexane (8 mL, 12.87 mmol, 3.90 equiv) was slowly added down the side of the flask over 15 min and the reaction stirred for an additional 15

51

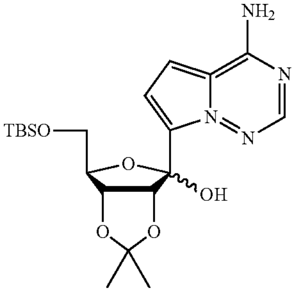

min. A solution of lactone 50 (1.00 g, 3.30 mmol, 1.00 equiv) in THF (5 mL) was added to the reaction dropwise down the side of the flask. After completion of the reaction as indicated by TLC, the reaction mixture was quenched with glacial acetic acid (0.40 mL, 6.60 mmol, 2.00 equiv). Then the reaction mixture was warmed to 25° C. and concentrated under reduced pressure. The residue was diluted with EtOAc and consecutively washed with saturated aqueous $NH_4Cl$, $H_2O$, and brine. The organic phase was separated, dried with $MgSO_4$, filtered and evaporated under reduced pressure. Purification by silica gel flash chromatography (0-70% EtOAc/hexane) afforded the title compound (1.15 g, 80%) as white semisolid. $R_f$=0.3 (40% EtOAc/Hexane); $^1$H NMR (400 MHz, $CD_3OD$) δ7.77 (s, 1H), 6.83-6.75 (m, 2H), 5.16 (d, J=6.0 Hz, 1H), 4.96-4.89 (m, 1H), 4.24 (dd, J=8.8, 5.2 Hz, 1H), 3.93-3.78 (m, 2H), 1.22 (d, J=13.0 Hz, 6H), 0.95 (s, 9H), 0.14 (s, 6H); $^{13}$C NMR (151 MHz, $CD_3OD$) δ 155.4, 147.1, 147.0, 129.1, 115.4, 114.5, 112.9, 111.4, 110.8, 104.9, 99.8, 99.6, 87.6, 86.7, 83.3, 82.7, 82.6, 64.9, 63.3, 50.9, 26.7, 26.1, 26.0, 25.9, 25.7, 18.5, −5.1, −5.2, −5.3; FTIR ($cm^{-1}$) 3417, 2953, 2858, 1643, 1606, 1485, 1127; HRMS (ESI+) calcd for $C_{20}H_{32}N_4O_5Si$ $[M+H]^+$ 437.2176, found 437.2189.

Synthesis of 4-Amino-7-(1'-methoxy-2',3'-O-isopropylidene-5'-hydroxy-D-ribofuranosyl)pyrolo [2,1-f][1,2,4]triazine (52)

To a stirring solution of 51 (0.22 g, 0.50 mmol, 1.00 equiv) in methanol (10.0 mL) was added two drops of concentrated sulfuric acid at 25° C.

52

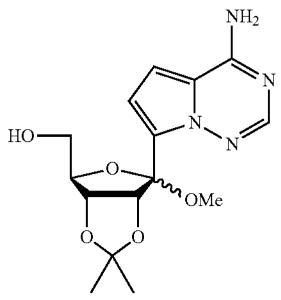

Then the reaction mixture was stirred at room temperature for 3 h. After the consumption of 51 as indicated by TLC, the reaction mixture was neutralized with triethyl amine (1.00 mL) and then concentrated under reduced pressure. Purification by silica gel flash chromatography (100% EtOAc) afforded the anomeric mixture of the title compound 52 (0.13 g, 80%) as a yellow solid. $R_f$=0.4 (100% EtOAc).

Synthesis of 4-Amino-7-(1-methoxy-2,3',5-trihydroxy-D-ribofuranosyl)pyrolo [2,1-f] [1,2,4]triazine (13)

Compound 52 (0.10 g, 0.29 mmol, 1.00 equiv) was dissolved in a mixture of TFA/THF/water (1:1:1, 3.00 mL) at 0° C. Then the reaction mixture was

13

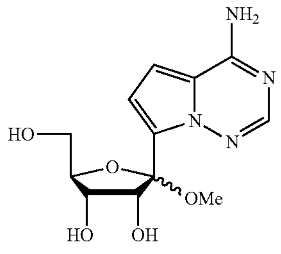

warmed to room temperature and stirred it for additional 3 h. After completion of the reaction, the mixture was evaporated to dryness to afford the titled compound 13 (50 mg, 58%) as an anomeric mixture. $R_f$=0.1 (20% MeOH/EtOAc).

Synthesis of 4-Acetylamino-7-(1'-hydroxy-2,3-O-isopropylidene-5-O-tert-butyldimethylsilyl-α/β-D-ribofuranosyl)pyrrolo[2,1-f][1,2,4]triazine (53)

To a stirring solution of 51 (0.44 g, 1.00 mmol, 1.00 equiv) in pyridine (0.11 M, 9 mL) was added DMAP (12 mg, 0.10 mmol, 0.10 equiv) followed by dropwise addition of acetic anhydride (0.11 mL, 1.20 mmol, 1.20 equiv) at 25° C. and the reaction stirred for 4 h. After the consumption of the lactone as indicated by TLC (10% EtOAc/hexane; $R_f$ 0.4), the reaction mixture was diluted with EtOAc

53

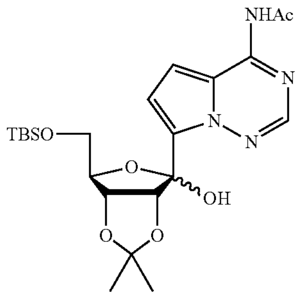

and consecutively washed with cold water and brine. The organic phase was separated, dried over anhydrous $Na_2SO_4$ and then concentrated under reduced pressure. Purification by silica gel flash chromatography (0-40% EtOAc/hexane) afforded the title compound (265 mg, 55%) as a yellow solid. $R_f$=0.3 (30% EtOAc/hexane); $^1H$ NMR (400 MHz, $CDCl_3$) δ 8.17 (s, 1H), 7.17-6.98 (m, 2H), 5.54 (s, 1H, C1'-OH), 5.14 (d, J=5.8 Hz, 1H), 4.95 (d, J=5.8 Hz, 1H), 4.42 (dt, J=28.1, 4.1 Hz, 1H), 3.96-3.79 (m, 2H), 2.60 (s, 3H), 1.24 (d, J=14.6 Hz, 6H), 0.95 (s, 9H), 0.16 (d, J=6.3 Hz, 6H); $^{13}C$ NMR (101 MHz, $CDCl_3$) δ 172.4, 171.2, 150.7, 150.6, 145.8, 145.3, 132.1, 130.8, 115.5, 115.4, 113.0, 112.9, 112.7, 112.7, 105.0, 103.6, 100.0, 87.6, 86.6, 82.9, 82.7, 82.4, 81.6, 64.8, 63.2, 26.5, 26.5, 25.9, 25.9, 25.8, 25.6, 25.2, 21.1, 20.9, 18.4, 18.2, −5.3, −5.3, −5.3, −5.4; FTIR ($cm^{-1}$) 3366, 2974, 2892, 1697, 1612, 1455, 1265, 1082, 1045; HRMS (ESI+) calcd for $C_{22}H_{35}N_4O_6Si$ $[M+Na]^+$ 501.2140, found 501.2147.

4-Acetylamino-7-(1-azido-2,3'-O-isopropylidene-5-O-tert-butyldimethylsilyl-α/β-D-ribofuranosyl)pyrrolo [2,1-f][1,2,4]triazine (54)

To a stirring solution of 53 (0.10 g, 0.19 mmol, 1.00 equiv) in $CH_2Cl_2$ (2 mL) was added $TMSN_3$ (0.04 mL, 0.29 mmol, 1.50 equiv) at 25° C. After 15 min TMSOTf (0.02 mL, 0.10 mmol, 0.50 equiv) was added dropwise to the reaction mixture at −5° C. and the reaction stirred for additional 30 min. After the consumption of 53 as indicated by TLC (10% EtOAc/hexane; $R_f$ 0.3) the reaction

54

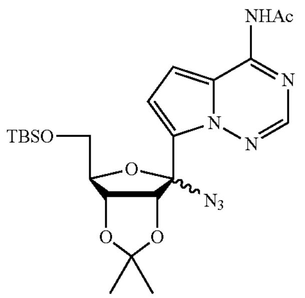

mixture was quenched with $Et_3N$. The reaction was diluted with $CH_2Cl_2$ and consecutively washed with cold water and brine. The organic phase was separated, dried over anhydrous $Na_2SO_4$ and then concentrated under reduced pressure. Purification by silica gel flash chromatography (0-30% EtOAc/hexane) afforded the title compound (82 mg, 85%) as a light-yellow solid. $R_f$=0.3 (10% EtOAc/hexane); $^1$H NMR (400 MHz, $CDCl_3$) δ 8.66 (s, 1H), 7.66-7.50 (m, 2H), 5.54 (dd, J=5.9, 2.2 Hz, 1H), 5.37 (d, J=5.5 Hz, 1H), 4.91 (t, J=6.5 Hz, 1H), 4.32 (dd, J=6.6, 2.3 Hz, 2H), 3.07 (s, 3H), 1.68 (s, 3H), 1.55 (s, 3H), 1.39 (s, 9H), 0.57 (s, 6H); $^{13}$C NMR (151 MHz, $CDCl_3$) δ 171.2, 150.3, 150.2, 145.2, 144.7, 132.3, 131.1, 115.4, 113.0, 112.8, 112.7, 104.9, 104.8, 99.9, 87.9, 87.7, 86.5, 86.5, 82.9, 82.6, 82.3, 82.3, 81.5, 64.8, 64.7, 63.1, 60.4, 29.7, 26.5, 26.4, 25.9, 25.9, 25.9, 25.8, 25.8, 25.6, 25.4, 25.2, 18.4, 18.4, 18.2, 14.2, −5.4, −5.4; FTIR ($cm^{-1}$) 2933, 2860, 2111, 1664, 1604, 1468, 840; HRMS (ESI+) calcd for $C_{22}H_{33}N_7O_5Si$ $[M-N_3]^+$ 461.2215, found 461.2213.

N,N'-(((3aR,4R,7R,7aR,10aR,11R,14R,14aR)-2,2,9,9-Tetramethyloctahydro-4H,11H-4,14:7,11-diepoxybis([1,3]dioxolo)[4,5-c:4',5'-i][1,7]dioxacyclododecine-4,11-diyl)bis(pyrrolo[2,1-f][1,2,4]triazine-7,4-diyl))diacetamide (56)

To a stirring solution of 54 (80 mg, 0.16 mmol, 1.00 equiv) in THF (2 mL) at 0° C. was added 1.00 M TBAF in THF (0.24 mL, 0.24 mmol, 1.50 equiv).

56

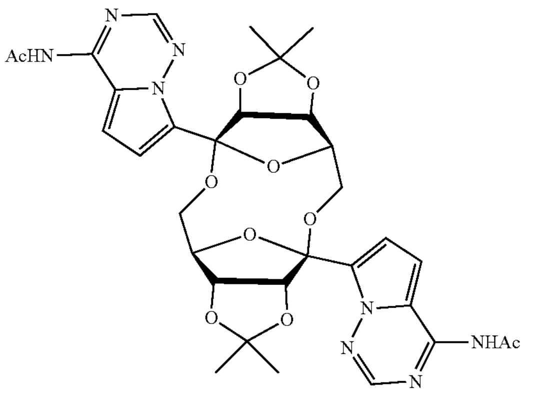

After the addition of TBAF, the reaction mixture was warmed to 25° C. and stirred for 1 h. After the completion of the reaction, as indicated by TLC (25% EtOAc/hexane; $R_f$ 0.4), the reaction was quenched with saturated aqueous $NH_4Cl$ (0.50 mL), then the reaction was diluted with ethyl acetate and consecutively washed with water and brine. The organic phase was separated, dried over anhydrous $Na_2SO_4$ and then concentrated under reduced pressure. Purification by silica gel flash chromatography (0-40% EtOAc/hexane) afforded the title compound (45 mg, 82%) as a white solid. $R_f$=0.4 (25% EtOAc/hexane); $[\alpha]^{23}_D$ −60 (c 0.33, MeOH); $^1$H NMR (400 MHz, $CDCl_3$) δ 8.22 (s, 1H), 7.15-7.12 (m, 2H), 5.13 (d, J=5.4 Hz, 1H), 4.88 (d, J=3.7 Hz, 1H), 4.61 (d, J=5.4 Hz, 1H), 3.75 (dd, J=7.2, 3.7 Hz, 1H), 3.67 (d, J=7.2 Hz, 1H), 2.61 (s, 3H), 1.39 (s, 3H), 1.30 (s, 3H); $^{13}$C NMR (101 MHz, $CDCl_3$) δ 171.7, 150.6, 146.0, 124.5, 116.2, 114.3, 112.8, 104.4, 82.0, 80.5, 78.5, 64.9, 26.2, 26.1, 25.8; FTIR ($cm^{-1}$) 2991, 2937, 1695,1612, 1457, 1377, 1215, 1082, 1034; HRMS (ESI+) calcd for $C_{32}H_{36}N_8O_{10}$ $[M+Na]^+$ 715.2447, found 715.2427.

4-[(tert-Butylcarbamoyl)amino]-7-(1-hydroxy-2',3-O-isopropylidene-5-O-tert-butyldimethylsilyl-α/β-D-ribofuranosyl)pyrrolo[2,1-f][1,2,4]triazine (57)

To a stirring solution of 51 (0.20 g, 0.45 mmol, 1.00 equiv) in THE (2 mL) was added DMAP (22 mg, 0.18 mmol, 0.40 equiv) and triethylamine (0.19 mL, 1.35 mmol, 3.00 equiv) at 0° C. Next, di-tert-butyl dicarbonate (0.21 mL, 0.90 mmol, 2.00 equiv) was added dropwise and the reaction mixture stirred for 1 h at 0° C. After the consumption of 51 as indicated by TLC (20% EtOAc/hexane; $R_f$ 0.5), the reaction mixture was diluted with EtOAc and consecutively washed with cold water and brine. The organic phase was separated, dried over anhydrous

57

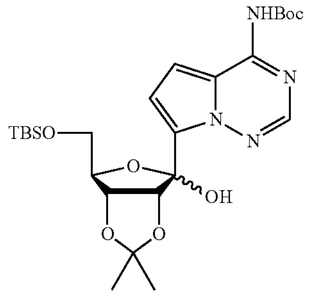

$Na_2SO_4$ and then concentrated under reduced pressure. Purification by silica gel flash chromatography (0-30% EtOAc/hexane) afforded the title compound (110 mg, 45%) as a yellow solid. $R_f$=0.5 (20% EtOAc/hexane); $^1$H NMR (400 MHz, $CDCl_3$) δ 8.14 (s, 1H), 7.21 (dd, J=4.8, 1.4 Hz, 1H), 7.02 (d, J=4.7 Hz, 1H), 5.56 (br s, 1H, C1'—OH), 5.11 (d, J=5.7 Hz, 1H), 4.92 (dd, J=5.7, 1.4 Hz, 1H), 4.46-4.33 (m, 1H), 3.88 (qd, J=10.7, 4.4 Hz, 2H), 1.54 (s, 9H), 1.22 (d, J=10.9 Hz, 6H), 0.92 (s, 9H), 0.13 (d, J=4.6 Hz, 6H); $^{13}$C NMR (101 MHz, $CDCl_3$) δ 151.4, 150.7, 145.8, 130.8, 115.7, 115.5, 112.7, 112.3, 105.9, 105.0, 100.0, 87.7, 86.6, 83.1, 82.7, 82.5, 81.6, 64.8, 63.1, 60.4, 28.2, 26.6, 26.5, 26.0, 25.9, 25.7, 25.3, 18.5, 14.2, −5.3, −5.3; FTIR ($cm^{-1}$) 3349, 2976, 2884, 1649, 1380, 1088; HRMS (ESI+) calcd for $C_{25}H_{40}N_4O_7Si$ [M+2H-Boc]$^+$ 437.2215, found 437.2219.

4-[(tert-Butylcarbamoyl) amino]-7-(1-azido-2',3-O-isopropylidene-5-O-tert-butyldimethylsilyl-α/β-D-ribofuranosyl] [pyrrolo[2,1-f][1,2,4]triazine (58)

To a stirring solution of 57 (0.10 g, 0.17 mmol, 1.00 equiv) in $CH_2Cl_2$ (2 mL) was added $TMSN_3$ (0.03 mL, 0.21 mmol, 1.20 equiv) at 25° C. and then mixture was stirred for 15 min. Next, TMSOTf (14 NL, 0.08 mmol, 0.50 equiv) was added dropwise to the reaction mixture at −5° C. and the reaction stirred for another 30 min. After the consumption of 57 as indicated by TLC (8% EtOAc/hexane; $R_f$

58

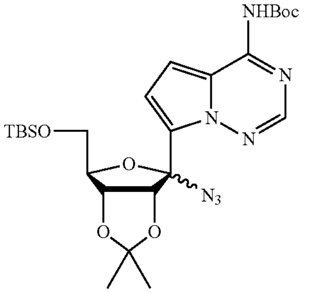

0.3), the reaction mixture was quenched with triethylamine, diluted with $CH_2Cl_{1-2}$, and consecutively washed with cold water and brine. The organic phase was separated, dried over anhydrous $Na_2SO_4$ and then concentrated under reduced pressure. Purification by silica gel flash chromatography (0-20% EtOAc/hexane) afforded the title compound 58 (88 mg, 85%) as a white solid. $R_f$=0.3 (8% EtOAc/hexane); $^1$H NMR (400 MHz, $CDCl_3$) δ 8.19 (s, 1H), 7.30 (d, J=4.7 Hz, 1H), 7.08 (d, J=4.7 Hz, 1H), 5.10 (d, J=5.9 Hz, 1H), 4.91 (d, J=8 Hz, 1H), 4.44 (td, J=6.4, 1.9 Hz, 1H), 3.86 (d, J=6.5 Hz, 2H), 1.56 (s, 9H), 1.22 (s, 3H), 1.10 (s, 3H), 0.93 (s, 9H), 0.12 (s, 6H); $^{13}$C NMR (101 MHz, $CDCl_3$) δ 151.4, 145.7, 128.4, 116.5, 113.6, 113.1, 113.1, 112.8, 106.0, 105.1, 100.8, 87.4, 87.3, 86.5, 86.4, 82.8, 82.7, 63.2, 28.2, 26.4, 26.1, 26.0, 25.8, 18.4, −0.4, −5.2, −5.2; FTIR ($cm^{-1}$) 2933, 2860, 2111, 1664, 1604, 1468, 840; HRMS (ESI+) calcd for $C_{25}H_{39}N_7O_6Si$ $[M+H]^+$ 562.2804, found 562.2765.

4-Amino-7-(1-azido-2;3',5'-hydroxy-α/β-D-ribofuranosyl)pyrrolo [2,1-f][1,2,4]triazine (14)

Compound 58 was synthesized in two steps. Step I: A solution of 30% TFA in $CH_2Cl_2$ (1 mL) was added to compound 58 (20 mg, 0.03 mmol, 1.00 equiv) at 0° C. and the mixture was stirred at the same temperature for 4 h. After the completion of the reaction, as indicated by TLC (20% EtOAc/hexane), the reaction mixture was evaporated to dryness. Then the crude was used for the next step without purification. Step II: A solution of TFA/THF/water (1:1:1, 1 mL) was

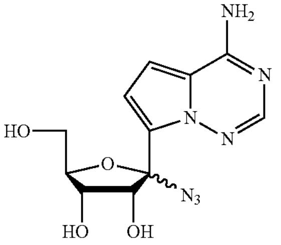

14-β

+

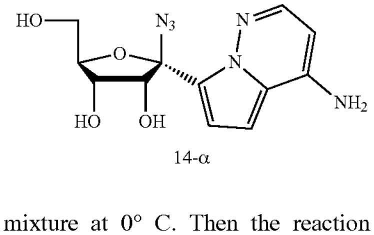

14-α added to the crude mixture at 0° C. Then the reaction mixture was warmed to 25° C. and stirred for 3 h. After completion of the reaction, the a mixture was evaporated to dryness. Purification by preparative TLC (1.5:8:0.5 MeOH/EtOAc/$Et_3N$) afforded the title compound (7.0 mg, 66%) as an anomeric mixture. $R_f$=0.3 (1.5:8:0.5 MeOH/EtOAc/$Et_3N$); $^1$H NMR (601 MHz, $CD_3OD$) δ 7.77 (s, 1H), 6.89 (d, J=4.5 Hz, 1H), 6.86 (d, J=4.4 Hz, 1H), 4.60 (d, J=4.6 Hz, 1H), 4.34 (dd, J=8.0, 4.5 Hz, 1H), 4.11 (td, J=7.5, 3.1 Hz, I H), 3.85 (dd, J=11.8, 3.2 Hz, 1H), 3.67 (dd, J=11.7, 7.1 Hz, 1H); $^{13}$C NMR (151 MHz, MeOD) δ 157.2, 147.9, 128.1, 114.9, 109.2, 102.0, 84.6, 76.6, 73.5, 65.3, 60.1; FTIR ($cm^{-1}$) 2469, 2247, 2072, 1123, 1092, 947; HRMS (ESI+) calcd for $C_{11}H_{13}N_4O_4$ $[M-N_3]^+$ 265.0931, found 265.0937.

What is claimed is:

1. A compound of the formula:

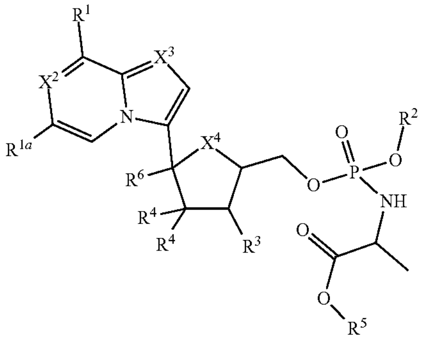

or a pharmaceutically acceptable salt or solvate thereof wherein:

$R^1$ is H, halo, alkyl, amino or $OR^7$, wherein $R^7$ is H or alkyl;

$R^{1a}$ is amino;

$R^2$ is aryl or heteroaryl;

$R^3$ and $R^4$ are each, independently, alkyl, halo, haloalkyl or $OR^7$, wherein $R^7$ is H or alkyl;

$R^5$ is alkyl;

$R^6$ is cyano;

$X^2$ is N or CH;

$X^3$ is N or CH; and $X^4$ is O, NH, S or $CH_2$.

2. The compound of claim 1, or a pharmaceutically acceptable salt or solvate thereof, wherein $R^2$ is aryl.

3. The compound of claim 1, or a pharmaceutically acceptable salt or solvate thereof, wherein at least one of $R^3$ and $R^4$ is OH.

4. The compound of claim 1, or a pharmaceutically acceptable salt or solvate thereof, wherein at least one of $R^3$ and $R^4$ is OH and the other is halo.

5. The compound of claim 1, or a pharmaceutically acceptable salt or solvate thereof, wherein at least one of $R^3$ and $R^4$ is F.

6. The compound of claim 1, or a pharmaceutically acceptable salt or solvate thereof, wherein $R^5$ is $C_6$-alkyl.

7. A compound of the formula:

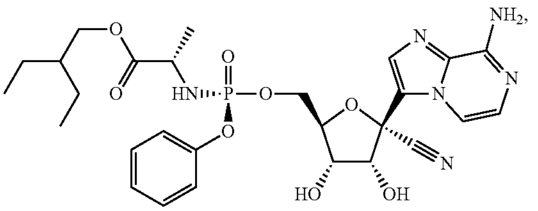

-continued
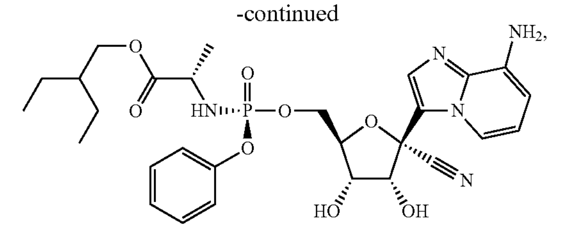
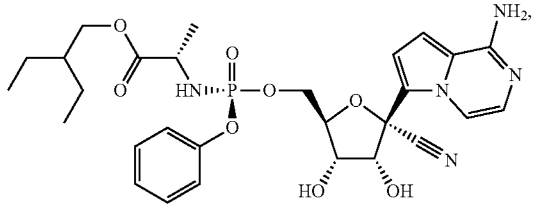
or
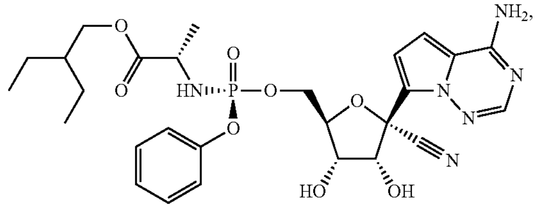
or a pharmaceutically acceptable salt or solvate thereof.
8. A pharmaceutical composition comprising one or more compounds of claim 1, or a pharmaceutically acceptable salt or solvate thereof, and a pharmaceutically acceptable carrier.
* * * * *